US010351615B2

(12) United States Patent
Fares et al.

(10) Patent No.: US 10,351,615 B2
(45) Date of Patent: Jul. 16, 2019

(54) METHODS OF TREATMENT WITH LONG-ACTING GROWTH HORMONE

(75) Inventors: Fuad Fares, Hourfish Village (IL); Udi Eyal Fima, Dvira (IL)

(73) Assignee: OPKO Biologics Ltd., Kiryat Gat (IL)

( * ) Notice: Subject to any disclaimer, the term of this patent is extended or adjusted under 35 U.S.C. 154(b) by 0 days.

(21) Appl. No.: 14/236,509

(22) PCT Filed: Aug. 2, 2012

(86) PCT No.: PCT/IL2012/050288
§ 371 (c)(1),
(2), (4) Date: Aug. 27, 2014

(87) PCT Pub. No.: WO2013/018098
PCT Pub. Date: Feb. 7, 2013

(65) Prior Publication Data
US 2014/0371144 A1     Dec. 18, 2014

Related U.S. Application Data

(63) Continuation-in-part of application No. 13/195,931, filed on Aug. 2, 2011, now Pat. No. 8,450,269.

(51) Int. Cl.
C07K 14/59     (2006.01)
C07K 14/61     (2006.01)
C07K 14/505    (2006.01)

(52) U.S. Cl.
CPC ............ C07K 14/61 (2013.01); C07K 14/505 (2013.01); C07K 14/59 (2013.01); C07K 2319/00 (2013.01)

(58) Field of Classification Search
None
See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,400,316 A | 8/1983 | Katsuragi et al. |
| 4,666,828 A | 5/1987 | Gusella |
| 4,683,202 A | 7/1987 | Mullis |
| 4,801,531 A | 1/1989 | Frossard |
| 4,853,332 A | 8/1989 | Mark et al. |
| 4,873,316 A | 10/1989 | Meade et al. |
| 4,879,219 A | 11/1989 | Wands et al. |
| 4,911,691 A | 3/1990 | Aniuk et al. |
| 5,011,771 A | 4/1991 | Bellet et al. |
| 5,118,666 A | 6/1992 | Habener |
| 5,177,193 A | 1/1993 | Boime et al. |
| 5,192,659 A | 3/1993 | Simons |
| 5,272,057 A | 12/1993 | Smulson et al. |
| 5,281,521 A | 1/1994 | Trojanowski et al. |
| 5,338,835 A | 8/1994 | Boime |
| 5,405,945 A | 4/1995 | Boime et al. |
| 5,464,764 A | 11/1995 | Capecchi et al. |
| 5,487,992 A | 1/1996 | Capecchi et al. |
| 5,585,345 A | 12/1996 | Boime |
| 5,597,797 A | 1/1997 | Clark |
| 5,643,575 A | 7/1997 | Martinez et al. |
| 5,681,567 A | 10/1997 | Martinez et al. |
| 5,705,478 A | 1/1998 | Boime |
| 5,712,122 A | 1/1998 | Boime et al. |
| 5,759,818 A | 6/1998 | Boime |
| 5,792,460 A | 8/1998 | Boime |
| 5,919,455 A | 7/1999 | Greenwald et al. |

(Continued)

FOREIGN PATENT DOCUMENTS

| | | |
|---|---|---|
| CN | 1528787 | 9/2004 |
| CN | 1528894 A | 9/2004 |

(Continued)

OTHER PUBLICATIONS

Havron et al., Growth Hormone and IGF Research, (2010) vol. 20, Supp. Suppl. 1, pp. S4-S5. Abstract Number: OR2,8, Meeting Info: 5th International Congress of the GRS and the IGF Society. New York, NY, United States. Oct. 3, 2010-Oct. 7, 2010.*

(Continued)

Primary Examiner — Christina M Borgeest
(74) Attorney, Agent, or Firm — Mark S. Cohen; Pearl Cohen; Zedek Latzer Baratz LLP

(57) ABSTRACT

Use of a growth hormone protein and polynucleotides encoding same comprising an amino-terminal carboxy-terminal peptide (CTP) of chorionic gonadotrophin and two carboxy-terminal chorionic gonadotrophin CTPs attached to the growth hormone in methods of inducing weight loss or body fat reduction, methods of increasing insulin-like growth factor (IGF-1) levels, and methods of reducing the dosing frequency of a growth hormone in a human subject are disclosed. Pharmaceutical compositions comprising the growth hormone and polynucleotides encoding the growth hormone of the invention and methods of using same are also disclosed.

9 Claims, 6 Drawing Sheets

Specification includes a Sequence Listing.

(56) References Cited

U.S. PATENT DOCUMENTS

| | | |
|---|---|---|
| 5,929,028 A | 7/1999 | Skrabanja et al. |
| 5,932,447 A | 8/1999 | Siegall |
| 5,935,924 A | 8/1999 | Bunting et al. |
| 5,958,737 A | 9/1999 | Boime et al. |
| 6,028,177 A | 2/2000 | Boime |
| 6,083,725 A | 7/2000 | Selden et al. |
| 6,103,501 A | 8/2000 | Boime et al. |
| 6,113,906 A | 9/2000 | Greenwald et al. |
| 6,225,449 B1 | 5/2001 | Boime |
| 6,238,890 B1 | 5/2001 | Boime |
| 6,242,580 B1 | 6/2001 | Boime et al. |
| 6,306,654 B1 | 10/2001 | Boime et al. |
| 6,310,183 B1 | 10/2001 | Johannessen et al. |
| 6,340,742 B1 | 1/2002 | Burg et al. |
| 6,514,729 B1 | 2/2003 | Bentzien |
| 6,897,039 B2 | 5/2005 | Graversen et al. |
| 7,081,446 B2 | 7/2006 | Lustbader |
| 7,091,326 B2 | 8/2006 | Lee et al. |
| 7,094,566 B2 | 8/2006 | Medlock et al. |
| 7,141,547 B2 | 11/2006 | Rosen et al. |
| 7,202,215 B2 | 4/2007 | Lustbader |
| 7,217,689 B1 | 5/2007 | Elliot et al. |
| 7,371,372 B2 | 5/2008 | Chaturvedi et al. |
| 7,371,373 B2 | 5/2008 | Shirley et al. |
| 7,425,539 B2 | 9/2008 | Donovan et al. |
| 7,442,684 B2 | 10/2008 | Lustbader et al. |
| 7,459,429 B2 | 12/2008 | Klima et al. |
| 7,459,435 B2 | 12/2008 | Lehmann et al. |
| 7,459,436 B2 | 12/2008 | Lehmann et al. |
| 7,553,940 B2 | 6/2009 | Fares et al. |
| 7,553,941 B2 | 6/2009 | Fares et al. |
| 7,585,837 B2 | 9/2009 | Shechter et al. |
| 7,649,084 B2 | 1/2010 | Ferguson |
| 7,666,835 B2 | 2/2010 | Bloom et al. |
| 7,795,210 B2 | 9/2010 | Defrees et al. |
| 8,008,454 B2 | 8/2011 | Lee et al. |
| 8,048,846 B2 | 11/2011 | Chahal et al. |
| 8,048,848 B2 | 11/2011 | Fares et al. |
| 8,048,849 B2 | 11/2011 | Fares et al. |
| 8,063,015 B2 | 11/2011 | Defrees et al. |
| 8,097,435 B2 | 1/2012 | Fares et al. |
| 8,110,376 B2 | 2/2012 | Fares et al. |
| 8,114,836 B2 | 2/2012 | Fares et al. |
| 8,129,330 B2 | 3/2012 | Martinez et al. |
| 8,426,166 B2 | 4/2013 | Fares et al. |
| 8,450,269 B2 | 5/2013 | Fares et al. |
| 8,465,958 B2 | 6/2013 | Lopez De Leon et al. |
| 2001/0007757 A1 | 7/2001 | Boime et al. |
| 2001/0008895 A1 | 10/2001 | Bisgaier et al. |
| 2001/0028895 A1 | 10/2001 | Bisgaier et al. |
| 2002/0127652 A1 | 9/2002 | Schambye |
| 2002/0160944 A1 | 10/2002 | Boime et al. |
| 2003/0113871 A1 | 6/2003 | Lee et al. |
| 2003/0143694 A1 | 7/2003 | Lustbader |
| 2003/0216313 A1 | 11/2003 | Lustbader et al. |
| 2004/0009902 A1 | 1/2004 | Boime et al. |
| 2004/0018240 A1 | 1/2004 | Ohmachi et al. |
| 2004/0053370 A1 | 3/2004 | Glaesner |
| 2004/0057996 A1 | 3/2004 | Takada et al. |
| 2004/0115774 A1 | 6/2004 | Kochendoerfer |
| 2004/0209804 A1 | 10/2004 | Govardhan et al. |
| 2005/0234221 A1 | 10/2005 | Medlock et al. |
| 2006/0073571 A1 | 4/2006 | Saxena et al. |
| 2006/0088595 A1 | 4/2006 | Asakawa et al. |
| 2006/0160177 A1 | 7/2006 | Okkels et al. |
| 2006/0171920 A1 | 8/2006 | Shechter et al. |
| 2007/0184530 A1 | 8/2007 | Fares et al. |
| 2007/0190610 A1 | 8/2007 | Fares et al. |
| 2007/0190611 A1 | 8/2007 | Fares et al. |
| 2007/0298041 A1 | 12/2007 | Tomlinson |
| 2008/0064856 A1 | 3/2008 | Warne et al. |
| 2008/0206270 A1 | 8/2008 | Minev |
| 2009/0053185 A1 | 2/2009 | Schulte et al. |
| 2009/0087411 A1 | 4/2009 | Fares et al. |
| 2009/0130060 A1 | 5/2009 | Weimer et al. |
| 2009/0221037 A1 | 9/2009 | Lee et al. |
| 2009/0221485 A1 | 9/2009 | James |
| 2009/0270489 A1 | 10/2009 | Fares et al. |
| 2009/0275084 A1 | 11/2009 | Fares et al. |
| 2009/0286733 A1 | 11/2009 | Fares et al. |
| 2009/0312254 A1 | 12/2009 | Fares et al. |
| 2010/0081614 A1 | 4/2010 | Fares et al. |
| 2010/0144617 A1 | 6/2010 | Sinha Roy et al. |
| 2010/0310546 A1 | 12/2010 | Schuster et al. |
| 2010/0317585 A1 | 12/2010 | Fima et al. |
| 2011/0004172 A1 | 1/2011 | Eckstein et al. |
| 2011/0034374 A1 | 2/2011 | Bloom et al. |
| 2011/0065660 A1 | 3/2011 | Baron et al. |
| 2011/0152182 A1 | 6/2011 | Alsina-Fernandez et al. |
| 2011/0166063 A1 | 7/2011 | Bossard et al. |
| 2011/0223151 A1 | 9/2011 | Behrens et al. |
| 2011/0286967 A1 | 11/2011 | Fares et al. |
| 2012/0004286 A1 | 1/2012 | Fares et al. |
| 2012/0015437 A1 | 1/2012 | Fares et al. |
| 2012/0035101 A1 | 2/2012 | Fares et al. |
| 2012/0114651 A1 | 5/2012 | De Wildt et al. |
| 2012/0208759 A1 | 8/2012 | Fima et al. |
| 2013/0184207 A1 | 7/2013 | Fares et al. |
| 2013/0243747 A1 | 9/2013 | Fima et al. |
| 2014/0113860 A1 | 4/2014 | Fima et al. |
| 2014/0316112 A1 | 10/2014 | Hershkovitz et al. |
| 2015/0038413 A1 | 2/2015 | Fares et al. |
| 2015/0072924 A1 | 3/2015 | Fima et al. |
| 2015/0158926 A1 | 6/2015 | Fares et al. |

FOREIGN PATENT DOCUMENTS

| | | |
|---|---|---|
| EP | 0167825 | 1/1986 |
| EP | 0264166 | 4/1988 |
| EP | 1319712 A2 | 6/2003 |
| EP | 2532674 A1 | 12/2012 |
| EP | 2420251 | 3/2013 |
| JP | H8-509218 | 10/1996 |
| JP | 2002/226365 | 8/2002 |
| JP | 2002/255857 | 9/2002 |
| JP | 2004/269516 | 9/2004 |
| JP | 2012/519119 | 8/2012 |
| KR | 20030037598 A | 5/2003 |
| WO | WO 89/10756 | 11/1989 |
| WO | WO 1993/006844 A1 | 4/1993 |
| WO | WO 94/24148 A1 | 10/1994 |
| WO | WO 99/25849 | 5/1999 |
| WO | WO 00/23472 A2 | 4/2000 |
| WO | WO 2002/036169 A2 | 5/2002 |
| WO | WO 02/48194 A1 | 6/2002 |
| WO | WO 2003/038100 A1 | 5/2003 |
| WO | WO 2003/048210 A1 | 6/2003 |
| WO | WO 2002/085311 A2 | 10/2003 |
| WO | WO 2004/006756 | 1/2004 |
| WO | WO 2004/089280 A2 | 10/2004 |
| WO | WO 2005/035761 A1 | 4/2005 |
| WO | WO 2005/080544 | 9/2005 |
| WO | WO 2006/134340 | 12/2006 |
| WO | WO 2007/094985 | 8/2007 |
| WO | WO 2007/149406 A2 | 12/2007 |
| WO | WO 2010/007622 | 1/2010 |
| WO | WO 2010/097077 | 9/2010 |
| WO | WO 2011/004361 | 1/2011 |
| WO | WO 2011/087672 | 7/2011 |
| WO | WO 2012/011752 | 5/2012 |
| WO | WO 2012/167251 | 12/2012 |
| WO | WO 2013/157002 | 10/2013 |
| WO | WO 2013/183052 | 12/2013 |
| WO | WO 2014/080401 | 5/2014 |

OTHER PUBLICATIONS

The Guidance for Industry (Estimating the Maximum Safe Starting Dose in Initial Clinical Trials for Therapeutics in Adult Healthy Volunteers; J:\!GUJDANC\554 Jfnlcln1.doc), published by the U.S. DHHS Food and Drug Administration Center for Drug Evaluation and Research (Year: 2005).*

(56) References Cited

OTHER PUBLICATIONS

Rosario, Arq Bras Endocrinol Metab. 2010; 54: 477-81 (Year: 2010).*
Fares et al. "Development of a Long-Acting Erythropoietin by Fusing the Carboxyl-Terminal Peptide of Human Chorionic Gonadotropin b-Subunit to the Coding Sequence of Human Erythropoietin." Endoncrinology. 2007, vol. 148(10), p. 5081-7.
U.S. Appl. No. 60/764,761, filed Feb. 3, 2006, Fares et al.
U.S. Appl. No. 61/224,366, filed Jul. 9, 2009, Fima et al.
U.S. Appl. No. 11/700,910, filed Feb. 1, 2007, Fares et al.
U.S. Appl. No. 11/700,911, filed Feb. 1, 2007, Fares et al.
U.S. Appl. No. 11/702,156, filed Feb. 5, 2007, Fares et al.
U.S. Appl. No. 12/216,989, filed Jul. 14, 2008, Fares et al.
U.S. Appl. No. 12/401,746, filed Mar. 11, 2009, Fares et al.
U.S. Appl. No. 12/401,755, filed Mar. 11, 2009, Fares et al.
U.S. Appl. No. 12/476,916, filed Jun. 2, 2009, Fares et al.
Amirizahdeh et al. "Expression of biologically active recombinant B-domain-deleted human VIII in mammalian cells" Journal of Science, Islamic Republic of Iran. Abstract. 16(2):103-112, (2005).
Anson et al.; "The gene structure of human anti-haemophilic factor IX", The EMBO Journal (1984) 3(5):1053-1060.
Banerji et al. "A lymphocyte-specific cellular enhancer is located downstream of the joining region in immunoglobulin heavy chain genes" Cell 33:729-740 (1983).
Barker et al. "An immunomagnetic-base method for the purification of ovarian cancer cells from patient-derived ascites" (Gynecologic Oncology 82, 57-63, 2001).
Bengtsson et al. "Treatment of adults with growth hormone (GH) deficiency with recombinant human GH" J Clin Endocrinol Metab. Feb. 1993;76(2):309-17.
Berntorp et al.; "The pharmacokinetics of clotting factor therapy"; Haemophilia (2003) 9:353-359.
Bitter et al. "Expression and secretion vectors for yeast" Methods in Enzymol. 153:516-544 (1987).
Bjorkman et al. Pharmacokinetics of Coagulation Factors Clinical Relevance for Patients with Haemophilia. Clin Pharmacokinet vol. 40 (11): 815-832 (2001).
Bohl et al. "Improvement of erythropoiesis in b-thalassemic mice by continuous erythropoietin delivery from muscle" Blood 95:2793-2798 (2000).
Boissel et al. "Erythropoietin structure-function relationships" The Journal of Biological Chemistry 268(21):15983-15993 (1993).
Booth et al. "The use of a 'universal' yeast expression vector to produce an antigenic protein of *Mycobacterium leprae*" Immunol. Lett. 19:65-70 (1988).
Brisson et al. "Expression of a bacterial gene in plants by using a viral vector" Nature, 310:511-514 (1984).
Brogli et al. "Light-Regulated Expression of a Pea Ribulose-1,5-Bisphosphat Carboxylase Small Subunit Gene in Transformed Plant Cells" Science 224:838-843 (1984).
Brunetti-Pierri et al. "Bioengineered factor IX molecules with increased catalytic activity improve the therapeutic index of gene therapy vectors for hemophilia B." Human Gene Therapy 20.5: 479-485 (2009).
Buchwald et al. "Long-term, continuous intravenous heparin administration by an implantable infusion pump in ambulatory patients with recurrent venous thrombosis" Surgery 88:507-516 (1980).
Byrne et al. "Multiplex gene regulation: A two-tiered approach to transgene regulation in transgenic mice" Proc. Natl. Acad. Sci USA 86:5473-5477 (1989).
Calame et al. "Transcriptional Controlling Elements in the Immunoglobulin and T Cell Receptor Loci" Adv. Immunol 43:235-275 (1988).
Claxton et al., "A systematic review of the associations between dose regimens and medication compliance." Clinical Therapeutics 23.8: 1296-1310 (2001).
Coleman et al., "Dosing frequency and medication adherence in chronic disease." Journal of managed care pharmacy: JMCP 18.7: 527-539 (2012).

Coruzzi et al. "Tissue-specific and light-regulated expression of a pea nuclear gene encoding the small subunit of ribulose-1,5-bisphosphate carboxylase" The EMBO Journal 3:1671-1680 (1984).
Cutfield et al., "Non-compliance with growth hormone treatment in children is common and impairs linear growth." PLoS One 6.1: e16223 (2011).
Database Geneseq [Online] Apr. 7, 2005, "Human interferon beta (without signal peptide)." XP002664024 retrieved from EBI accession No. GSP: ADW02285, Database accession No. ADW02285.
Database Geneseq [online]; "Epogen signal peptide", XP002685292, Mar. 24, 2005.
Davis CG et al. "Deletion of clustered O-linked carbohydrates does not impair function of low density lipoprotein receptor in transfected fibroblasts" J Biol Chem. 261(6):2828-38, Feb. 25, 1986.
Diederichs et al., "Liposome in kosmetika and arzneimitteln." Pharmazeutische Industrie 56.3: 267-275 (1994).
Dong et al. "The prolonged half-lives of new erythropoietin derivatives via peptide addition" Biochemical Research Communications, 339(1):380-385 (Jan. 6, 2006).
Drake et al. "Optimizing GH therapy in adults and children" Endocr Rev. Aug. 2001;22(4):425-50.
Edlunch et al. "Cell-Specific Expression of the Rat Insulin Gene: Evidence for Role of Two Distinct 5' Flanking Elements" Science 230:912-916 (1985).
EP Search Report for Application No. 12150722.2 dated Jun. 4, 2012.
European Search Report Application No. EP 10796803 dated Feb. 28, 2013.
European Search Report for Application No. 07749922 dated Oct. 8, 2009.
European Search Report for EP Patent Application No. 12179805.2-1212 dated Nov. 9, 2012.
European Search Report for EP Patent Application No. 12179821.9-1212 dated Nov. 12, 2012.
European Search Report for European Patent Application No. EP 10796803 dated Feb. 28, 2013.
Extended European Search Report for EP patent application No. 09797630.2, dated Dec. 5, 2011.
Fares et al. "Design of a long-acting follitropin agonist by fusing the C-terminal sequence of the chorionic gonadotropin beta subunit to the follitropin beta subunit" Proc Nati Acad Sci U S A., 89(10): 4304-4308, May 15, 1992.
Fares et al. "Designing a Long Acting Erythropoietin by Fusing Three CarboxylTerminal Peptides of Human Chorionic Gonadotropin 13 Subunit to the N-Terminal and C-Terminal Coding Sequence." Int J Cell Biol. 2011; 275063.
Fares et al. "Designing a long-acting human growth hormone (hGH) by fusing the carboxy-terminal peptide of human chorionic gonadotropin B-subunit to the coding sequence of hGH" Endocrinology 151 (9):4410-4417 (2010).
Fares et al. "Growth hormone (GH) retardation of muscle damage due to immobilization in old rats. Possible intervention with a new long-acting recombinant GH" Ann N Y Acad Sci. 786:430-43 (Jun. 15, 1996).
Fayad et al. "Update of the M. D. Anderson Cancer Center experience with hyper-CVAD and rituximab for the treatment of mantle cell and Burkitt-type lymphomas" Clin Lymphoma Myeloma. Dec. 2007;8 Suppl 2:S57-62.
Fingel, et al., "The Pharmacological Basis of Therapeutics." Ch. I p. I. (1975).
Freshney "Culture of animal cells: A manual of basic technique" (Culture of Animal Cells, a Manual of Basic Technique, Alan R. Liss, Inc., 1983, New York, p. 4).
Fuentes-Prior et al. "Structural basis for the anticoagulant activity of the thrombin-thrombomodulin complex" Nature. Mar. 30, 2000; 404 (6777):518-25.
Furuhashi et al. Fusing the carboxy-terminal peptide of the chorionic gonadotropin (CG) b-subunit to the common α-submit: Retention of O-linked glycosylation and enhanced in vivo bioactivity of chimeric human CG: Molecular Endocrinology 9(1):54-63 (1995).
Furuhashi et al. "Processing of O-linked glycosylation in the chimera consisting of alpha-subunit and carboxyl-terminal peptide of the human chorionic gonadotropin beta-subunit is affected by

(56) References Cited

OTHER PUBLICATIONS dimer formation with follicle-stimulating hormone beta-subunit" Endocrine Journal 51(1):53-59 (2004).
Gao et al., "Erythropoietin gene therapy leads to autoimmune anemia in macaques" Blood 103(9):3300-3302 (2004).
Gardella et al. "Expression of Human Parathyroid Hormone-(1-84) in *Escherichia coli* as a Factor X-cleavable Fusion Protein" J. Biol. Chem. 265:15854-15859 (1990).
Gellerfors et al. "Characterisation of a secreted form of recombinant derived human growth hormone, expressed in *Escherichia coli* cells", J Pharm Biomed Anal 7(2):173-83 (1989).
Ghosh et al., "Activity and regulation of factor VIIa analogs with increased potency at the endothelial cell surface." Journal of Thrombosis and Haemostasis 5.2: 336-346 (2007).
Goodson, in "Medical applications of controlled release." vol. 2: 115-138 (1984).
Gurley et al. "Upstream Sequences Required for Efficient Expression of a Soybean Heat Shock Gene" Mol.Cell.Biol 6:559-565 (1986).
Hacke et al. "Intravenous thrombolysis with recombinant tissue plasminogen activator for acute hemispheric stroke. The European Cooperative Acute Stroke Study (ECASS)" JAMA. (1995) 274(13):1017-1025.
Hammerling et al. "In vitro bioassay for human erythropoietin based on proliferative stimulation of an erythroid cell line and analysis of carbohydrate-dependent microheterogeneity" Journal of Pharm. Biomed. Analysis 14(11):1455-1469 (1996).
Hamming et al. "In vitro bioassay for human erythropoietin based on proliferative stimulation of an erythroid cell line and analysis of carbohydrate-dependent microheterogeneity" Journal of Pharm. Biomed. Analysis 14(11):1455-1469 (1996).
Heffernan et al., "Effects of oral administration of a synthetic fragment of human growth hormone on lipid metabolism." American Journal of Physiology-Endocrinology and Metabolism 279.3: E501-E507 (2000).
Houdebine, L., "The methods to generate transgenic animals and to control transgene expression" Journal of Biotechnology 98:145-160 (2002).
Huston et al. "Protein engineering of antibody binding sites: Recovery of specific activity in an anti-digoxin single-chain Fv analogue produced in *Escherichia coli*" Proc. Natl. Acad. Sci. USA vol. 85, pp. 5879-5883, Biochemistry, Aug. 1988.
International preliminary report on patentability Application No. PCT/IL2010/000532 dated Jan. 19, 2012.
International Search Report and Written Opinion for PCT Application No. PCT/IL13/50107 dated Jul. 10, 2013.
International Search Report and written Opinion of corresponding PCT Application No. PCT/IL10/00532 dated Apr. 11, 2011.
International Search Report for PCT Application No. PCT/IL 12/50288 dated Jan. 28, 2013.
International Search Report for PCT Application No. PCT/IL09/00700 dated Feb. 4, 2010.
International Search Report for PCT Application No. PCT/IL2012/50288 dated Jan. 28, 2013.
International Search Report for PCT Application No. PCT/US07/02767 dated Feb. 15, 2008.
International Search Report for PCT Application No. PCT/US07/03014 dated Sep. 22, 2008.
Isgaard et al. "Effects of local administration of GH and IGF-1 on longitudinal bone growth in rats" Am J Physiol. Apr. 1986;250(4 Pt 1):E367-72.
Joshi et al., "Recombinant thyrotropin containing beta-subunit chimera with the human chorionic gonadotropin-beta carboxy-terminus is biologically active, with a prolonged plasma half-life: role of carbohydrate in bioactivity and metabolic clearance," Endocrinology, Sep. 1995; 136(9):3839-48.
Kelly et al. "Outcomes of patients with Burkitt lymphoma older than age 40 treated with intensive chemotherapeutic regimens." Clin Lymphoma Myeloma. Aug. 2009;9(4):307-10.
Kotler et al., "Effects of Growth Hormone on Abnormal Visceral Adipose Tissue Accumulation and Dyslipidemia in HIV-Infected Patients." Journal Acquired Immune Deficiency Syndrome vol. 35/3:239-252 (Mar. 2004).
Langer Robert "New Methods of Drug Delivery" Science 249:1527-1533 (1990).
Le et al. Improved Vancomycin Dosing in Children Using Area Under the Curve Exposure. Pediatr Infect Dis J vol. 32, pp. e 155-e 1 63 (2013).
Li et al. Bioassay of hGH .1. Weight gain of hypophysectomized rats. Abstract, Yaowu Fenxi Zazhi 15(2),3-7 (1995).
Lippin et al. "Human erythropoietin gene therapy for patients with chronic renal failure" Blood 106(7):2280-2286 (2005).
Lo et al. The Effects of Recombinant Human Growth Hormone on Body Composition and Glucose Metabolism in HIV-Infected Patients with Fat Accumulation. The Journal of Clinical Endocrinology & Metabolism 86(8):3480-3487 (Aug. 2001).
Maston et al., "Chorionic gonadotropin beta subunit [*Homo sapiens*]" NCBI Accession No. AAL69705.1 (Apr. 3, 2002).
Matsumoto et al. The measurement of low levels of factor VIII or factor IX in hemophilia A and hemophilia B plasma by clot waveform analysis and thrombin generation assay. Journal of Thrombosis and Haemostasis vol. 4:377-384 (2006).
Matsuo et al. "Thrombolysis by human tissue plasminogen activator and urokinase in rabbits with experimental pulmonary embolus" Nature. Jun. 18, 1981;291(5816):590-1.
Maun et al., "Disulfide locked variants of factor VIIa with a restricted β-strand conformation have enhanced enzymatic activity." Protein Science 14.5: 1171-1180 (2005).
Meulien et al., "Increased biological activity of a recombinant factor IX variant carrying alanine at position+ 1." Protein Engineering 3.7: 629-633 (1990).
Milton et al. The delineation of a decapeptide gonadotropin-releasing sequence in the carboxyl-terminal extension of the human gonadotropin-releasing hormone precursor J Biol Chem. Dec. 25, 1986;261(36):16990-7.
Mj Kessler et al. "Structure and location of the O-glycosidic carbohydrate units of human chorionic gonadotropin" J Biol Chem. 25;254(16):7909-14 , Aug. 1979.
Ngo et al. "Computational Complexity, Protein Structure Protein Prediction and the Levinthal Paradox" in Birkhauser the Protein Folding Problem and Tertiary Structure Prediction, pp. 433-440 and 492-495 (1994).
Oosterhof et al. Regulation of whole body energy homeostasis with growth hormone replacement therapy and endurance exercise Physiol Genomics. Jun. 28, 2011;43(12):739-48.
Oosterhof et al. Regulation of whole body energy homeostasis with growth hormone replacement therapy and endurance exercise Physiol Genomics. Jun. 28, 2011;43(12):739-48. doi: 10.1152/physiolgenomics.00034.2010. Epub Mar. 29, 2011.
Persson et al. "Recombinant coagulation factor VIIa—from molecular to clinical aspects of a versatile haemostatic agent", Thrombosis Research (2010) 125:483-489.
Philips A. "The challenge of gene therapy and DNA delivery" J Pharm. Pharmacology 53:1169-1174 (2001).
Pinkert et al. "An albumin enhancer located 10 kb upstream functions along with its promoter to direct liver-specific expression in transgenic mice" Genes Dev. 1:268-277 (1987).
Reiter et al. "A multicenter study of the efficacy and safety of sustained release GH in the treatment of naive pediatric patients with GH deficiency" J Clin Endocrinol Metab. 86(10):4700-6 (Oct. 2001).
Ronzi et al. Optimisation of a freeze-drying process of high purity Factor VIII and Factor IX concentrates. Chemical Engineering and Processing. vol. 42:751-757 (2003).
Rudman et al. "Effects of human growth hormone in men over 60 years old" N Engl J Med. Jul. 5, 1990;323(1):1-6.
Russell et al. "Local injections of human or rat growth hormone or of purified human somatomedin-C stimulate unilateral tibial epiphyseal growth in hypophysectomized rats" Endocrinology. Jun. 1985;116(6):2563-7.

(56) References Cited

OTHER PUBLICATIONS

Saudek et al. "A preliminary trial of the programmable implantable medication system for insulin delivery" N Engl J Med. 321:574 (1989).
Schein, Catherine H. "The shape of the messenger: Using protein structure information to design novel cytokine-based therapeutics" Abstract; Current Pharmaceutical Design 8(24):2113-2129 (2002).
Scheuttrumpf et al., "Factor IX variants improve gene therapy efficacy for hemophilia B." Blood 105.6: 2316-2323 (2005).
Schulte "Half-life extension through albumin fusion technologies", Thrombosis Research (2009) 124 Suppl. 2;S6-S8.
Sefton, "Implantable pumps." Critical Reviews in Biomedical Engineering 14.3: 201-240 (1986).
Sheffield et al. "Effects of genetic fusion of factor IX to albumin on in vivo clearance in mice and rabbits", Blackwell Publishing Ltd, British Journal of Haematology (2004) 126:565-573.
Silverman et al. "A long-acting human growth hormone (Nutropin Depot): Efficacy and safety following two years of treatment in children with growth hormone deficiency" J Pediatr Endocrinol Metab.15 Suppl 2:715-22. (May 2002).
Smeland et al. "Treatment of Burkitt's/Burkitt-like lymphoma in adolescents and adults: a 20-year experience from the Norwegian Radium Hospital with the use of three successive regimens."Ann Oncol. Jul. 2004;15(7):1072-8.
Speiser et al. "Optimization of spray-dried and -congealed lipid micropellets and characterization of their surface morphology" Pharm. Res. 8:47-54 (1991).
Srour et al. "Regulation of human factor IX expression using doxycycline-inducible gene expression system" Thromb Haemost 90:398-405 (2003).
Studier F.W. et al "Use of T7 RNA Polymerase to Direct Expression of Cloned Genes" Methods in Enzymol. 185:60-89 (1990).
Su et al. "Curcumin Inhibits Human Lung Cell Carcinoma Cancer Tumour Growth in a Murine Xenograft Model" (Phytother. Res. 24:189-191, 2010).
Takamatsu et al. "Expression of bacterial chloramphenicol acetyltransferase gene in tobacco plants mediated by TMV-RNA" EMBO J 6:307-311 (1987).
Treat et al., in "Liposomes in the therapy of infectious diseases and cancer." 353-365 (1989).
Uenalp et al. "Factor VII deficiency associated with valproate treatment" Pediatrics International 50(3):403-405 Abstract (2008).
Weiss et al. "Noncompliance in Neurologic Patients" Current Treatment Options in Neurology 7:419-425 (2005).
Wells, J.A, "Additivity of Mutational Effects in Proteins" Biochemistry 29:8509-8517 (1990).
White et al. "Mammalian Recombinant Coagulation Proteins: Structure and Function", Transfus. Sci. (1998) 19(2):177-189.
Winoto et al. "A novel, inducible and T cell-specific enhancer located at the 3' end of the T cell receptor alpha locus" EMBO J. 8:729-733 (1989).
Yefenof & McConnell "Interferon amplifies complement activation by Burkitt's lymphoma cells" Nature. Feb. 21-27, 1985;313(6004):68.
Yin et al. "Recombinant human growth hormone replacement therapy in HIV-associated wasting and visceral adiposity". Exper. Rev. Anti-Infect. Ther. 3(5):727-736 (2005).
Zhong et al. "The N-terminal epidermal growth factor-like domain in factor IX and factor X represents an important recognition motif for binding to tissue factor" J. Biol. Chem. (2002) 277(5):3622-31.
Ameredes et al. "Growth Hormone Improves Body Mass Recovery with Refeeding after Chronic Undernutrition-Induced Muscle Atrophy in Aging Male Rats" Journal of Nutrition. 129:2264-2270 (1999).
Askoy et al., "A study of the intracellular and secreted forms of the MUC2 mucin from the PC/AA intestinal cell line." Glycobiology 9.7: 739-746 (1999).
Beeley, Glycoprotein and proteoglycan techniques. Elsevier: 69-72 (1985).
Butler et al., "The beta-subunit of human chorionic gonadotrophin exists as a homodimer." Journal of Molecular Endocrinology 22.2: 185-192 (1999).
Cawley et al. "Developing long-acting growth hormone formulations", Clin Endocrinol (OXF). Sep. 2013;79(3):305-9.
Chan et al. "Plasma Insulin-Like Growth Factor-I and Prostate Cancer Risk: A Prospective Study", Science vol. 279:563-566, Jan. 1998.
Chen et al., "Recombinant carbohydrate variant of human choriogonadotropin beta-subunit (hCG beta) descarboxyl terminus (115-145). Expression and characterization of carboxyl-terminal deletion mutant of hCG beta in the baculovirus system." Journal of Biological Chemistry 266.10: 6246-6251 (1991).
Chen et al., "Glycoengineering Approach to Half-Life Extension of Recombinant Biotherapeutics." Bioconjugate Chemistry 23.8: 1524-1533 (2012).
Chen et al., "Modulating antibody pharmacokinetics using hydrophilic polymers." Expert Opinion on Drug Delivery 8.9: 1221-1236 (2011).
Diness, et al. Lund-Hansen, and U. Hedner. "Effect of recombinant human FVIIA on warfarin-induced bleeding in rats." Thrombosis research 59.6 (1990): 921-929.
Eschbach et al. "Correction of the Anemia of End-Stage Renal Disease with Recombinant Human Erythropoietin", N Engl J Med. Jan. 8, 1987;316(2):73-8.
Fares, "The role of O-linked and N-linked oligosaccharides on the structure-function of glycoprotein hormones: development of agonists and antagonists", Biochimica et Biophysica Acta (BBA)-General Subjects 1760.4: 560-567 (2006).
Garcia-Campayo et al., "Unmasking a new recognition signal for O-linked glycosylation in the chorionic gonadotropin β subunit." Molecular and Cellular Endocrinology 194.1: 63-70 (2002).
Gilboa et al., "Transfer and Expression of Cloned Genes Using Retroviral Vectors", Biotechniques, vol. 4:504-512, (1986).
Guitton et al., "Influence of in vitro non-enzymatic glycosylation on the physicochemical parameters of type I collagen." Collagen and Related Research 4.4: 253-264 (1984).
Kanda et al. "Genetic fusion of an alpha-subunit gene to the follicle-stimulating hormone and chorionic gonadotropin-beta subunit genes: production of a bifunctional protein", Mol Endocrinol. Nov. 1999;13(11):1873-81.
Kessler et al., "Structures of N-Glycosidic Carbohydrate Units of Human Chorionic Gonadotropin" J Biol Chem. Aug. 25, 1979;254(16):7901-8.
Kicman et al., "Human chorionic gonadotrophin and sport." British Journal of Sports Medicine 25.2 : 73-80 (1991).
Knudsen et al. "Small-molecule agonists for the glucagon-like peptide 1 receptor", PNAS, Jan. 16, 2007, vol. 104, No. 3, 937-942.
Kontermann, "Half-Life Modulating Strategies—An Introduction." Therapeutic Proteins: Strategies to Modulate Their Plasma Half-Lives : 1-21 (2012).
Kontermann, "Strategies for extended serum half-life of protein therapeutics." Current opinion in Biotechnology 22.6: 868-876 (2011).
Larsen et al., "Accumulation of magnetic iron oxide nanoparticles coated with variably sized polyethylene glycol in murine tumors." Nanoscale 4.7: 2352-2361 (2012).
Lentz et al., "Posttranslational modification of the carboxy-terminal region of the. beta. subunit of human chorionic gonadotropin." Biochemistry 23.22: 5330-5337 (1984).
Lopez-Berestein et al. "Treatment of systemic fungal infections with liposomal amphotericin B", Arch Intern Med. Nov. 1989;149(11):2533-6.
Lopez-Berestein, Gabriel, and Isaiah J. Fidler. "Treatment of systemic fungal infections with liposomal amphotericin B." Liposomes in the therapy of infectious diseases and cancer. (1989): 317-327.
Maheshwari et al., "Manipulation of Electrostatic and Saccharide Linker Interactions in the Design of Efficient Glycopolypeptide-Based Cholera Toxin Inhibitors." Macromolecular bioscience 10.1: 68-81 (2010).
McAlister et al. "NMR analysis of the N-terminal SRCR domain of human CD5: engineering of a glycoprotein for superior characteristics in NMR experiments." Protein Engineering 11.10: 847-853 (1998).

(56) References Cited

OTHER PUBLICATIONS

Muleo et al. Small doses of recombinant factor VIIa in acquired deficiencies of vitamin K dependent factors. Blood Coagulation & Fibrinolysis Abstract, 10(8), 521-522 (1999).
Murray et al. "Dose titration and patient selection increases the efficacy of GH replacement in severely GH deficient adults", Clinical Endocrinology (1999) 50, pp. 749-757.
Mutter et al. "A New Base Labile Anchoring Group for Polymer Supported Peptide Synthesis." Helvetica chimica acta 67.7 (1984): 2009-2016.
Mutter et al. "Evolution versus design: template-directed self-assembly of peptides to artificial proteins (TASP)." CHIMIA International Journal for Chemistry 54.10 (2000): 552-557.
NCBI GenBank Accession No. AAL69702 (Apr. 3, 2002).
Ogle et al. "Renal effects of growth hormone. I. Renal function and kidney growth", Pediatr. Nephrol. vol. 6:394-398, 1992.
Pedrosa et al., "Selective neoglycosylation increases the structural stability of vicilin, the 7S storage globulin from pea seeds." Archives of Biochemistry and Biophysics 382.2: 203-210 (2000).
Persson et al., "Rational design of coagulation factor VIIa variants with substantially increased intrinsic activity." Proceedings of the National Academy of Sciences 98.24: 13583-13588 (2001).
Pierce et al., "Glycoprotein hormones: structure and function." Annual review of biochemistry 50.1: 465-495 (1981).
Polizzotti et al., "Effects of saccharide spacing and chain extension on toxin inhibition by glycopolypeptides of well-defined architecture." Macromolecules 40.20: 7103-7110 (2007).
Poreddy et al., "Exogenous fluorescent tracer agents based on pegylated pyrazine dyes for real-time point-of-care measurement of glomerular filtration rate." Bioorganic & Medicinal Chemistry 20.8: 2490-2497 (2012).
Puett et al. Structure-Function relationships of the luteinizing hormone receptor Ann. NY Acad. Sci. 1061: 41-54, 2005.
Rebois et al., "Hydrodynamic properties of the gonadotropin receptor from a murine Leydig tumor cell line are altered by desensitization." Biochemistry 26.20: 6422-6428 (1987).
Reichel, "SARCOSYL-PAGE: A new electrophoretic method for the separation and immunological detection of PEGylated proteins." Protein Electrophoresis. Humana Press 65-79 (2012).
Runge et al. "Different domains of the glucagon and glucagon-like peptide-1 receptors provide the critical determinants of ligand selectivity", British Journal of Pharmacology (2003) 138, 787-794.
Sambrook, Joseph et al. "Molecular cloning: a laboratory manual." Cold Spring Harbor Laboratory Press, Cold Spring Harbor, New York 2 (2001).
Sugahara et al., "Characterization of the O-glycosylation sites in the chorionic gonadotropin β subunit in vivo using site-directed mutagenesis and gene transfer." Journal of Biological Chemistry 271.34: 20797-20804 (1996).
Tape et al. "Apolipoprotein A-I and apolipoprotein SAA half-lives during acute inflammation and amyloidogenesis", Biochimica et Biophysica Acta (lipid and lipid metabolism) 1043: 295-300, 1990.
Venn et al., "Biosynthesis and metabolism in vivo of intervertebral-disc proteoglycans in the mouse." Biochem. J 215: 217-225 (1983).
Weissbach & Weissbach, 1988, Methods for Plant Molecular Biology, Academic Press, NY, Section VIII, pp. 421-463.
Wildt et al., "The humanization of N-glycosylation pathways in yeast." Nature Reviews Microbiology 3.2: 119-128 (2005).
Wilken et al., "A novel four-amino acid determinant defines conformational freedom within chorionic gonadotropin β-subunits." Biochemistry 46.14: 4417-4424 (2007).
Wynne, Katie, et al. "Subcutaneous oxyntomodulin reduces body weight in overweight and obese subjects a double-blind, randomized, controlled trial." Diabetes 54.8 (2005): 2390-2395.
Zheng et al., "The impact of glycosylation on monoclonal antibody conformation and stability." MAbs. vol. 3. No. 6. Landes Bioscience (Nov.-Dec. 2011), pp. 568-576.

Biller et al. "Effects of once-weekly sustained-release growth hormone: a double-blind, placebo-controlled study in adult growth hormone deficiency", J Clin Endocrinol Metab. Jun. 2011;96(6):1718-26.
Bouloux et al. "First human exposure to FSH-CTP in hypogonadotrophic hypogonadal males." Human Reproduction 16.8 (2001): 1592-1597.
Carles-Bonnet et al. "H-Lys-Arg-Asn-Lys-Asn-Asn-OH is the minimal active structure of oxyntomodulin." Peptides 17.3 (1996): 557-561.
Chihara et al. "Clinical aspect of growth hormone deficiency in adults", Nihon Naika Gakkai Zasshi. Sep. 10, 2000;89(9):2010-8; with English Abstract.
Dalton et al. "Over-expression of secreted proteins from mammalian cell lines", Protein Sci. May 2014;23(5):517-25.
Fogarty, Patrick F. "Biological rationale for new drugs in the bleeding disorders pipeline." ASH Education Program Book 2011.1 (2011): 397-404.
Jarrousse et al. "Oxyntomodulin (glucagon-37) and its C-terminal octapeptide inhibit gastric acid secretion", FEBS Lett. Aug. 19, 1985; 188(1): 81-4.
Morgan et al. "The amino acid sequence of human chorionic gonadotropin. The alpha subunit and beta subunit", J Biol Chem. Jul. 10, 1975;250(13):5247-58.
Nezu et al. "Treatment of idiopathic pituitary dwarfism with human growth hormone", Journal of Nara Medical Association 1989, vol. 40, No. 1, p. 16-22; with English Abstract.
Office Action for Japanese Application No. 2014-523441 dated May 24, 2016.
Supplementary European Search Report for European Application No. 13749077.7 dated Oct. 22, 2015.
Alberts et al. "Molecular biology of the cell", 5th ed.(Garland Science, 2008). 2002, p. 367.
Anonymous "Prolor Biotech Receives New U.S. Patent Allowance Covering Broad Applications of its CTP Platform for Long Acting Therapeutic Proteins", Jul. 11, 2011, pp. 1-2; Retrieved from the Internet: URL;http://web.archive.org/web/20110725053527/http://www.prolor-biotech.com/_Uploads/dbsAttachedFiles/NewsPROLORAnnouncesAllowanceOfNewCTPPlatformPatentByUSPatentOffice.pdf.
Anonymous "Corporate Presentation", Jun. 1, 2011, pp. 1-35; Retrieved from the Internet: URL;http://web.archive.org/web/20110628023057/http://www.prolor-biotech.com/_Uploads/dbsAttachedFiles/prolorPresentationJune2011Investors.pdf.
Anonymous "PROLOR and Yeda enter definitive license agreement for Reversible PEGylation technology", Jan. 18, 2011, pp. 1-3; Retrieved from the Internet: URL;http://web.archive.org/web/20110123063420/http://www.news-medical.net/news/20110118/PROLOR-and-Yeda-enter-definitive-license-agreement-for-Reversible-PEGylation-technology.aspx.
Cohen et al. "Oxyntomodulin suppresses appetite and reduces food intake in humans", J Clin Endocrinol Metab. Oct. 2003;88(10):4696-701.
Edmunds et al. "Plasma erythropoietin levels and acquired cystic disease of the kidney in patients receiving regular haemodialysis treatment" Br J Haematol. Jun. 1991;78(2):275-7.
Kieffer et al. "Distribution of glucagon receptors on hormone-specific endocrine cells of rat pancreatic islets" Endocrinology. Nov. 1996;137(11):5119-25.
Krantz et al. "Specific binding of erythropoietin to spleen cells infected with the anemia strain of Friend virus" Proc Natl Acad Sci U S A. Dec. 1984;81(23):7574-8.
Littlewood, T.J. "Erythropoietin for the treatment of anemia associated with hematological malignancy" Hematol Oncol. Mar. 2001;19(1):19-30.
Musto "The role of recombinant erythropoietin for the treatment of anemia in multiple myeloma" Leuk Lymphoma. Apr. 1998;29(3-4):283-91.
Pocai et al. "Glucagon-Like Peptide 1/Glucagon Receptor Dual Agonism Reverses Obesity in Mice", Diabetes, vol. 58, Oct. 2009, pp. 2258-2266.
Schneider KH "GMP Requirements for master and working cell bank" Pharmazeutische Industrie. Jan. 1, 2005;67(11):1366-9.

(56) References Cited

OTHER PUBLICATIONS

Shechter et al. "Reversible PEGylation of peptide YY3-36 prolongs its inhibition of food intake in mice", FEBS Lett. Apr. 25, 2005;579(11):2439-44.
Stuart et al. "Polycythemia Vera" Am Fam Physician. May 1, 2004;69(9):2139-44.
Takeya et al. "Bovine factor VII. Its purification and complete amino acid sequence". Journal of Biological Chemistry. Oct. 15, 1988;263(29):14868-77.
Tharakan et al. "Emerging therapies in the treatment of 'diabesity': beyond GLP-1" Trends Pharmacol Sci. Jan. 2011;32(1):8-15.
Verhoef et al. "Recombinant human erythropoietin for the treatment of anemia in the myelodysplastic syndromes: a clinical and erythrokinetic assessment" Ann Hematol. Jan. 1992;64(1):16-21.
Diao et al. "The molecular design and drug development of recombinant long-acting follicle stimulating hormone" Acta pharmaceutica Sinica. Apr. 2012;47(4):421-6; Abstract.
European Search Report for European Application No. 17161199.9 dated Aug. 7, 2017.
European Search Report for European Patent Application No. 18150731.0 dated Feb. 27, 2018.
International Search Report for Application No. PCT/IL2017/050645 dated Sep. 21, 2017.
International Search Report for Application No. PCT/IL2017/050784 dated Sep. 22, 2017.
Wilson et al. "Assessing annotation transfer for genomics: quantifying the relations between protein sequence, structure and function through traditional and probabilistic scores" Journal of molecular biology. Mar. 17, 2000;297(1):233-49.
Zhong et al. "Biological insights into therapeutic protein modifications throughout trafficking and their biophaffnaceutical applications" International journal of cell biology. Apr. 18, 2013;2013.
McNeil C. "No rest for fatigue researchers. Journal of the National Cancer Institute" Aug. 20, 2008;100(16):1129.
Morel L. "Mouse models of human autoimmune diseases: essential tools that require the proper controls" PLoS biology. Aug. 17, 2004;2(8):e241.
Riddik et al. "A stepwise increase in recombinant human growth hormone dosing during puberty achieves improved pubertal growth: a National Cooperative Growth Study report" Journal of Pediatric Endocrinology and Metabolism. 2009;22(7):623-8.

\* cited by examiner

SEQUENCE LISTING

<160> NUMBER OF SEQ ID NOS: 26

<210> SEQ ID NO 1
<211> LENGTH: 33
<212> TYPE: PRT
<213> ORGANISM: Homo sapiens

<400> SEQUENCE: 1

Asp Pro Arg Phe Gln Asp Ser Ser Ser Lys Ala Pro Pro Ser
1               5                   10                  15

Leu Pro Ser Pro Ser Arg Leu Pro Gly Pro Ser Asp Thr Pro Ile Leu
            20                  25                  30

Gln

<210> SEQ ID NO 2
<211> LENGTH: 28
<212> TYPE: PRT
<213> ORGANISM: Homo sapiens

<400> SEQUENCE: 2

Ser Ser Ser Ser Lys Ala Pro Pro Ser Leu Pro Ser Pro Ser Arg
1               5                   10                  15

Leu Pro Gly Pro Ser Asp Thr Pro Ile Leu Pro Gln
            20                  25

<210> SEQ ID NO 3
<211> LENGTH: 26
<212> TYPE: PRT
<213> ORGANISM: Homo sapiens

<400> SEQUENCE: 3

Met Ala Thr Gly Ser Arg Thr Ser Leu Leu Leu Ala Phe Gly Leu Leu
1               5                   10                  15

Cys Leu Pro Trp Leu Gln Glu Gly Ser Ala
            20                  25

<210> SEQ ID NO 4
<211> LENGTH: 12
<212> TYPE: PRT
<213> ORGANISM: Homo sapiens

<400> SEQUENCE: 4

Ser Ser Ser Ser Lys Ala Pro Pro Ser Leu Pro
1               5                   10

<210> SEQ ID NO 5
<211> LENGTH: 217
<212> TYPE: PRT
<213> ORGANISM: Homo sapiens

<400> SEQUENCE: 5

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

```
Leu Glu Pro Val Gln Phe Leu Arg Ser Val Phe Ala Asn Ser Leu Val
                115                 120                 125

Tyr Gly Ala Ser Asp Ser Asn Val Tyr Asp Leu Leu Lys Asp Leu Glu
            130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
            195                 200                 205

Arg Ser Val Glu Gly Ser Cys Gly Phe
    210                 215

<210> SEQ ID NO 6
<211> LENGTH: 192
<212> TYPE: PRT
<213> ORGANISM: Homo sapiens

<400> SEQUENCE: 6

Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Asp Gly Ser Pro Arg Thr Gly Gln Ile Phe Lys Gln Thr Tyr
    130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190

<210> SEQ ID NO 7
<211> LENGTH: 25
<212> TYPE: PRT
<213> ORGANISM: Homo sapiens

<400> SEQUENCE: 7

Met Phe Pro Thr Ile Pro Leu Ser Arg Leu Phe Asp Asn Ala Met Leu
1               5                   10                  15

Arg Ala His Arg Leu His Gln Leu Ala
            20                  25
```

<210> SEQ ID NO 8
<211> LENGTH: 217
<212> TYPE: PRT
<213> ORGANISM: Homo sapiens

<400> SEQUENCE: 8

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Val Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
    210                 215
```

<210> SEQ ID NO 9
<211> LENGTH: 245
<212> TYPE: PRT
<213> ORGANISM: Homo sapiens

<400> SEQUENCE: 9

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110
```

```
Leu Glu Pro Val Gln Phe Leu Arg Ser Val Phe Ala Asn Ser Leu Val
            115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Ser Ser Ser Lys Ala Pro
    210                 215                 220

Pro Pro Ser Leu Pro Ser Pro Ser Arg Leu Pro Gly Pro Ser Asp Thr
225                 230                 235                 240

Pro Ile Leu Pro Gln
            245

<210> SEQ ID NO 10
<211> LENGTH: 273
<212> TYPE: PRT
<213> ORGANISM: Homo sapiens

<400> SEQUENCE: 10

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Ser Ser Ser Lys Ala Pro
    210                 215                 220

Pro Pro Ser Leu Pro Ser Pro Ser Arg Leu Pro Gly Pro Ser Asp Thr
225                 230                 235                 240
```

```
Pro Ile Leu Pro Gln Ser Ser Ser Lys Ala Pro Pro Ser Leu
            245                 250                 255

Pro Ser Pro Ser Arg Leu Pro Gly Pro Ser Asp Thr Pro Ile Leu Pro
            260                 265                 270

Gln

<210> SEQ ID NO 11
<211> LENGTH: 301
<212> TYPE: PRT
<213> ORGANISM: Homo sapiens

<400> SEQUENCE: 11

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Ser Ser Lys Ala
            20                  25                  30

Pro Pro Pro Ser Leu Pro Ser Pro Ser Arg Leu Pro Gly Pro Ser Asp
            35                  40                  45

Thr Pro Ile Leu Pro Gln Phe Pro Thr Ile Pro Leu Ser Arg Leu Phe
50                  55                  60

Asp Asn Ala Met Leu Arg Ala His Arg Leu His Gln Leu Ala Phe Asp
65                  70                  75                  80

Thr Tyr Gln Glu Phe Glu Glu Ala Tyr Ile Pro Lys Glu Gln Lys Tyr
                85                  90                  95

Ser Phe Leu Gln Asn Pro Gln Thr Ser Leu Cys Phe Ser Glu Ser Ile
            100                 105                 110

Pro Thr Pro Ser Asn Arg Glu Glu Thr Gln Gln Lys Ser Asn Leu Glu
            115                 120                 125

Leu Leu Arg Ile Ser Leu Leu Leu Ile Gln Ser Trp Leu Glu Pro Val
130                 135                 140

Gln Phe Leu Arg Ser Val Phe Ala Asn Ser Leu Val Tyr Gly Ala Ser
145                 150                 155                 160

Asp Ser Asn Val Tyr Asp Leu Leu Lys Asp Leu Glu Glu Gly Ile Gln
                165                 170                 175

Thr Leu Met Gly Arg Leu Glu Asp Gly Ser Pro Arg Thr Gly Gln Ile
            180                 185                 190

Phe Lys Gln Thr Tyr Ser Lys Phe Asp Thr Asn Ser His Asn Asp Asp
            195                 200                 205

Ala Leu Leu Lys Asn Tyr Gly Leu Leu Tyr Cys Phe Arg Lys Asp Met
210                 215                 220

Asp Lys Val Glu Thr Phe Leu Arg Ile Val Gln Cys Arg Ser Val Glu
225                 230                 235                 240

Gly Ser Cys Gly Phe Ser Ser Ser Lys Ala Pro Pro Pro Ser Leu
                245                 250                 255

Pro Ser Pro Ser Arg Leu Pro Gly Pro Ser Asp Thr Pro Ile Leu Pro
            260                 265                 270

Gln Ser Ser Ser Ser Lys Ala Pro Pro Pro Ser Leu Pro Ser Pro Ser
            275                 280                 285

Arg Leu Pro Gly Pro Ser Asp Thr Pro Ile Leu Pro Gln
            290                 295                 300

<210> SEQ ID NO 12
<211> LENGTH: 285
<212> TYPE: PRT
<213> ORGANISM: Homo sapiens
```

<400> SEQUENCE: 12

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Ser Ser Ser Lys Ala
            20                  25                  30

Pro Pro Pro Ser Leu Pro Phe Pro Thr Ile Pro Leu Ser Arg Leu Phe
        35                  40                  45

Asp Asn Ala Met Leu Arg Ala His Arg Leu His Gln Leu Ala Phe Asp
    50                  55                  60

Thr Tyr Gln Glu Phe Glu Glu Ala Tyr Ile Pro Lys Glu Gln Lys Tyr
65                  70                  75                  80

Ser Phe Leu Gln Asn Pro Gln Thr Ser Leu Cys Phe Ser Glu Ser Ile
                85                  90                  95

Pro Thr Pro Ser Asn Arg Glu Glu Thr Gln Gln Lys Ser Asn Leu Glu
            100                 105                 110

Leu Leu Arg Ile Ser Leu Leu Leu Ile Gln Ser Trp Leu Glu Pro Val
        115                 120                 125

Gln Phe Leu Arg Ser Val Phe Ala Asn Ser Leu Val Tyr Gly Ala Ser
    130                 135                 140

Asp Ser Asn Val Tyr Asp Leu Leu Lys Asp Leu Glu Glu Gly Ile Gln
145                 150                 155                 160

Thr Leu Met Gly Arg Leu Glu Asp Gly Ser Pro Arg Thr Gly Gln Ile
                165                 170                 175

Phe Lys Gln Thr Tyr Ser Lys Phe Asp Thr Asn Ser His Asn Asp Asp
            180                 185                 190

Ala Leu Leu Lys Asn Tyr Gly Leu Leu Tyr Cys Phe Arg Lys Asp Met
        195                 200                 205

Asp Lys Val Glu Thr Phe Leu Arg Ile Val Gln Cys Arg Ser Val Glu
    210                 215                 220

Gly Ser Cys Gly Phe Ser Ser Ser Lys Ala Pro Pro Pro Ser Leu
225                 230                 235                 240

Pro Ser Pro Ser Arg Leu Pro Gly Pro Ser Asp Thr Pro Ile Leu Pro
                245                 250                 255

Gln Ser Ser Ser Ser Lys Ala Pro Pro Pro Ser Leu Pro Ser Pro Ser
            260                 265                 270

Arg Leu Pro Gly Pro Ser Asp Thr Pro Ile Leu Pro Gln
        275                 280                 285
```

<210> SEQ ID NO 13
<211> LENGTH: 273
<212> TYPE: PRT
<213> ORGANISM: Homo sapiens

<400> SEQUENCE: 13

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Ser Ser Ser Lys Ala
            20                  25                  30

Pro Pro Pro Ser Leu Pro Ser Pro Ser Arg Leu Pro Gly Pro Ser Asp
        35                  40                  45

Thr Pro Ile Leu Pro Gln Phe Pro Thr Ile Pro Leu Ser Arg Leu Phe
    50                  55                  60

Asp Asn Ala Met Leu Arg Ala His Arg Leu His Gln Leu Ala Phe Asp
65                  70                  75                  80
```

Thr Tyr Gln Glu Phe Glu Glu Ala Tyr Ile Pro Lys Glu Gln Lys Tyr
                85                  90                  95

Ser Phe Leu Gln Asn Pro Gln Thr Ser Leu Cys Phe Ser Glu Ser Ile
                100                 105                 110

Pro Thr Pro Ser Asn Arg Glu Glu Thr Gln Gln Lys Ser Asn Leu Glu
            115                 120                 125

Leu Leu Arg Ile Ser Leu Leu Leu Ile Gln Ser Trp Leu Glu Pro Val
        130                 135                 140

Gln Phe Leu Arg Ser Val Phe Ala Asn Ser Leu Val Tyr Gly Ala Ser
145                 150                 155                 160

Asp Ser Asn Val Tyr Asp Leu Leu Lys Asp Leu Glu Glu Gly Ile Gln
                165                 170                 175

Thr Leu Met Gly Arg Leu Glu Asp Gly Ser Pro Arg Thr Gly Gln Ile
            180                 185                 190

Phe Lys Gln Thr Tyr Ser Lys Phe Asp Thr Asn Ser His Asn Asp Asp
        195                 200                 205

Ala Leu Leu Lys Asn Tyr Gly Leu Leu Tyr Cys Phe Arg Lys Asp Met
210                 215                 220

Asp Lys Val Glu Thr Phe Leu Arg Ile Val Gln Cys Arg Ser Val Glu
225                 230                 235                 240

Gly Ser Cys Gly Phe Ser Ser Ser Lys Ala Pro Pro Ser Leu
                245                 250                 255

Pro Ser Pro Ser Arg Leu Pro Gly Pro Ser Asp Thr Pro Ile Leu Pro
            260                 265                 270

Gln

<210> SEQ ID NO 14
<211> LENGTH: 245
<212> TYPE: PRT
<213> ORGANISM: Homo sapiens

<400> SEQUENCE: 14

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Ser Ser Lys Ala
                20                  25                  30

Pro Pro Pro Ser Leu Pro Ser Pro Ser Arg Leu Pro Gly Pro Ser Asp
            35                  40                  45

Thr Pro Ile Leu Pro Gln Phe Pro Thr Ile Pro Leu Ser Arg Leu Phe
        50                  55                  60

Asp Asn Ala Met Leu Arg Ala His Arg Leu His Gln Leu Ala Phe Asp
65                  70                  75                  80

Thr Tyr Gln Glu Phe Glu Glu Ala Tyr Ile Pro Lys Glu Gln Lys Tyr
                85                  90                  95

Ser Phe Leu Gln Asn Pro Gln Thr Ser Leu Cys Phe Ser Glu Ser Ile
                100                 105                 110

Pro Thr Pro Ser Asn Arg Glu Glu Thr Gln Gln Lys Ser Asn Leu Glu
            115                 120                 125

Leu Leu Arg Ile Ser Leu Leu Leu Ile Gln Ser Trp Leu Glu Pro Val
        130                 135                 140

Gln Phe Leu Arg Ser Val Phe Ala Asn Ser Leu Val Tyr Gly Ala Ser
145                 150                 155                 160

Asp Ser Asn Val Tyr Asp Leu Leu Lys Asp Leu Glu Glu Gly Ile Gln
                165                 170                 175

```
Thr Leu Met Gly Arg Leu Glu Asp Gly Ser Pro Arg Thr Gly Gln Ile
            180                 185                 190

Phe Lys Gln Thr Tyr Ser Lys Phe Asp Thr Asn Ser His Asn Asp Asp
        195                 200                 205

Ala Leu Leu Lys Asn Tyr Gly Leu Leu Tyr Cys Phe Arg Lys Asp Met
    210                 215                 220

Asp Lys Val Glu Thr Phe Leu Arg Ile Val Gln Cys Arg Ser Val Glu
225                 230                 235                 240

Gly Ser Cys Gly Phe
                245

<210> SEQ ID NO 15
<211> LENGTH: 853
<212> TYPE: DNA
<213> ORGANISM: Homo sapiens

<400> SEQUENCE: 15
tctagaggac atggccaccg gcagcaggac cagcctgctg ctggccttcg gcctgctgtg    60
cctgccatgg ctgcaggagg gcagcgccag ctcttcttct aaggctccac ccccatctct   120
gcccagcccc agcagactgc cgggcccag cgacacaccc attctgcccc agttccccac    180
catccccctg agcaggctgt tcgacaacgc catgctgagg gctcacaggc tgcaccagct   240
ggcctttgac acctaccagg agttcgagga agcctacatc cccaaggagc agaagtacag   300
cttcctgcag aaccccagaa cctccctgtg cttcagcgag agcatcccca ccccccagcaa   360 cagagaggag acccagcaga gagcaacct ggagctgctg aggatctccc tgctgctgat     420
ccagagctgg ctggagcccg tgcagttcct gagaagcgtg ttcgccaaca gcctggtgta   480
cggcgccagc gacagcaacg tgtacgacct gctgaaggac ctggaggagg catccagac    540 cctgatgggc cggctggagg acggcagccc caggaccggc cagatcttca gcagaccta    600 cagcaagttc gacaccaaca gccacaacga cgacgccctg ctgaagaact acggcctgct   660
gtactgcttc agaaaggaca tggacaaggt ggagaccttc ctgaggatcg tgcagtgcag   720
aagcgtggag ggcagctgcg gcttcagctc cagcagcaag gcccctcccc cgagcctgcc   780
ctccccaagc aggctgcctg gccctccga cacaccaatc ctgcctcagt gatgaaggtc    840
tggatgcggc cgc                                                      853

<210> SEQ ID NO 16
<211> LENGTH: 937
<212> TYPE: DNA
<213> ORGANISM: Homo sapiens

<400> SEQUENCE: 16
tctagaggac atggccaccg gcagcaggac cagcctgctg ctggccttcg gcctgctgtg    60
cctgccatgg ctgcaggagg gcagcgccag ctcttcttct aaggctccac ccccatctct   120
gcccagcccc agcagactgc cgggcccag cgacacaccc attctgcccc agttccccac    180
catccccctg agcaggctgt tcgacaacgc catgctgagg gctcacaggc tgcaccagct   240
ggcctttgac acctaccagg agttcgagga agcctacatc cccaaggagc agaagtacag   300
cttcctgcag aaccccagaa cctccctgtg cttcagcgag agcatcccca ccccccagcaa   360 cagagaggag acccagcaga gagcaacct ggagctgctg aggatctccc tgctgctgat     420
ccagagctgg ctggagcccg tgcagttcct gagaagcgtg ttcgccaaca gcctggtgta   480
cggcgccagc gacagcaacg tgtacgacct gctgaaggac ctggaggagg catccagac    540
```

```
cctgatgggc cggctggagg acggcagccc caggaccggc cagatcttca agcagaccta      600
cagcaagttc gacaccaaca gccacaacga cgacgccctg ctgaagaact acgggctgct      660
gtactgcttc agaaaggaca tggacaaggt ggagaccttc ctgaggatcg tgcagtgcag      720
aagcgtggag ggcagctgcg gcttcagctc cagcagcaag gcccctcccc cgagcctgcc      780
ctccccaagc aggctgcctg ggcctccga cacaccaatc ctgccacaga gcagctcctc       840
taaggcccct cctccatccc tgccatcccc ctcccggctg cctggcccct ctgacacccc      900
tatcctgcct cagtgatgaa ggtctggatg cggccgc                              937

<210> SEQ ID NO 17
<211> LENGTH: 889
<212> TYPE: DNA
<213> ORGANISM: Homo sapiens

<400> SEQUENCE: 17
tctagaggac atggccaccg gcagcaggac cagcctgctg ctggccttcg gcctgctgtg       60
cctgccatgg ctgcaggagg gcagcgccag ctcttcttct aaggctccac ccccgagcct      120
gcccttcccc accatccccc tgagcaggct gttcgacaac gccatgctga gggctcacag      180
gctgcaccag ctggcctttg acacctacca ggagttcgag gaagcctaca tccccaagga      240
gcagaagtac agcttcctgc agaaccccca gacctccctg tgcttcagcg agagcatccc      300
cacccccagc aacagagagg agacccagca gaaagcaac ctggagctgc tgaggatctc       360
cctgctgctg atccagagct ggctggagcc cgtgcagttc ctgagaagcg tgttcgccaa      420
cagcctggtg tacggcgcca gcgacagcaa cgtgtacgac ctgctgaagg acctggagga      480
gggcatccag accctgatgg gccggctgga ggacggcagc cccaggaccg gccagatctt      540
caagcagacc tacagcaagt tcgacaccaa cagccacaac gacgacgccc tgctgaagaa      600
ctacgggctg ctgtactgct tcagaaagga catggacaag gtggagacct tcctgaggat      660
cgtgcagtgc agaagcgtgg agggcagctg cggcttcagc tccagcagca aggcccctcc      720
cccgagcctg ccctccccaa gcaggctgcc tgggcctcc gacacaccaa tcctgccaca      780
gagcagctcc tctaaggccc ctcctccatc cctgccatcc cctcccggc tgcctggccc      840 ctctgacacc cctatcctgc ctcagtgatg aaggtctgga tgcggccgc                  889

<210> SEQ ID NO 18
<211> LENGTH: 19
<212> TYPE: DNA
<213> ORGANISM: Artificial Sequence
<220> FEATURE:
<223> OTHER INFORMATION: XbaI Forward primer for HGH-CTP constructs

<400> SEQUENCE: 18
ctctagagga catggccac                                                   19

<210> SEQ ID NO 19
<211> LENGTH: 24
<212> TYPE: DNA
<213> ORGANISM: Artificial Sequence
<220> FEATURE:
<223> OTHER INFORMATION: Reverse primer for HGH-CTP constructs

<400> SEQUENCE: 19
acagggaggt ctgggggttc tgca                                             24

<210> SEQ ID NO 20
```

```
<211> LENGTH: 26
<212> TYPE: DNA
<213> ORGANISM: Artificial Sequence
<220> FEATURE:
<223> OTHER INFORMATION: Forward primer for HGH-CTP constructs

<400> SEQUENCE: 20
tgcagaaccc ccagacctcc ctgtgc                                          26

<210> SEQ ID NO 21
<211> LENGTH: 22
<212> TYPE: DNA
<213> ORGANISM: Artificial Sequence
<220> FEATURE:
<223> OTHER INFORMATION: Reverse primer for HGH-CTP constructs

<400> SEQUENCE: 21
ccaaactcat caatgtatct ta                                              22

<210> SEQ ID NO 22
<211> LENGTH: 19
<212> TYPE: DNA
<213> ORGANISM: Artificial Sequence
<220> FEATURE:
<223> OTHER INFORMATION: XbaI Forward primer for HGH-CTP constructs

<400> SEQUENCE: 22
ctctagagga catggccac                                                  19

<210> SEQ ID NO 23
<211> LENGTH: 25
<212> TYPE: DNA
<213> ORGANISM: Artificial Sequence
<220> FEATURE:
<223> OTHER INFORMATION: Reverse primer for HGH-CTP constructs

<400> SEQUENCE: 23
cgaactcctg gtaggtgtca aaggc                                           25

<210> SEQ ID NO 24
<211> LENGTH: 25
<212> TYPE: DNA
<213> ORGANISM: Artificial Sequence
<220> FEATURE:
<223> OTHER INFORMATION: Forward primer for HGH-CTP constructs

<400> SEQUENCE: 24
gcctttgaca cctaccagga gttcg                                           25

<210> SEQ ID NO 25
<211> LENGTH: 33
<212> TYPE: DNA
<213> ORGANISM: Artificial Sequence
<220> FEATURE:
<223> OTHER INFORMATION: Reverse primer for HGH-CTP constructs

<400> SEQUENCE: 25
acgcggccgc atccagacct tcatcactga ggc                                  33

<210> SEQ ID NO 26
<211> LENGTH: 34
<212> TYPE: DNA
<213> ORGANISM: Artificial Sequence
<220> FEATURE:
<223> OTHER INFORMATION: Reverse primer for HGH-CTP constructs
```

```
<400> SEQUENCE: 26
gcggccgcgg actcatcaga agccgcagct gccc                34
```

METHODS OF TREATMENT WITH LONG-ACTING GROWTH HORMONE

CROSS REFERENCE TO RELATED APPLICATIONS

This application is a National Phase Application of PCT International Application No. PCT/IL2012/050288, filed Aug. 2, 2012, which claims priority to U.S. application Ser. No. 13/195,931, now U.S. Pat. No. 8,450,269, filed on Aug. 2, 2011, which is hereby incorporated by reference in its entirety herein.

FIELD OF INVENTION

Use of a growth hormone protein and polynucleotides encoding same comprising an amino-terminal carboxy-terminal peptide (CTP) of chorionic gonadotrophin and two carboxy-terminal chorionic gonadotrophin CTPs attached to the growth hormone in methods of inducing weight loss or body fat reduction, method of increasing insulin-like growth factor (IGF-1) levels, and methods of reducing the dosing frequency of a growth hormone in a human subject are disclosed. Pharmaceutical compositions comprising the growth hormone and polynucleotides encoding the growth hormone of the invention and methods of using same are also disclosed.

BACKGROUND OF THE INVENTION

Polypeptides are susceptible to denaturation or enzymatic degradation in the blood, liver or kidney. Accordingly, polypeptides typically have short circulatory half-lives of several hours. Because of their low stability, peptide drugs are usually delivered in a sustained frequency so as to maintain an effective plasma concentration of the active peptide. Moreover, since peptide drugs are usually administrated by infusion, frequent injection of peptide drugs cause considerable discomfort to a subject. Thus, there is a need for technologies that will prolong the half-lives of therapeutic polypeptides while maintaining a high pharmacological efficacy thereof. Such desired peptide drugs should also meet the requirements of enhanced serum stability, high activity and a low probability of inducing an undesired immune response when injected into a subject.

Unfavorable pharmacokinetics, such as a short serum half-life, can prevent the pharmaceutical development of many otherwise promising drug candidates. Serum half-life is an empirical characteristic of a molecule, and must be determined experimentally for each new potential drug. For example, with lower molecular weight polypeptide drugs, physiological clearance mechanisms such as renal filtration can make the maintenance of therapeutic levels of a drug unfeasible because of cost or frequency of the required dosing regimen. Conversely, a long serum half-life is undesirable where a drug or its metabolites has toxic side effects.

SUMMARY OF THE INVENTION

In one embodiment, the present invention provides a method of inducing weight loss or decreasing body fat in a human subject, comprising administering to the subject a therapeutically effective amount of a polypeptide comprising a growth hormone, one chorionic gonadotrophin carboxy terminal peptide (CTP) attached to the amino terminus of the growth hormone, and two chorionic gonadotrophin CTPs attached to the carboxy terminus of the growth hormone, thereby inducing weight loss or decreasing body fat in said subject.

In another embodiment, the present invention provides a method of increasing insulin-like growth factor (IGF-1) levels in a human subject, comprising administering to the subject a therapeutically effective amount of a polypeptide comprising a growth hormone, one chorionic gonadotrophin carboxy terminal peptide (CTP) attached to the amino terminus of the growth hormone, and two chorionic gonadotrophin CTPs attached to the carboxy terminus of the growth hormone, thereby increasing IGF-1 levels in said subject.

In one embodiment, the present invention provides a method of maintaining insulin-like growth factor (IGF-1) levels within a normal therapeutic range in a subject, the method comprising administering to the subject a therapeutically effective amount of a polypeptide comprising a growth hormone, one chorionic gonadotrophin carboxy terminal peptide (CTP) attached to the amino terminus of said growth hormone, and two chorionic gonadotrophin CTPs attached to the carboxy terminus of the growth hormone, thereby maintaining IGF-I within a normal therapeutic range in the subject.

In another embodiment, the present invention provides a method of reducing the dosing frequency of a growth hormone in a human subject, comprising the step of attaching one chorionic gonadotrophin carboxy terminal peptide (CTP) to the amino terminus of said growth hormone and two chorionic gonadotrophin CTPs to the carboxy terminus of the growth hormone, thereby reducing the dosing frequency of a growth hormone.

In one embodiment, the present invention provides a method of inducing growth or weight gain in a human subject, comprising administering to said subject a therapeutically effective amount of a polypeptide comprising a growth hormone, one chorionic gonadotrophin carboxy terminal peptide (CTP) attached to the amino terminus of said growth hormone, and two chorionic gonadotrophin CTPs attached to the carboxy terminus of said growth hormone, wherein the subject is a child or adolescent, thereby inducing growth or weight gain in said subject.

DETAILED DESCRIPTION OF THE INVENTION

Figure 1:
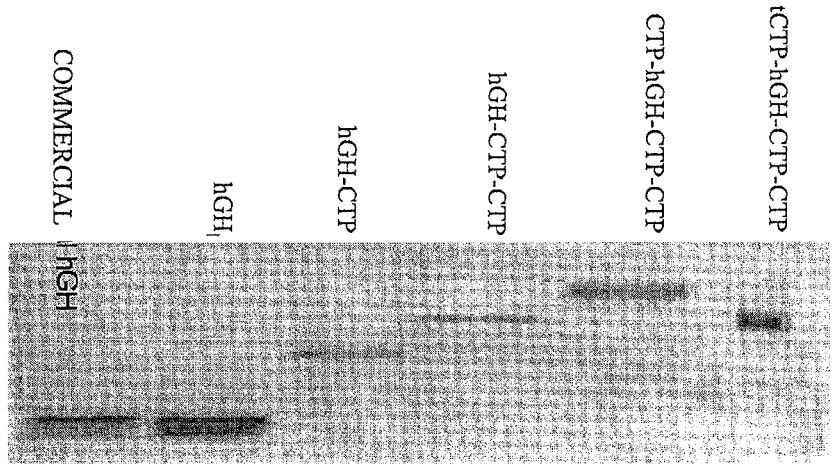
FIG. 1 is a Western blot illustrating the molecular weight & identity of hGH (SEQ ID NO: 5), hGH-CTP (SEQ ID NO: 9), hGH-CTP-CTP (SEQ ID NO: 10), CTP-hGH-CTP-CTP (SEQ ID NO: 11) and tCTP-hGH-CTP-CTP (SEQ ID NO: 12). PAGE SDS gel was blotted and stained using monoclonal anti-hGH antibodies. The photograph indicates that like commercial and wild type hGH, CTP-modified hGH variants are recognized by anti-hGH antibodies.

In one embodiment, the present invention provides long-acting growth hormones and methods of producing and using same. In another embodiment, long-acting growth hormones comprise carboxy terminal peptide (CTP, also referred to as CTP unit). In another embodiment, long-acting polypeptides comprise carboxy terminal peptide (CTP) of human Chorionic Gonadotropin (hCG). In another embodiment, CTP acts as a protectant against degradation of growth hormone or polypeptides of interest. In another embodiment, CTP extends the Cmax of growth hormones or polypeptides of interest. In another embodiment, CTP extends the Tmax of growth hormones or polypeptides of interest. In another embodiment, CTP extends circulatory half-lives of growth hormones or polypeptides of interest. In some embodiments, CTP enhances the potency of growth hormones or polypeptides of interest.

In other embodiments, engineered growth hormones or polypeptides of interest of the invention comprising a single CTP attached to the amino terminus and two CTP peptides attached in tandem to the carboxy terminus are at least equivalent to the non CTP modified growth hormones or polypeptides of interest, in terms of biological activity. In other embodiments, engineered growth hormones or polypeptides of interest of the invention comprising a single CTP attached to the amino terminus and two CTP peptides attached in tandem to the carboxy terminus are at least equivalent to the non CTP modified growth hormones or polypeptides of interest, in terms of pharmacological measures such as pharmacokinetics and pharmacodynamics.

In another embodiment, the present invention provides a polypeptide comprising a growth hormone and at least one CTP peptide attached to an amino terminus of the growth hormone and at least two chorionic gonadotrophin carboxy terminal peptides attached to a carboxy terminus of the growth hormone. In another embodiment, the present invention provides a polypeptide comprising one chorionic gonadotrophin carboxy terminal peptide attached to an amino terminus of a growth hormone and two chorionic gonadotrophin carboxy terminal peptides attached to a carboxy terminus of a growth hormone.

In another embodiment, the terms "CTP peptide," "carboxy terminal peptide" and "CTP sequence" are used interchangeably herein. In another embodiment, the carboxy terminal peptide is a full-length CTP. In another embodiment, the carboxy terminal peptide is a truncated CTP. Each possibility represents a separate embodiment of the present invention.

In another embodiment, "signal sequence" and "signal peptide" are used interchangeably herein. In another embodiment, "sequence" when in reference to a polynucleotide can refer to a coding portion. Each possibility represents a separate embodiment of the present invention.

In another embodiment, the invention provides a polypeptide consisting of a growth hormone, a single chorionic gonadotrophin carboxy terminal peptide attached to the amino terminus of the growth hormone, and two chorionic gonadotrophin carboxy terminal peptides attached to the carboxy terminus of the growth hormone. In another embodiment, the invention provides a polypeptide consisting of a growth hormone, a single chorionic gonadotrophin carboxy terminal peptide attached to the amino terminus of the growth hormone, two chorionic gonadotrophin carboxy terminal peptides attached to the carboxy terminus of the growth hormone, and a signal peptide attached to the amino terminus of one chorionic gonadotrophin carboxy terminal peptide.

In another embodiment, a growth hormone comprising CTPs as described herein has enhanced in vivo biological activity compared the same growth hormone without CTPs. In another embodiment, a growth hormone comprising at least one CTP attached to its amino terminus and at least two CTPs attached to its carboxy terminus has enhanced in vivo biological activity compared the same growth hormone without CTPs. In another embodiment, a growth hormone comprising one CTP attached to its amino terminus and two CTPs attached to its carboxy terminus has enhanced in vivo biological activity compared the same growth hormone without CTPs.

In another embodiment, a subject is a human subject. In another embodiment, a subject is a pet. In another embodiment, a subject is a mammal. In another embodiment, a subject is a farm animal. In another embodiment, a subject is a monkey. In another embodiment, a subject is a horse. In another embodiment, a subject is a cow. In another embodiment, a subject is a mouse. In another embodiment, a subject is a rat. In one embodiment, the subject is male. In another embodiment, the subject is female.

In another embodiment, the configuration of CTP-growth hormone-CTP-CTP as described herein comprises a growth hormone or an active fragment thereof connected via a peptide bond to at least one CTP unit. In another embodiment, a CTP-growth hormone-CTP-CTP as described herein comprises a growth hormone or an active fragment thereof connected via a peptide bond to at least one CTP unit which is connected to an additional CTP unit via a peptide bond. In another embodiment, a polypeptide as described herein comprising a growth hormone fragments thereof and CTP units and/or fragments thereof are interconnected via a peptide bond. In another embodiment, one nucleic acid molecule encodes a polypeptide as described herein comprising a growth hormone and/or fragments thereof and CTP units and/or fragments thereof.

In another embodiment, the carboxy-terminal peptide (CTP) is attached to the growth hormone via a linker. In another embodiment, the linker which connects the CTP sequence to the growth hormone is a covalent bond. In another embodiment, the linker which connects the CTP sequence to the growth hormone is a peptide bond. In another embodiment, the linker which connects the CTP sequence to the growth hormone is a substituted peptide bond. In another embodiment, the carboxy-terminal peptide (CTP) sequence comprises an amino acid sequence selected from the sequences set forth in SEQ ID NO: 1 and SEQ ID NO: 2.

In another embodiment, SEQ ID NO: 1 comprise the following amino acid (AA) sequence: DPRFQDSSSSKAPPPSLPSPSRLPGPSDTPILQ (SEQ ID NO: 1). In another embodiment, SEQ ID NO: 2 comprise the following amino acid (AA) sequence: SSSSKAPPPSLPSPSRLPGPSDTPILPQ (SEQ ID NO: 2).

In another embodiment, the carboxy-terminal peptide (CTP) sequence is truncated. In another embodiment, a truncated CTP comprises the following amino acid sequence: SSSSKAPPPSLP (SEQ ID NO: 4).

In another embodiment, the carboxy terminal peptide (CTP) peptide of the present invention comprises the amino acid sequence from amino acid 112 to position 145 of a native human chorionic gonadotrophin peptide. In another embodiment, the CTP sequence of the present invention comprises the amino acid sequence from amino acid 118 to position 145 of a human chorionic gonadotropin peptide. In another embodiment, the CTP sequence also commences from any position between positions 112-118 and terminates at position 145 of human chorionic gonadotrophin peptide. In some embodiments, the CTP sequence peptide is 28, 29, 30, 31, 32, 33 or 34 amino acids long and commences at position 112, 113, 114, 115, 116, 117 or 118 of the gene bank deposited CTP amino acid sequence.

In another embodiment, the CTP peptide is a CTP peptide as described in U.S. Pat. No. which is incorporated herein by reference in its entirety. In another embodiment, the CTP peptide is a variant of chorionic gonadotrophin CTP which differs from the native CTP by 1-5 conservative amino acid substitutions as described in U.S. Pat. No. 5,712,122 which is incorporated herein by reference in its entirety. In another embodiment, the CTP peptide is a variant of chorionic gonadotrophin CTP which differs from the native CTP by 1 conservative amino acid substitution. In another embodiment, the CTP peptide is a variant of chorionic gonadotrophin CTP which differs from the native CTP by 2 conservative amino acid substitutions. In another embodiment, the CTP peptide is a variant of chorionic gonadotrophin CTP which differs from the native CTP by 3 conservative amino acid substitutions. In another embodiment, the CTP peptide is a variant of chorionic gonadotrophin CTP which differs from the native CTP by 4 conservative amino acid substitutions. In another embodiment, the CTP peptide is a variant of chorionic gonadotrophin CTP which differs from the native CTP by 5 conservative amino acid substitutions. In another embodiment, the CTP peptide amino acid sequence of the present invention is at least 70% homologous to the native CTP amino acid sequence or a peptide thereof. In another embodiment, the CTP peptide amino acid sequence of the present invention is at least 80% homologous to the native CTP amino acid sequence or a peptide thereof. In another embodiment, the CTP peptide amino acid sequence of the present invention is at least 90% homologous to the native CTP amino acid sequence or a peptide thereof. In another embodiment, the CTP peptide amino acid sequence of the present invention is at least 95% homologous to the native CTP amino acid sequence or a peptide thereof.

In another embodiment, the CTP peptide DNA sequence of the present invention is at least 70% homologous to the native human CTP DNA sequence or a peptide thereof. In another embodiment, the CTP peptide DNA sequence of the present invention is at least 80% homologous to the native human CTP DNA sequence or a peptide thereof. In another embodiment, the CTP peptide DNA sequence of the present invention is at least 90% homologous to the native CTP DNA sequence or a peptide thereof. In another embodiment, the CTP peptide DNA sequence of the present invention is at least 95% homologous to the native CTP DNA sequence or a peptide thereof.

In one embodiment, the truncated CTP comprises the first 11 amino acids of SEQ ID NO: 4. In one embodiment, the truncated CTP comprises the first 8 amino acids of SEQ ID NO: 4. In one embodiment, the truncated CTP comprises the first 13 amino acids of SEQ ID NO: 4. In one embodiment, the truncated CTP comprises the first 6 amino acids of SEQ ID NO: 4. In one embodiment, the truncated CTP comprises the first 5 amino acids of SEQ ID NO: 4.

In one embodiment, at least one of the chorionic gonadotrophin CTP amino acid sequences is glycosylated. In another embodiment, both of the chorionic gonadotrophin CTP amino acid sequences are glycosylated. In another embodiment, 2 of the chorionic gonadotrophin CTP amino acid sequences are glycosylated. In another embodiment, 2 or more of the chorionic gonadotrophin CTP amino acid sequences are glycosylated. In another embodiment, all of the chorionic gonadotrophin CTP amino acid sequences are glycosylated. In one embodiment, the CTP sequence of the present invention comprises at least one glycosylation site. In one embodiment, the CTP sequence of the present invention comprises 2 glycosylation sites. In one embodiment, the CTP sequence of the present invention comprises 3 glycosylation sites. In one embodiment, the CTP sequence of the present invention comprises 4 glycosylation sites.

In another embodiment, at least one carboxy-terminal peptide (CTP) sequence comprises an amino acid sequence selected from the sequences set forth in SEQ ID NO: 1 and SEQ ID NO: 2. In another embodiment, at least one carboxy-terminal peptide (CTP) is truncated.

In one embodiment, the terms "termini", "terminal", "terminal end" and "terminus" when in reference to a carboxy or amino end of a protein or peptide or fragment thereof provided herein, are used interchangeably herein. In another embodiment, the terms "C-terminal", "carboxy terminal" or "carboxyl terminal" are used interchangeably herein. In another embodiment, the terms "N-terminal" and "amino terminal" are used interchangeably herein. Each possibility represents a separate embodiment of the present invention.

In another embodiment, a CTP sequences at both the amino terminal end of a growth hormone and at the carboxy terminal end of the growth hormone provides enhanced protection against degradation of a growth hormone. In another embodiment, at least one CTP sequence at the amino terminal end of a growth hormone and two CTP units in the carboxy terminal end of a growth hormone provides enhanced protection against clearance. In another embodiment, at least one CTP sequence at the amino terminal end of a growth hormone and two CTP units in the carboxy terminal end of a growth hormone provides prolonged clearance time. In another embodiment, at least one CTP sequence at the amino terminal end of a growth hormone and two CTP units in the carboxy terminal end of a growth hormone enhances the $C_{max}$ of a growth hormone. In another embodiment, at least one CTP sequence at the amino terminal end of a growth hormone and two CTP units in the carboxy terminal end of a growth hormone enhances the $T_{max}$ of a growth hormone. In another embodiment, at least one CTP sequence at the amino terminal end of a growth hormone and two CTP units in the carboxy terminal end of a growth hormone enhanced T½ (half-life) of the growth hormone.

In another embodiment, CTP sequences at both the amino terminal end of a growth hormone and at the carboxy terminal end of the growth hormone extend the half-life of the modified growth hormone. In another embodiment, at least a single CTP sequence at the amino terminal end of a growth hormone and at least two CTP sequences at the carboxy terminal end of the growth hormone provide extended half-life to the modified growth hormone. In another embodiment, a single CTP sequence at the amino terminal end of a growth hormone and two CTP sequences at the carboxy terminal end of the growth hormone provide extended half-life to the attached growth hormone. In another embodiment, a single CTP sequence at the amino terminal end of a growth hormone and two CTP sequences in tandem at the carboxy terminal end of the growth hormone provide extended half-life to the modified growth hormone.

In another embodiment, a CTP sequence at the amino terminal end of a polypeptide, a CTP sequence at the carboxy terminal end of the growth hormone, and at least one additional CTP sequence attached in tandem to the CTP sequence at the carboxy terminus provide enhanced protection against degradation to a growth hormone. In some embodiments, a CTP sequence at the amino terminal end of a growth hormone, a CTP sequence at the carboxy terminal end of the growth hormone, and at least one additional CTP sequence attached in tandem to the CTP sequence at the carboxy terminus extend the half-life of the growth hormone. In some embodiments, a CTP sequence at the amino terminal end of a growth hormone, a CTP sequence at the carboxy terminal end of the growth hormone, and at least one additional CTP sequence attached in tandem to the CTP sequence at the carboxy terminus enhance the biological activity of the growth hormone.

In another embodiment, the growth hormone further comprises a signal peptide. In some embodiments, signal sequences include, but are not limited to the endogenous signal sequence. In some embodiments, signal sequences include, but are not limited to the endogenous signal sequence of any known growth hormone or growth hormones. In another embodiment, the polypeptides and methods of the present invention provide a growth hormone having additionally a signal peptide comprising the following amino acid sequence: MATGSRTSLLLAFGLLCLPWLQEGSA (SEQ ID NO: 3).

In another embodiment, conjugated growth hormones of this invention are used in the same manner as unmodified growth hormones. In another embodiment, conjugated growth hormones of this invention have an increased circulating half-life and plasma residence time, decreased clearance, and increased clinical activity in vivo. In another embodiment, due to the improved properties of the conjugated growth hormones as described herein, these conjugates are administered less frequently than unmodified growth hormones. In another embodiment, conjugated growth hormones as described herein are administered once a week to once every two weeks. In another embodiment, conjugated growth hormones as described herein are administered once every two weeks to once every three weeks. In another embodiment, conjugated growth hormones as described herein are administered once a day to three times a week. In another embodiment, decreased frequency of administration will result in improved patient compliance leading to improved treatment outcomes, as well as improved patient quality of life. In another embodiment, compared to conventional conjugates of growth hormones linked to poly(ethylene glycol) it has been found that growth hormone CTP conjugates having the molecular weight and linker structure of the conjugates of this invention have an improved potency, improved stability, elevated AUC levels, enhanced circulating half-life. In another embodiment, compared to conventional conjugates of growth hormones linked to poly(ethylene glycol) it has been found that growth hormones having the molecular weight and linker structure of the conjugates of this invention have an improved potency, improved stability, elevated AUC levels, enhanced circulating half-life. In another embodiment, a therapeutically effective amount of a conjugated growth hormone is the amount of conjugate necessary for the in vivo measurable expected biological activity. In another embodiment, a growth hormone utilized according to the teachings of the present invention exhibits increased potency. In another embodiment, the attachment of CTP sequence to both the amino and carboxy termini of a growth hormone results in prolonged in-vivo activity.

In another embodiment, a therapeutically effective amount of a conjugated growth hormone is determined according to factors as the exact type of condition being treated, the condition of the patient being treated, as well as the other ingredients in the composition. In another embodiment, a therapeutically effective amount of a conjugated growth hormone is 0.01 to 10 µg per kg body weight administered once a week. In another embodiment, a therapeutically effective amount of a conjugated growth hormone is 0.1 to 1 µg per kg body weight, administered once a week. In another embodiment, a pharmaceutical composition comprising a conjugated growth hormone is formulated at strength effective for administration by various means to a human patient.

In another embodiment, the growth hormone is any growth hormone known to one of skill in the art. In another embodiment, the growth hormone is a human growth hormone. In another embodiment, the nucleotide sequence and/or the amino acid sequence of a growth hormone is available in a gene bank database. In another embodiment, the growth hormone is a homologue. In another embodiment, a homologue also refers to a deletion, insertion, or substitution variant, including an amino acid substitution, thereof and biologically active polypeptide fragments thereof.

In another embodiment, the growth hormone is variant of hGH missing exons 2, 3, 4, or any combination thereof. In another embodiment, the growth hormone comprises a signal peptide. In another embodiment, the growth hormone comprises a signal cleavage site. In another embodiment, polypeptides comprising GH modified by CTPs of the present invention comprise recombinant GH.

In another embodiment, a growth hormone as described herein is a member of the superfamily of growth hormone (GH)-like cytokines. In another embodiment, a growth hormone as described herein is human growth hormone (hGH). In another embodiment, a human growth hormone comprises the following amino acid sequence (Genbank Accession No. P01241): MATGSRTSLLLAFGLLCLPWLQEGSAFPTIPLSRLFDNAMLRAHRLHQLAFDTYQEFEEAYIPKEQKYSFLQNPQTSLCFSESIPTPSNREETQQKSNLELLRISLLLIQSWLEPVQFLRSVFANSLVY GASDSN- VYDLLKDLEEGIQTLMGRLEDGSPRTGQIFKQ-
TYSKFDTNSHNDDALLKNYGLLYC
FRKDMDKVETFLRIVQCRSVEGSCGF (SEQ ID NO: 5).
In another embodiment, a human growth hormone comprises the following amino acid sequence: MFPTIPLSR-LFDNAMLRAHRLHQLAFDTYQEFEEAYIPKEQKYS-FLQNPQTSLCFSESIPTPSNR
EETQQKSNLELLRISLLLIQSWLEPVQFLRSV-FANSLVYGASDSNVYDLLKDLEEGIQTLMGRL EDG-SPRTGQIFKQTYSKFDTNSHNDDALLKNYGLLYC-FRKDMDKVETFLRIVQCRSVEGSCG F (SEQ ID NO: 6). In another embodiment, a human growth hormone comprises the following amino acid sequence: MFPTIPLSR-LFDNAMLRAHRLHQLA (SEQ ID NO: 7). In another embodiment, an hGH comprises the following amino acid sequence: MATGSRTSLLLAFGLLCLPWLQEGSAFPTI-PLSRLFDNAMLRAHRLHQLAFDTYQEFEEAYIP
KVQKYSFLQNPQTSLCFSESIPTPSNREETQQKSN-LELLRISLLLIQSWLEPVQFLRSVFANSLV YGASDSN-VYDLLKDLEEGIQTLMGRLEDGSPRTGQIFKQ-TYSKFDTNSHNDDALLKNYGLLY
CFRKDMDKVETFLRIVQCRSVEGSCGF (SEQ ID NO: 8). In another embodiment, an hGH is a substitution variant in which glutamine in position 65 of hGH is substituted by a valine.

In another embodiment, a growth hormone of the invention comprises the gene bank amino acid deposited sequence under accession no. AAA72260. In another embodiment, a growth hormone of the invention comprises the gene bank amino acid deposited sequence under accession no. AAK69708. In another embodiment, a growth hormone of the invention comprises the gene bank amino acid deposited sequence under accession no. CAA01435. In another embodiment, a growth hormone of the invention comprises the gene bank amino acid deposited sequence under accession no. CAA01329. In another embodiment, a growth hormone of the invention comprises the gene bank amino acid deposited sequence under accession no. CAA00380. In another embodiment, a growth hormone of the invention comprises the gene bank amino acid deposited sequence under accession no. AAA72555. In another embodiment, a growth hormone of the invention comprises the gene bank amino acid deposited sequence under accession no. NP_000506.2. In another embodiment, a growth hormone of the invention comprises the gene bank amino acid deposited sequence under accession no. NP_072053.1. In another embodiment, a growth hormone of the invention comprises the gene bank amino acid deposited sequence under accession no. NP_072054.1. In another embodiment, a growth hormone of the invention comprises the gene bank amino acid deposited sequence under accession no. NP_072055.1. In another embodiment, a growth hormone of the invention comprises the gene bank amino acid deposited sequence under accession no. NP_072056.1.

In another embodiment, the nucleic acid molecule encoding a growth hormone as described herein encodes any amino acid sequence of a growth hormone known to one of skill in the art. In another embodiment, the nucleic acid molecule encoding a growth hormone as described herein encodes an hGH. In another embodiment, the nucleic acid molecule encoding a growth hormone comprises the gene bank nucleic acid deposited sequence under accession no. NM_000515.3. In another embodiment, the nucleic acid molecule encoding a growth hormone comprises the gene bank nucleic acid deposited sequence under accession no. NM_022559.2. In another embodiment, the nucleic acid molecule encoding a growth hormone comprises the gene bank nucleic acid deposited sequence under accession no. NM_022560.2. In another embodiment, the nucleic acid molecule encoding a growth hormone comprises the gene bank nucleic acid deposited sequence under accession no. NM_22561.2. In another embodiment, the nucleic acid molecule encoding a growth hormone comprises the gene bank nucleic acid deposited sequence under accession no. NM_022562.2.

In another embodiment, a polypeptide comprising a growth hormone of the invention comprises one CTP attached to a carboxy terminus of a growth hormone (hGH-CTP) and having the following amino acid sequence:

```
                                    (SEQ ID NO: 9)
MATGSRTSLLLAFGLLCLPWLQEGSAFPTIPLSRLFDNAMLRAHRLH

QLAFDTYQEFEEAYIPKEQKYSFLQNPQTSLCFSESIPTPSNREETQ

QKSNLELLRISLLLIQSWLEPVQFLRSVFANSLVYGASDSNVYDLLK

DLEEGIQTLMGRLEDGSPRTGQIFKQTYSKFDTNSHNDDALLKNYGL

LYCFRKDMDKVETFLRIVQCRSVEGSCGFSSSSKAPPPSLPSPSRLP

GPSDTPILPQ.
```

In another embodiment, a polypeptide comprising a growth hormone of the invention comprises two CTPs in tandem attached to a carboxy terminus of a growth hormone (hGH-CTP-CTP) and having the following amino acid sequence:

```
                                   (SEQ ID NO: 10)
MATGSRTSLLLAFGLLCLPWLQEGSAFPTIPLSRLFDNAMLRAHRLH

QLAFDTYQEFEEAYIPKEQKYSFLQNPQTSLCFSESIPTPSNREETQ

QKSNLELLRISLLLIQSWLEPVQFLRSVFANSLVYGASDSNVYDLLK

DLEEGIQTLMGRLEDGSPRTGQIFKQTYSKFDTNSHNDDALLKNYGL

LYCFRKDMDKVETFLRIVQCRSVEGSCGFSSSSKAPPPSLPSPSRLP

GPSDTPILPQSSSSKAPPPSLPSPSRLPGPSDTPILPQ.
```

In another embodiment, a polypeptide comprising a growth hormone of the invention comprises two CTPs attached in tandem to a carboxy terminus of a growth hormone and one CTP attached to an amino terminus of a growth hormone (CTP-hGH-CTP-CTP) and having the following amino acid sequence:

```
                                   (SEQ ID NO: 11)
MATGSRTSLLLAFGLLCLPWLQEGSASSSSKAPPPSLPSPSRLPGPS

DTPILPQFPTIPLSRLFDNAMLRAHRLHQLAFDTYQEFLEAYIPKEQ

KYSFLQNPQTSLCFSESIPTPSNREETQQKSNLELLRISLLLIQSWL

EPVQFLRSVFANSLVYGASDSNVYDLLKDLEEGIQTLMGRLEDGSPR

TGQIFKQTYSKFDTNSHNDDALLKNYGLLYCFRKDMDKVETFLRIVQ

CRSVEGSCGFSSSSKAPPPSLPSPSRLPGPSDTPILPQSSSSKAPPP

SLPSPSRLPGPSDTPILPQ.
```

In another embodiment, a polypeptide comprising a growth hormone of the invention comprises two CTPs in tandem attached to a carboxy terminus of a growth hormone, wherein one CTP of two CTPs is truncated, and one additional CTP attached to an amino terminus of a growth hormone (tCTP-hGH-CTP-CTP) and having the following amino acid sequence:

(SEQ ID NO: 12)
MATGSRTSLLLAFGLLCLPWLQEGSASSSSKAPPPSLPFPTIPLSRL

FDNAMLRAHRLHQLAFDTYQEFEEAYIPKEQKYSFLQNPQTSLCFSE

SIPTPSNREETQQKSNLELLRISLLLIQSWLEPVQFLRSVFANSLVY

GASDSNVYDLLKDLEEGIQTLMGRLEDGSPRTGQIFKQTYSKFDTNS

HNDDALLKNYGLLYCFRKDMDKVETFLRIVQCRSVEGSCGFSSSSKA

PPPSLPSPSRLPGPSDTPILPQSSSSKAPPPSLPSPSRLPGPSDTPI

LPQ.

In another embodiment, a polypeptide comprising a growth hormone of the invention comprises one CTP attached to a carboxy terminus of a growth hormone and one CTP attached to an amino terminus of a growth hormone (CTP-hGH-CTP) and having the following amino acid sequence:

(SEQ ID NO: 13)
MATGSRTSLLLAFGLLCLPWLQEGSASSSSKAPPPSLPSPSRLPGPS

DTPILPQFPTIPLSRLFDNAMLRAHRLHQLAFDTYQEFEEAYIPKEQ

KYSFLQNPQTSLCFSESIPTPSNREETQQKSNLELLRISLLLIQSWL

EPVQFLRSVFANSLVYGASDSNVYDLLKDLEEGIQTLMGRLEDGSPR

TGQIFKQTYSKFDTNSHNDDALLKNYGLLYCFRKDMDKVETFLRIVQ

CRSVEGSCGFSSSSKAPPPSLPSPSRLPGPSDTPILPQ.

In another embodiment, a polypeptide comprising a growth hormone and one CTP comprises the following amino acid sequence:

(SEQ ID NO: 14)
MATGSRTSLLLAFGLLCLPWLQEGSASSSSKAPPPSLPSPSRLPGPSD

TPILPQFPTIPLSRLFDNAMLRAHRLHQLAFDTYQEFEEAYIPKEQKY

SFLQNPQTSLCFSESIPTPSNREETQQKSNLELLRISLLLIQSWLEPV

QFLRSVFANSLVYGASDSNVYDLLKDLEEGIQTLMGRLEDGSPRTGQI

FKQTYSKFDTNSHNDDALLKNYGLLYCFRKDMDKVETFLRIVQCRSVE

GSCGF.

In another embodiment, a polynucleotide molecule encoding a polypeptide having CTP-hGH-CTP comprises the following nucleic acid sequence:

(SEQ ID NO: 15)
tctagaggacatggccaccggcagcaggaccagcctgctgctggcctt cggcctgctgtgcctgccatggctgcaggagggcagcgccagctcttc ttctaaggctccaccccatctctgcccagcccagcagactgccggg ccccagcgacacacccattctgccccagttccccaccatcccctgag caggctgttcgacaacgccatgctgagggctcacaggctgcaccagct ggcctttgacacctaccaggagttcgaggaagcctacatccccaagga gcagaagtacagcttcctgcagaaccccagacctccctgtgcttcag cgagagcatccccaccccagcaacagagaggagacccagcagaagag caacctggagctgctgaggatctccctgctgctgatccagagctggct ggagcccgtgcagttcctgagaagcgtgttcgccaacagcctggtgta cggcgccagcgacagcaacgtgtacgacctgctgaaggacctggagga gggcatccagaccctgatgggccggctggaggacggcagcccaggac cggccagatcttcaagcagacctacagcaagttcgacaccaacagcca caacgacgacgccctgctgaagaactacgggctgctgtactgcttcag aaaggacatggacaaggtggagaccttcctgaggatcgtgcagtgcag aagcgtggagggcagctgcggcttcagctccagcagcaaggcccctcc cccgagcctgccctccccaagcaggctgcctgggccctccgacacacc aatcctgcctcagtgatgaaggtctggatgcggccgc.

In another embodiment, a polynucleotide molecule encoding a polypeptide having CTP-hGH-CTP-CTP comprises the following nucleic acid sequence:

(SEQ ID NO: 16)
tctagaggacatggccaccggcagcaggaccagcctgctgctggcctt cggcctgctgtgcctgccatggctgcaggagggcagcgccagctcttc ttctaaggctccaccccatctctgcccagcccagcagactgccggg ccccagcgacacacccattctgccccagttccccaccatcccctgag caggctgttcgacaacgccatgctgagggctcacaggctgcaccagct ggcctttgacacctaccaggagttcgaggaagcctacatccccaagga gcagaagtacagcttcctgcagaaccccagacctccctgtgcttcag cgagagcatccccaccccagcaacagagaggagacccagcagaagag caacctggagctgctgaggatctccctgctgctgatccagagctggct ggagcccgtgcagttcctgagaagcgtgttcgccaacagcctggtgta cggcgccagcgacagcaacgtgtacgacctgctgaaggacctggagga gggcatccagaccctgatgggccggctggaggacggcagcccaggacc ggccagatcttcaagcagacctacagcaagttcgacaccaacagccac aacgacgacgccctgctgaagaactacgggctgctgtactgcttcaga aaggacatggacaaggtggagaccttcctgaggatcgtgcagtgcaga agcgtggagggcagctgcggcttcagctccagcagcaaggcccctccc ccgagcctgccctccccaagcaggctgcctgggccctccgacacacca atcctgccacagagcagctcctctaaggcccctcctccatccctgcca tcccctcccggctgcctggccctctgacacccctatcctgcctcag tgatgaaggtctggatgcggccgc.

In another embodiment, a polynucleotide molecule encoding a polypeptide having CTP-hGH-CTP-CTP comprises the following nucleic acid sequence:

(SEQ ID NO: 17)
tctagaggacatggccaccggcagcaggaccagcctgctgctggcct tcggcctgctgtgcctgccatggctgcaggagggcagcgccagctct tcttctaaggctccaccccgagcctgccttccccaccatccccct gagcaggctgttcgacaacgccatgctgagggctcacaggctgcacc

```
-continued
agctggcctttgacacctaccaggagttcgaggaagcctacatcccc aaggagcagaagtacagcttcctgcagaaccccagacctccctgtg cttcagcgagagcatcccacccccagcaacagagaggagacccagc agaagagcaacctggagctgctgaggatctccctgctgctgatccag agctggctggagcccgtgcagttcctgagaagcgtgttcgccaacag cctggtgtacggcgccagcgacagcaacgtgtacgacctgctgaagg acctggaggagggcatccagaccctgatgggccggctggaggacggc agccccaggaccggccagatcttcaagcagacctacagcaagttcga caccaacagccacaacgacgacgccctgctgaagaactacgggctgc tgtactgcttcagaaaggacatggacaaggtggagaccttcctgagg atcgtgcagtgcagaagcgtggagggcagctgcggcttcagctccag cagcaaggccctcccccgagcctgccctccccaagcaggctgcctg ggccctccgacacaccaatcctgccacagagcagctcctctaaggcc cctcctccatccctgccatcccctcccggctgcctggcccctctga caccctatcctgcctcagtgatgaaggtctggatgcggccgc.
```

In another embodiment, a growth hormone of the invention is homologous to a known sequence of a growth hormone. In another embodiment, a growth hormone of the invention is homologous to a growth hormone sequence as disclosed herein. In some embodiments, homology according to the present invention also encompasses deletions, insertions, or substitution variants, including an amino acid substitution, thereof and biologically active polypeptide fragments thereof. In one embodiment the substitution variant is one, in which the glutamine in position 65 of hGH is substituted by a valine [Gellerfors et al., J Pharm Biomed Anal 1989, 7:173-83].

In one embodiment, the phrase "human growth hormone" (hGH) refers to a polypeptide, such as set forth in Genbank Accession No. P01241 exhibiting hGH activity (i.e. stimulation of growth).

In one embodiment, "human growth hormone" (hGH) refers to a polypeptide, such as set forth in Genbank Accession No. P01241, exhibiting hGH activity (i.e. stimulation of growth). In one embodiment, hGH of the present invention also refers to homologues. In one embodiment, hGH amino acid sequence of the present invention is at least 50% homologous to an hGH sequence set forth in GenBank Accession No. P01241 as determined using BlastP software of the National Center of Biotechnology Information (NCBI) using default parameters). In one embodiment, hGH amino acid sequence of the present invention is at least 60% homologous to an hGH sequence set forth in GenBank Accession No. P01241 as determined using BlastP software of the National Center of Biotechnology Information (NCBI) using default parameters). In one embodiment, hGH amino acid sequence of the present invention is at least 70% homologous to an hGH sequence set forth in GenBank Accession No. P01241 as determined using BlastP software of the National Center of Biotechnology Information (NCBI) using default parameters). In one embodiment, hGH amino acid sequence of the present invention is at least 80% homologous to an hGH sequence set forth in GenBank Accession No. P01241 as determined using BlastP software of the National Center of Biotechnology Information (NCBI) using default parameters). In one embodiment, hGH amino acid sequence of the present invention is at least 90% homologous to an hGH sequence set forth in GenBank Accession No. P01241 as determined using BlastP software of the National Center of Biotechnology Information (NCBI) using default parameters). In one embodiment, hGH amino acid sequence of the present invention is at least 95% homologous to an hGH sequence set forth in GenBank Accession No. P01241 as determined using BlastP software of the National Center of Biotechnology Information (NCBI) using default parameters).

In another embodiment, polypeptides comprising hGH modified by CTPs bind adipocytes and stimulates them to break down triglyceride and suppresses their ability to take up and accumulate circulating lipids. In another embodiment, polypeptides comprising hGH modified by CTPs exert indirect effects mediated primarily by a insulin-like growth factor-I (IGF-I) (as shown in the examples section).

In another embodiment, polypeptides comprising hGH modified by CTPs stimulate body growth by stimulating the liver and other tissues to secrete IGF-I. In another embodiment, IGF-I stimulates proliferation of chondrocytes, resulting in bone growth. In another embodiment, IGF-I stimulates proliferation of skeletal muscle cells, resulting in muscle growth.

In another embodiment, polypeptides comprising hGH modified by CTPs induce a metabolic effect on protein, lipid, and carbohydrate metabolism. In another embodiment, polypeptides comprising hGH modified by CTPs have a direct effect. In another embodiment, polypeptides comprising hGH modified by CTPs have an indirect effect through induction of IGF-I. In another embodiment, polypeptides comprising hGH modified by CTPs further comprise a leader peptide. In another embodiment, polypeptides comprising hGH modified by CTPs include CTP truncated constructs.

In another embodiment, polypeptides comprising hGH modified by CTPs stimulate protein anabolism in a tissue. In another embodiment, polypeptides comprising hGH modified by CTPs stimulate amino acid uptake, increased protein synthesis, and decreased oxidation of proteins.

In another embodiment, polypeptides comprising hGH modified by CTPs stimulate fat metabolism. In another embodiment, polypeptides comprising hGH modified by CTPs stimulate the utilization of fat by stimulating triglyceride breakdown and oxidation in adipocyte. In another embodiment, polypeptides comprising hGH modified CTPs reduce body fat.

In another embodiment, polypeptides comprising hGH modified by CTPs stimulate carbohydrate metabolism. In another embodiment, polypeptides comprising hGH modified by CTPs maintain blood glucose within a normal range. In another embodiment, polypeptides comprising hGH modified by CTPs comprise an anti-insulin activity. In another embodiment polypeptides comprising hGH modified by CTPs suppress the abilities of insulin to stimulate uptake of glucose in peripheral tissues and enhance glucose synthesis in the liver. In another embodiment, polypeptides comprising hGH modified by CTPs stimulate insulin secretion, leading to hyperinsulinemia.

In another embodiment, polypeptides comprising hGH modified by CTPs are used to compensate for limited or no production of growth hormone in a subject. In another embodiment, polypeptides comprising hGH modified by CTPs compensate for limited or no production of growth hormone-releasing hormone (GHRH). In another embodiment, polypeptides comprising hGH modified by CTPs compensate for the increased activity of somatostatin. In another embodiment, polypeptides comprising hGH modified by CTPs compensate for limited or no production of ghrelin.

In another embodiment, polypeptides comprising hGH modified by CTPs are used to treat diseases associated with lesions in either the hypothalamus, the pituitary, or in target cells. In another embodiment, polypeptides comprising hGH modified by CTPs are used to treat diseases associated with reduced target cell's response to the hormone.

In another embodiment, polypeptides comprising hGH modified by CTPs are used to treat children with severe growth retardation. In another embodiment, polypeptides comprising hGH modified by CTPs are used to treat children of pathologically short stature. In another embodiment, polypeptides comprising hGH modified by CTPs of the invention are used to enhance athletic performance. In another embodiment, polypeptides comprising hGH modified by CTPs of the invention are used to treat symptoms of aging. In another embodiment, polypeptides comprising hGH modified by CTPs of the invention are used to treat cosmetic symptoms of aging.

In another embodiment, treating GH deficient children with GH results in growth enhancement, whereas in GH-deficient adults, treatment with GH results in an increase in lean body mass and a decrease or reduction in body fat. In another embodiment, treatment with CTP modified forms of GH results in an enhancement of these effects in children and adults. In another embodiment, treatment with CTP-modified hGH in GH-deficient children results in an enhancement of growth when compared to GH-deficient children receiving the same dose of daily, commercial, unmodified GH. In another embodiment, treatment with CTP-modified hGH in children results in an enhancement of growth when compared to children receiving the same dose of daily, commercial, unmodified GH. In another embodiment, treatment with CTP-modified hGH in GH-deficient adults results in an increase in lean body mass and reduced body fat when compared to GH-deficient adults receiving the same dose of daily, commercial, unmodified GH. In another embodiment, treatment with CTP-modified hGH in adults results in an increase in lean body mass and reduced body fat when compared to adults receiving the same dose of daily, commercial, unmodified GH.

In another embodiment, polypeptides comprising hGH modified by CTPs of the invention are used for enhancing milk production in a female subject. In another embodiment, CTP/cowGH conjugates of the invention are used for enhancing milk production in dairy cattle. In another embodiment, CTP/animal-GH constructs of the invention are used in animal agriculture technology. In another embodiment, CTP/farm animal-GH constructs of the invention are used for enhancing growth of farm animal such as but not limited to pigs.

In another embodiment, the methods of the present invention provide polypeptides comprising hGH modified by CTPs for stimulating muscle growth, increasing cardiac function, stimulating bone growth, maintaining muscle integrity, balancing muscle metabolism, inducing muscle buildup, inducing de-novo muscle build-up, enhancing bone load, treating symptoms associated with osteoporosis, treating a wasting disease, increasing lipolysis, improving fluid balance, treating osteoporosis, improving lung function, improving immunity, regrowing a vital organ, increasing sense of well-being, restoring REM sleep, or any combination thereof. In another embodiment, the methods of the present invention provide polypeptides comprising hGH modified by CTPs for stimulating muscle growth, increasing cardiac function, stimulating bone growth, maintaining muscle integrity, balancing muscle metabolism, inducing muscle buildup, inducing de-novo muscle build-up, enhancing bone load, treating symptoms associated with osteoporosis, treating a wasting disease, increasing lipolysis, improving fluid balance, treating osteoporosis, improving lung function, improving immunity, regrowing a vital organ, increasing sense of well-being, restoring REM sleep, or any combination thereof.

In another embodiment, the methods of the present invention provide hGH having additionally at least one CTP amino acid peptide on the N-terminus and at least one CTP amino acid peptide on the C-terminus for the treatment of wasting disease, AIDS, cachexia, or hGH deficiency. In another embodiment, the methods of the present invention provide polypeptides comprising hGH modified by CTPs for the treatment of wasting disease, AIDS, cachexia, or hGH deficiency.

In some embodiment, human growth hormone polypeptides of the present invention can be used to treat a subject afflicted with conditions related to growth and weight, such as a growth deficiency disorder, AIDS wasting, aging, impaired immune function of HIV-infected subjects, a catabolic illness, surgical recovery, a congestive cardiomyopathy, liver transplantation, liver regeneration after hepatectomy, chronic renal failure, renal osteodystrophy, osteoporosis, achondroplasia/hypochondroplasia, skeletal dysplasia, a chronic inflammatory or nutritional disorder such as Crohn's disease, short bowel syndrome, juvenile chronic arthritis, cystic fibrosis, male infertility, X-linked hypophosphatemic rickets, Down's syndrome, Spina bifida, Noonan Syndrome, obesity, impaired muscle strength and fibromyalgia.

In another embodiment, human growth hormone polypeptides of the present invention can be used to treat a subject with multiple sclerosis. In another embodiment, human growth hormone polypeptides of the present invention can be used to enhance weight loss in obese subjects. In another embodiment, human growth hormone polypeptides of the present invention can be used to decrease body fat in obese subjects. In another embodiment, human growth hormone polypeptides of the present invention can be used to increase lean body mass in a subject. In another embodiment, human growth hormone polypeptides of the present invention can be used to treat a subject suffering from heart failure, ulcerative colitis, and burns. In another embodiment, human growth hormone polypeptides of the present invention may be used to build muscle mass.

In another embodiment, the methods of the present invention provide a nucleic acid sequence encoding a GH protein as described herein. In another embodiment, the methods of the present invention provide a nucleic acid sequence encoding polypeptide comprising hGH modified by CTPs for stimulating muscle growth, increasing cardiac function, stimulating bone growth, maintaining muscle integrity, balancing muscle metabolism, inducing muscle buildup, inducing de-novo muscle build-up, enhancing bone load, treating symptoms associated with osteoporosis, treating a wasting disease, increasing lipolysis, improving fluid balance, treating osteoporosis, improving lung function, improving immunity, regrowing a vital organ, increasing sense of well-being, restoring REM sleep, or any combination thereof.

Figure 2:
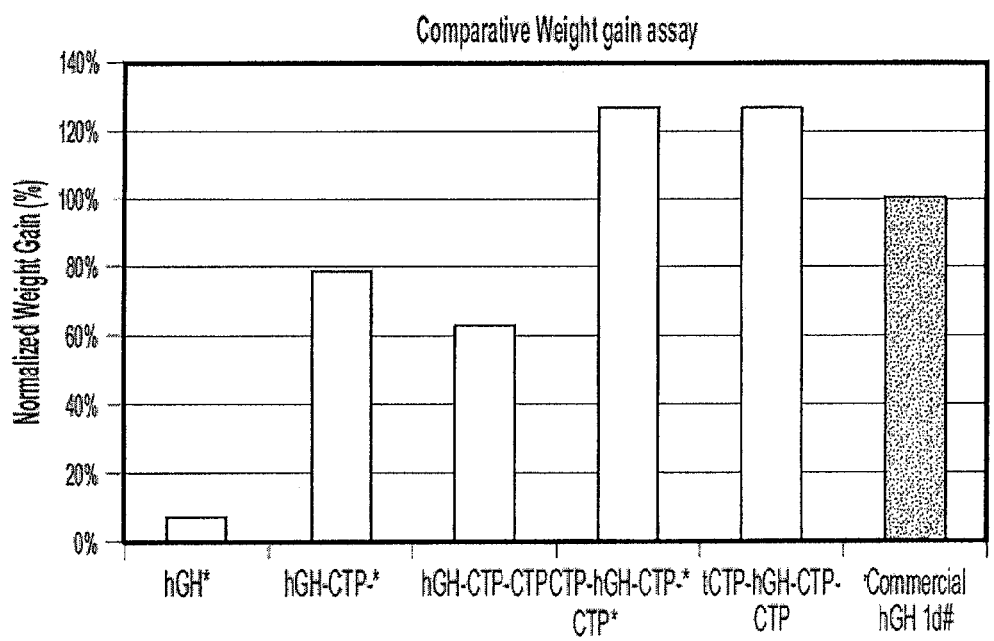
FIG. 2 is a bar graph illustrating the weight gain of hypophysectomized rats following administration of the GH-CTP polypeptides (the different MODs) of the present invention.
Figure 3:
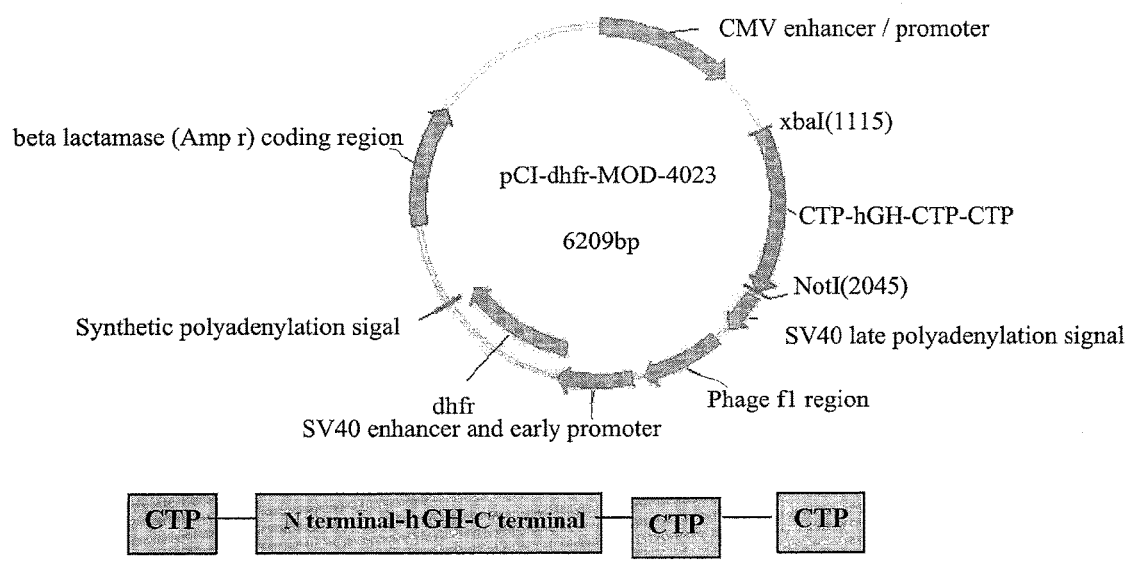
FIG. 3 includes two schemes (1) a map of CTP-hGH-CTP-CTP pCI-dhfr Plasmid and (2) structural protein formula of CTP-hGH-CTP-CTP.

In some embodiments, human growth hormone (hGH) is utilized according to the teachings of the present invention. In some embodiments, the attachment of CTP sequence to both the amino and carboxy termini of the hGH protein results in increased potency (FIG. 2). In some embodiments, the attachment of CTP sequence to both the amino and carboxy termini of the hGH protein results in prolonged in-vivo activity.

In some embodiments, "polypeptide" or "protein" as used herein encompasses native polypeptides (either degradation products, synthetically synthesized polypeptides or recombinant polypeptides) and peptidomimetics (typically, synthetically synthesized polypeptides), as well as peptoids and semipeptoids which are polypeptide analogs, which have, in some embodiments, modifications rendering the polypeptides even more stable while in a body or more capable of penetrating into cells.

In some embodiments, modifications include, but are not limited to N terminus modification, C terminus modification, polypeptide bond modification, including, but not limited to, CH2-NH, CH2-S, CH2-S=O, O=C—NH, CH2-O, CH2-CH$_2$, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

In some embodiments, polypeptide bonds (—CO—NH—) within the polypeptide are substituted. In some embodiments, the polypeptide bonds are substituted by N-methylated bonds (—N(CH3)-CO—). In some embodiments, the polypeptide bonds are substituted by ester bonds (—C(R)H—C—O—O—C(R)—N—). In some embodiments, the polypeptide bonds are substituted by ketomethylen bonds (—CO—CH2-). In some embodiments, the polypeptide bonds are substituted by α-aza bonds (—NH—N(R)—CO—), wherein R is any alkyl, e.g., methyl, carba bonds (—CH2-NH—). In some embodiments, the polypeptide bonds are substituted by hydroxyethylene bonds (—CH(OH)—CH2-). In some embodiments, the polypeptide bonds are substituted by thioamide bonds (—CS—NH—). In some embodiments, the polypeptide bonds are substituted by olefinic double bonds (—CH=CH—). In some embodiments, the polypeptide bonds are substituted by retro amide bonds (—NH—CO—). In some embodiments, the polypeptide bonds are substituted by polypeptide derivatives (—N(R)—CH2-CO—), wherein R is the "normal" side chain, naturally presented on the carbon atom. In some embodiments, these modifications occur at any of the bonds along the polypeptide chain and even at several (2-3 bonds) at the same time.

In some embodiments, natural aromatic amino acids of the polypeptide such as Trp, Tyr and Phe, are substituted for synthetic non-natural acid such as Phenylglycine, TIC, naphthylelanine (Nol), ring-methylated derivatives of Phe, halogenated derivatives of Phe or o-methyl-Tyr. In some embodiments, the polypeptides of the present invention include one or more modified amino acid or one or more non-amino acid monomers (e.g. fatty acid, complex carbohydrates etc).

In one embodiment, "amino acid" or "amino acid" is understood to include the 20 naturally occurring amino acid; those amino acid often modified post-translationally in vivo, including, for example, hydroxyproline, phosphoserine and phosphothreonine; and other unusual amino acid including, but not limited to, 2-aminoadipic acid, hydroxylysine, isodesmosine, nor-valine, nor-leucine and ornithine. In one embodiment, "amino acid" includes both D- and L-amino acid.

In some embodiments, the polypeptides of the present invention are utilized in therapeutics which requires the polypeptides to be in a soluble form. In some embodiments, the polypeptides of the present invention include one or more non-natural or natural polar amino acid, including but not limited to serine and threonine which are capable of increasing polypeptide solubility due to their hydroxyl-containing side chain.

In some embodiments, the polypeptides comprising hGH modified by CTPs of the present invention are utilized in a linear form, although it will be appreciated by one skilled in the art that in cases where cyclicization does not severely interfere with hGH modified by CTPs characteristics, cyclic forms of the growth hormones can also be utilized.

In some embodiments, the hGH modified by CTPs of present invention are biochemically synthesized such as by using standard solid phase techniques. In some embodiments, these biochemical methods include exclusive solid phase synthesis, partial solid phase synthesis, fragment condensation, or classical solution synthesis. In some embodiments, these methods are used when the growth hormones are relatively short (about 5-15 kDa) and/or when it cannot be produced by recombinant techniques (i.e., not encoded by a nucleic acid sequence) and therefore involves different chemistry.

In some embodiments, solid phase hGH modified by CTPs synthesis procedures are well known to one skilled in the art and further described by John Morrow Stewart and Janis Dillaha Young, Solid Phase Polypeptide Syntheses (2nd Ed., Pierce Chemical Company, 1984). In some embodiments, synthetic polypeptides are purified by preparative high performance liquid chromatography [Creighton T. (1983) Proteins, structures and molecular principles. WH Freeman and Co. N.Y.] and the composition of which can be confirmed via amino acid sequencing by methods known to one skilled in the art.

In some embodiments, recombinant protein techniques are used to generate the hGH modified by CTPs of the present invention. In some embodiments, recombinant protein techniques are used for generation of relatively long polypeptides (e.g., longer than 18-25 amino acid). In some embodiments, recombinant protein techniques are used for the generation of large amounts of the hGH modified by CTPs of the present invention. In some embodiments, recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

In another embodiment, hGH modified by CTPs of the present invention are synthesized using a polynucleotide encoding a polypeptide of the present invention. In another embodiment, the polynucleotide encoding hGH modified by CTPs of the present invention is ligated into an expression vector, comprising a transcriptional control of a cis-regulatory sequence (e.g., promoter sequence). In another embodiment, the cis-regulatory sequence is suitable for directing constitutive expression of the growth hormones of the present invention. In another embodiment, the cis-regulatory sequence is suitable for directing tissue specific expression of the hGH modified by CTPs of the present invention. In another embodiment, the cis-regulatory sequence is suitable for directing inducible expression of the hGH modified by CTPs of the present invention.

In another embodiment, tissue-specific promoters suitable for use with the present invention include sequences which are functional in specific cell population, example include, but are not limited to promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264, 166). Inducible promoters suitable for use with the present invention include for example the tetracycline-inducible promoter (Srour, M. A., et al., 2003. Thromb. Haemost. 90: 398-405).

In one embodiment, the phrase "a polynucleotide" refers to a single or double stranded nucleic acid sequence which be isolated and provided in the form of an RNA sequence, a complementary polynucleotide sequence (cDNA), a genomic polynucleotide sequence and/or a composite polynucleotide sequences (e.g., a combination of the above).

In one embodiment, "complementary polynucleotide sequence" refers to a sequence, which results from reverse transcription of messenger RNA using a reverse transcriptase or any other RNA dependent DNA polymerase. In one embodiment, the sequence can be subsequently amplified in vivo or in vitro using a DNA polymerase.

In one embodiment, "genomic polynucleotide sequence" refers to a sequence derived (isolated) from a chromosome and thus it represents a contiguous portion of a chromosome.

In one embodiment, "composite polynucleotide sequence" refers to a sequence, which is at least partially complementary and at least partially genomic. In one embodiment, a composite sequence can include some exonal sequences required to encode the polypeptide of the present invention, as well as some intronic sequences interposing there between. In one embodiment, the intronic sequences can be of any source, including of other genes, and typically will include conserved splicing signal sequences. In one embodiment, intronic sequences include cis acting expression regulatory elements.

In another embodiment, polynucleotides of the present invention are prepared using PCR techniques as described in Example 1, or any other method or procedure known to one skilled in the art. In some embodiments, the procedure involves the ligation of two different DNA sequences (See, for example, "Current Protocols in Molecular Biology", eds. Ausubel et al., John Wiley & Sons, 1992).

In one embodiment, polynucleotides of the present invention are inserted into expression vectors (i.e., a nucleic acid construct) to enable expression of the recombinant polypeptide. In one embodiment, the expression vector of the present invention includes additional sequences which render this vector suitable for replication and integration in prokaryotes. In one embodiment, the expression vector of the present invention includes additional sequences which render this vector suitable for replication and integration in eukaryotes. In one embodiment, the expression vector of the present invention includes a shuttle vector which renders this vector suitable for replication and integration in both prokaryotes and eukaryotes. In another embodiment, cloning vectors comprise transcription and translation initiation sequences (e.g., promoters, enhances) and transcription and translation terminators (e.g., polyadenylation signals).

In one embodiment, a variety of prokaryotic or eukaryotic cells can be used as host-expression systems to express the hGH modified by CTPs of the present invention. In some embodiments, these include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

In another embodiment, non-bacterial expression systems are used (e.g. mammalian expression systems such as CHO cells) to express the growth hormones of the present invention. In one embodiment, the expression vector used to express polynucleotides of the present invention in mammalian cells is pCI-DHFR vector comprising a CMV promoter and a neomycin resistance gene. Construction of the pCI-dhfr vector is described, according to one embodiment, in Example 1.

In another embodiment, in bacterial systems of the present invention, a number of expression vectors can be advantageously selected depending upon the use intended for the polypeptide expressed. In one embodiment, large quantities of polypeptide are desired. In one embodiment, vectors that direct the expression of high levels of the protein product, possibly as a fusion with a hydrophobic signal sequence, which directs the expressed product into the periplasm of the bacteria or the culture medium where the protein product is readily purified are desired. In one embodiment, certain fusion protein engineered with a specific cleavage site to aid in recovery of the polypeptide. In one embodiment, vectors adaptable to such manipulation include, but are not limited to, the pET series of E. coli expression vectors [Studier et al., Methods in Enzymol. 185:60-89 (1990)].

In one embodiment, yeast expression systems are used. In one embodiment, a number of vectors containing constitutive or inducible promoters can be used in yeast as disclosed in U.S. Pat. No. 5,932,447. In another embodiment, vectors which promote integration of foreign DNA sequences into the yeast chromosome are used.

In one embodiment, the expression vector of the present invention can further include additional polynucleotide sequences that allow, for example, the translation of several proteins from a single mRNA such as an internal ribosome entry site (IRES) and sequences for genomic integration of the promoter-chimeric polypeptide.

In another embodiment, mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

In another embodiment, expression vectors containing regulatory elements from eukaryotic viruses such as retroviruses are used by the present invention. SV40 vectors include pSVT7 and pMT2. In some embodiments, vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In another embodiment, recombinant viral vectors are useful for in vivo expression of the GH modified by CTPs of the present invention since they offer advantages such as lateral infection and targeting specificity. In one embodiment, lateral infection is inherent in the life cycle of, for example, retrovirus and is the process by which a single infected cell produces many progeny virions that bud off and infect neighboring cells. In another embodiment, the result is that a large area becomes rapidly infected, most of which was not initially infected by the original viral particles. In one embodiment, viral vectors are produced that are unable to spread laterally. In another embodiment, this characteristic can be useful if the desired purpose is to introduce a specified gene into only a localized number of targeted cells.

In another embodiment, various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In another embodiment, introduction of nucleic acid by viral infection offers several advantages over other methods such as lipofection and electroporation, since higher transfection efficiency can be obtained due to the infectious nature of viruses.

In one embodiment, it will be appreciated that the GH modified by CTPs of the present invention can also be expressed from a nucleic acid construct administered to the individual employing any suitable mode of administration, described hereinabove (i.e., in-vivo gene therapy). In one embodiment, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex-vivo gene therapy).

In one embodiment, in vivo gene therapy using a growth hormone has been conducted in animal models.

In one embodiment, plant expression vectors are used. In one embodiment, the expression of a polypeptide coding sequence is driven by a number of promoters. In some embodiments, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

Various methods, in some embodiments, can be used to introduce the expression vector of the present invention into the host cell system. In some embodiments, such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In one embodiment, transformed cells are cultured under effective conditions, which allow for the expression of high amounts of recombinant polypeptide. In another embodiment, effective culture conditions include, but are not limited to, effective media, bioreactor, temperature, pH and oxygen conditions that permit protein production. In one embodiment, an effective medium refers to any medium in which a cell is cultured to produce the recombinant polypeptide of the present invention. In another embodiment, a medium typically includes an aqueous solution having assimilable carbon, nitrogen and phosphate sources, and appropriate salts, minerals, metals and other nutrients, such as vitamins. In another embodiment, cells of the present invention can be cultured in conventional fermentation bioreactors, shake flasks, test tubes, microtiter dishes and petri plates. In another embodiment, culturing is carried out at a temperature, pH and oxygen content appropriate for a recombinant cell. In another embodiment, culturing conditions are within the expertise of one of ordinary skill in the art.

In another embodiment, depending on the vector and host system used for production, resultant growth hormones of the present invention either remain within the recombinant cell, secreted into the fermentation medium, secreted into a space between two cellular membranes, such as the periplasmic space in $E.$ $coli$; or retained on the outer surface of a cell or viral membrane.

In one embodiment, following a predetermined time in culture, recovery of the recombinant polypeptide is effected.

In one embodiment, the phrase "recovering the recombinant polypeptide" used herein refers to collecting the whole fermentation medium containing the polypeptide and need not imply additional steps of separation or purification.

In one embodiment, growth hormones of the present invention are purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In one embodiment, to facilitate recovery, the expressed coding sequence can be engineered to encode the polypeptide of the present invention and fused cleavable moiety. In one embodiment, a fusion protein can be designed so that the polypeptide can be readily isolated by affinity chromatography; e.g., by immobilization on a column specific for the cleavable moiety. In one embodiment, a cleavage site is engineered between the polypeptide and the cleavable moiety and the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

In one embodiment, the polypeptide of the present invention is retrieved in "substantially pure" form.

In one embodiment, the phrase "substantially pure" refers to a purity that allows for the effective use of the protein in the applications described herein.

In one embodiment, the polypeptide of the present invention can also be synthesized using in vitro expression systems. In one embodiment, in vitro synthesis methods are well known in the art and the components of the system are commercially available.

In one embodiment, production of GH modified by CTPs using recombinant DNA technology is performed.

In another embodiment, the recombinant polypeptides are synthesized and purified; their therapeutic efficacy can be assayed either in vivo or in vitro. In one embodiment, the binding activities of the recombinant GH modified by CTPs of the present invention can be ascertained using various assays.

In one embodiment, the present invention comprises CTP-hGH-CTP-CTP polypeptides. In one embodiment, recombinant DNA technology methods are used for the production of CTP-hGH-CTP-CTP polypeptides as illustrated in Example 1. In one embodiment, the therapeutic efficacy of the CTP-hGH-CTP-CTP polypeptides of the present invention is assayed either in vivo. In one embodiment, the therapeutic efficacy of the CTP-hGH-CTP-CTP polypeptides of the present invention is assayed either in vitro. In one embodiment, the binding activities of the recombinant hGH polypeptides of the present invention are measured using Nb2 (a prolactin-dependent rat lymphoma cell line (ECACC Cell Bank)) or a FCD-P1 murine cell line, previously transfected with human growth hormone receptor. In one embodiment, binding of hGH to these receptors induces cell proliferation which in one embodiment is measured by the levels of MTT cellular stain as a function of hGH activity. In one embodiment, in vivo activity is deduced by measuring weight gain over time in treated growth hormone deficient animals.

In one embodiment, the present invention provides a method of inducing growth or weight gain in a subject, comprising administering to the subject a therapeutically effective amount of a polypeptide comprising a growth hormone, one chorionic gonadotrophin carboxy terminal peptide (CTP) attached to an amino terminus of said growth hormone, and two chorionic gonadotrophin CTPs attached to a carboxy terminus of the growth hormone, thereby inducing growth or weight gain in a subject.

In another embodiment, the present invention provides a method of inducing growth in a human subject, comprising administering to said subject a therapeutically effective amount of a polypeptide comprising a growth hormone, one chorionic gonadotrophin carboxy terminal peptide (CTP) attached to the amino terminus of said growth hormone, and two chorionic gonadotrophin CTPs attached to the carboxy terminus of said growth hormone, thereby inducing growth in said subject. In one embodiment, said human subject is an adolescent. In another embodiment, the human subject is a child. In another embodiment, the human subject is a GH-deficient child.

In another embodiment, the present invention provides a method of inducing weight gain in a human subject, comprising administering to said subject a therapeutically effective amount of a polypeptide comprising a growth hormone, one chorionic gonadotrophin carboxy terminal peptide (CTP) attached to the amino terminus of said growth hormone, and two chorionic gonadotrophin CTPs attached to the carboxy terminus of said growth hormone, thereby inducing weight gain in said subject. In one embodiment, said human subject is an adolescent. In another embodiment, the human subject is a child. In another embodiment, the human subject is a GH-deficient child.

In another embodiment, the present invention provides a method of inducing weight loss or decreasing body fat in a human subject, comprising administering to said subject a therapeutically effective amount of a polypeptide comprising a growth hormone, one chorionic gonadotrophin carboxy terminal peptide (CTP) attached to the amino terminus of said growth hormone, and two chorionic gonadotrophin CTPs attached to the carboxy terminus of said growth hormone, thereby inducing weight loss or decreasing body fat in said subject. In one embodiment, said subject is obese. In another embodiment, the subject is overweight. In another embodiment, the human subject is an adult. In another embodiment, the human subject is a GH-deficient adult.

In another embodiment, the present invention provides a method of decreasing fat deposits in a subject. In another embodiment, the present invention provides a method of increasing muscle mass in a subject. In another embodiment, the present invention provides a method of promoting muscle growth in a subject. In another embodiment, the human subject is an adult. In another embodiment, the human subject is a GH-deficient adult. In another embodiment, the present invention provides a method of increasing muscle to fat ratio. In another embodiment, the present invention provides a method of decreasing body mass index (BMI) or Quetelet index.

In another embodiment, provided herein a method of inducing growth in a subject comprising administering to a subject a growth hormone modified by CTPs as described herein. In one embodiment, the CTP-modified growth hormone is directly administered to the subject, while in another embodiment, a polynucleotide encoding said CTP-modified growth hormone is administered to the subject. In another embodiment, provided herein a method of inducing growth in a subject comprising administering to a subject a composition consisting known excipients, known vehicles, and a polypeptide comprising a growth hormone, one chorionic gonadotrophin carboxy terminal peptide (CTP) attached to an amino terminus of the growth hormone, and two chorionic gonadotrophin carboxy terminal peptides attached to a carboxy terminus of the growth hormone. In another embodiment, provided herein a method of inducing growth in a subject comprising administering to a subject a composition consisting known excipients, known vehicles, and a polypeptide consisting a growth hormone, one chorionic gonadotrophin carboxy terminal peptide (CTP) attached to an amino terminus of the growth hormone, and two chorionic gonadotrophin carboxy terminal peptides attached to a carboxy terminus of the growth hormone.

In another embodiment, growth is measured by weight gain. In another embodiment, growth is measured by height gain. In another embodiment, growth is measured by weight gain. In another embodiment, growth is measured by muscle mass gain. In another embodiment, growth is measured by weight gain. In another embodiment, growth is measured by bone mass gain. In another embodiment, growth is measured by weight gain. In another embodiment, growth is measured by fat gain. In another embodiment, growth is measured by any known measure known to one of skill in the art. In another embodiment, the subject wherein growth is measured is a child. In another embodiment, the subject wherein growth is measured is a GH-deficient child.

In another embodiment, polypeptides comprising GH modified by CTPs of the present invention are administered in a dose of 1-90 micrograms in 0.1-5 ml solution. In another embodiment, polypeptides comprising GH modified by CTPs are administered in a dose of 1-50 micrograms in 0.1-5 ml solution. In another embodiment, polypeptides comprising GH modified by CTPs are administered in a dose of 1-25 micrograms in 0.1-5 ml solution. In another embodiment, polypeptides comprising GH modified by CTPs are administered in a dose of 50-90 micrograms in 0.1-5 ml solution. In another embodiment, polypeptides comprising GH modified by CTPs are administered in a dose of 10-50 micrograms in 0.1-5 ml solution.

In another embodiment, polypeptides comprising GH modified by CTPs are administered in a dose of 1-90 micrograms in 0.1-5 ml solution by intramuscular (IM) injection, subcutaneous (SC) injection, or intravenous (IV) injection once a week. In another embodiment, polypeptides comprising GH modified by CTPs are administered in a dose of 1-90 micrograms in 0.1-5 ml solution by intramuscular (IM) injection, subcutaneous (SC) injection, or intravenous (IV) injection twice a week. In another embodiment, polypeptides comprising GH modified by CTPs are administered in a dose of 1-90 micrograms in 0.1-5 ml solution by intramuscular (IM) injection, subcutaneous (SC) injection, or intravenous (IV) injection three times a week. In another embodiment, polypeptides comprising GH modified by CTPs are administered in a dose of 1-90 micrograms in 0.1-5 ml solution by intramuscular (IM) injection, subcutaneous (SC) injection, or intravenous (IV) injection once every two weeks. In another embodiment, polypeptides comprising GH modified by CTPs are administered in a dose of 1-90 micrograms in 0.1-5 ml solution by intramuscular (IM) injection, subcutaneous (SC) injection, or intravenous (IV) injection once every 17 days. In another embodiment, polypeptides comprising GH modified by CTPs are administered in a dose of 1-90 micrograms in 0.1-5 ml solution by intramuscular (IM) injection, subcutaneous (SC) injection, or intravenous (IV) injection once every 19 days weeks.

In another embodiment, protein drugs of molecular weight lower than 50,000 daltons, such as GH modified by CTPs of the present invention are in general short-lived species in vivo, having short circulatory half-lives of several hours. In another embodiment, the subcutaneous route of administration in general provides slower release into the circulation. In another embodiment, the CTP modified polypeptide of the invention prolongs the half-live of protein drugs of molecular weight lower than 50,000 daltons, such as GH. In another embodiment, the CTP modified polypeptide of the invention enable GH to exert its beneficial effects for a longer period of time.

In another embodiment, the immunogenicity of a CTP modified polypeptide comprising a GH modified by CTPs is equal to an isolated GH. In another embodiment, the immunogenicity of a CTP modified polypeptide comprising a GH modified by CTPs is comparable to an isolated GH. In another embodiment, modifying a GH as described herein with CTP peptides reduces the immunogenicity of the GH. In another embodiment, the CTP modified polypeptide comprising a GH is as active as an isolated GH protein. In another embodiment, the CTP modified polypeptide comprising a GH is more active than an isolated GH. In another embodiment, the CTP modified polypeptide comprising a GH maximizes the growth hormone's protective ability against degradation while minimizing reductions in bioactivity.

In another embodiment, the GH modified by CTPs of the present invention is provided to the individual per se. In one embodiment, the GH modified by CTPs of the present invention is provided to the individual as part of a pharmaceutical composition where it is mixed with a pharmaceutically acceptable carrier.

In another embodiment, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

In another embodiment, "active ingredient" refers to the polypeptide sequence of interest, which is accountable for the biological effect.

In one embodiment, the present invention provides combined preparations. In one embodiment, "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In another embodiment, the parts of the kit of parts can then, e.g., be administered simultaneously or chronologically staggered, that is at different time points and with equal or different time intervals for any part of the kit of parts. The ratio of the total amounts of the combination partners can be administered in the combined preparation. The combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

In another embodiment, the phrases "physiologically acceptable carrier" and "pharmaceutically acceptable carrier" which be interchangeably used refer to a carrier or a diluent that does not cause significant irritation to an organism and does not abrogate the biological activity and properties of the administered compound. An adjuvant is included under these phrases. In one embodiment, one of the ingredients included in the pharmaceutically acceptable carrier can be for example polyethylene glycol (PEG), a biocompatible polymer with a wide range of solubility in both organic and aqueous media (Mutter et al. (1979).

In another embodiment, "excipient" refers to an inert substance added to a pharmaceutical composition to further facilitate administration of an active ingredient. In one embodiment, excipients include calcium carbonate, calcium phosphate, various sugars and types of starch, cellulose derivatives, gelatin, vegetable oils and polyethylene glycols.

Techniques for formulation and administration of drugs are found in "Remington's Pharmaceutical Sciences," Mack Publishing Co., Easton, Pa., latest edition, which is incorporated herein by reference.

In another embodiment, suitable routes of administration, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections.

In another embodiment, the preparation is administered in a local rather than systemic manner, for example, via injection of the preparation directly into a specific region of a patient's body.

Various embodiments of dosage ranges are contemplated by this invention. The dosage of the GH modified by CTPs of the present invention, in one embodiment, is in the range of 0.005-100 mg/day. In another embodiment, the dosage is in the range of 0.005-5 mg/day. In another embodiment, the dosage is in the range of 0.01-50 mg/day. In another embodiment, the dosage is in the range of 0.1-20 mg/day. In another embodiment, the dosage is in the range of 0.1-10 mg/day. In another embodiment, the dosage is in the range of 0.01-5 mg/day. In another embodiment, the dosage is in the range of 0.001-0.01 mg/day. In another embodiment, the dosage is in the range of 0.001-0.1 mg/day. In another embodiment, the dosage is in the range of 0.1-5 mg/day. In another embodiment, the dosage is in the range of 0.5-50 mg/day. In another embodiment, the dosage is in the range of 0.2-15 mg/day. In another embodiment, the dosage is in the range of 0.8-65 mg/day. In another embodiment, the dosage is in the range of 1-50 mg/day. In another embodiment, the dosage is in the range of 5-10 mg/day. In another embodiment, the dosage is in the range of 8-15 mg/day. In another embodiment, the dosage is in a range of 10-20 mg/day. In another embodiment, the dosage is in the range of 20-40 mg/day. In another embodiment, the dosage is in a range of 60-120 mg/day. In another embodiment, the dosage is in the range of 12-40 mg/day. In another embodiment, the dosage is in the range of 40-60 mg/day. In another embodiment, the dosage is in a range of 50-100 mg/day. In another embodiment, the dosage is in a range of 1-60 mg/day. In another embodiment, the dosage is in the range of 15-25 mg/day. In another embodiment, the dosage is in the range of 5-10 mg/day. In another embodiment, the dosage is in the range of 55-65 mg/day. In another embodiment, the dosage is in the range of 1-5 mg/day.

The dosage of the GH modified by CTPs of the present invention, in one embodiment, is in the range of 0.005-100 mg/week. In another embodiment, the dosage is in the range of 0.005-5 mg/week. In another embodiment, the dosage is in the range of 0.01-50 mg/week. In another embodiment, the dosage is in the range of 0.05-7.2 mg/week. In another embodiment, the dosage is in the range of 0.05-7.2 mg/week. In another embodiment, the dosage is in the range of 0.05-7.2 mg/week. In another embodiment, the dosage is in the range of 0.1-20 mg/week. In another embodiment, the dosage is in the range of 0.1-10 mg/week. In another embodiment, the dosage is in the range of 0.01-5 mg/week. In another embodiment, the dosage is in the range of 0.001-0.01 mg/week. In another embodiment, the dosage is in the range of 0.001-0.1 mg/week. In another embodiment, the dosage is in the range of 0.1-5 mg/week. In another embodiment, the dosage is in the range of 0.5-50 mg/week. In another embodiment, the dosage is in the range of 0.2-15 mg/week. In another embodiment, the dosage is in the range of 0.26-10.7 mg/week. In another embodiment, the dosage is in the range of 0.8-65 mg/week. In another embodiment, the dosage is in the range of 1-50 mg/week. In another embodiment, the dosage is in the range of 5-10 mg/week. In another embodiment, the dosage is in the range of 8-15 mg/week. In another embodiment, the dosage is in a range of 10-20 mg/week. In another embodiment, the dosage is in the range of 20-40 mg/week. In another embodiment, the dosage is in a range of 60-120 mg/week. In another embodiment, the dosage is in the range of 12-40 mg/week. In another embodiment, the dosage is in the range of 40-60 mg/week. In another embodiment, the dosage is in a range of 50-100 mg/week. In another embodiment, the dosage is in a range of 1-60 mg/week. In another embodiment, the dosage is in the range of 15-25 mg/week. In another embodiment, the dosage is in the range of 5-10 mg/week. In another embodiment, the dosage is in the range of 55-65 mg/week. In another embodiment, the dosage is in the range of 1-5 mg/week.

In another embodiment, the GH dosage given to a subject is 50% of the standard dosage given to a reference subject from the same population of subjects (e.g. children, elderly, men, women, GH deficient, specific nationality, etc). In another embodiment, the dosage is 30% of the dosage given to a subject from a specific population of subjects. In another embodiment, the dosage is 45% of the dosage given to a subject from a specific population of subjects. In another embodiment, the dosage is 100% of the dosage given to a subject from a specific population of subjects.

In another embodiment, the dosage is 1-5 mg/week. In another embodiment, the dosage is 2 mg/week. In another embodiment, the dosage is 4 mg/week. In another embodiment, the dosage is 1.2 mg/week. In another embodiment, the dosage is 1.8 mg/week. In another embodiment, the dosage is approximately the dosages described herein.

In another embodiment, the dosage is 1-5 mg/administration. In another embodiment, the dosage is 2 mg/administration. In another embodiment, the dosage is 4 mg/administration. In another embodiment, the dosage is 1.2 mg/administration. In another embodiment, the dosage is 1.8 mg/administration. In one embodiment, the composition is administered once a week. In another embodiment, the composition is administered once biweekly. In another embodiment, the composition is administered monthly. In another embodiment, the composition is administered daily.

In another embodiment, GH modified by CTPs is formulated in an intranasal dosage form. In another embodiment, GH modified by CTPs is formulated in an injectable dosage form. In another embodiment, GH modified by CTPs is administered to a subject in a dose ranging from 0.0001 mg to 0.6 mg. In another embodiment, GH modified by CTPs is administered to a subject in a dose ranging from 0.001 mg to 0.005 mg. In another embodiment, GH modified by CTPs is administered to a subject in a dose ranging from 0.005 mg to 0.01 mg. In another embodiment, GH modified by CTPs is administered to a subject in a dose ranging from 0.01 mg to 0.3 mg. In another embodiment, a GH modified by CTPs is administered to a subject in a dose in a dose ranging from 0.2 mg to 0.6 mg.

In another embodiment, GH modified by CTPs is administered to a subject in a dose ranging from 1-100 micrograms. In another embodiment, a GH modified by CTPs is administered to a subject in a dose ranging from 10-80 micrograms. In another embodiment, a GH modified by CTPs is administered to a subject in a dose ranging from 20-60 micrograms. In another embodiment, a GH modified by CTPs is administered to a subject in a dose ranging from 10-50 micrograms. In another embodiment, a GH modified by CTPs is administered to a subject in a dose ranging from 40-80 micrograms. In another embodiment, a GH modified by CTPs is administered to a subject in a dose ranging from 10-30 micrograms. In another embodiment, a GH modified by CTPs is administered to a subject in a dose ranging from 30-60 micrograms.

In another embodiment, GH modified by CTPs is administered to a subject in a dose ranging from 0.2 mg to 2 mg. In another embodiment, a GH modified by CTPs is administered to a subject in a dose ranging from 2 mg to 6 mg. In another embodiment, a GH modified by CTPs is administered to a subject in a dose ranging from 4 mg to 10 mg. In another embodiment, a GH modified by CTPs is administered to a subject in a dose ranging from 5 mg and 15 mg.

In another embodiment, a GH modified by CTPs is injected into the muscle (intramuscular injection). In another embodiment, a GH modified by CTPs is injected below the skin (subcutaneous injection). In another embodiment, a GH modified by CTPs is injected into the muscle. In another embodiment, a GH modified by CTPs is injected below the skin.

In another embodiment, the methods of the invention include increasing the compliance in the use of GH therapy, comprising providing to a subject in need thereof, a GH modified by CTPs, thereby increasing compliance in the use of growth hormone therapy.

In another embodiment, the methods of the invention include increasing the compliance of patients afflicted with chronic illnesses that are in need of a GH therapy. In another embodiment, the methods of the invention enable reduction in the dosing frequency of a GH by modifying the GH with CTPs as described hereinabove. In another embodiment, the term compliance comprises adherence. In another embodiment, the methods of the invention include increasing the compliance of patients in need of a GH therapy by reducing the frequency of administration of the GH. In another embodiment, reduction in the frequency of administration of the GH is achieved due to the CTP modifications which render the CTP-modified GH more stable. In another embodiment, reduction in the frequency of administration of the GH is achieved as a result of increasing T½ of the growth hormone. In another embodiment, reduction in the frequency of administration of the GH is achieved as a result of increasing the clearance time of the GH. In another embodiment, reduction in the frequency of administration of the growth hormone is achieved as a result of increasing the AUC measure of the growth hormone.

Thus, in another embodiment, the present invention further provides a method of improving the area under the curve (AUC) of a growth hormone, comprising the step of attaching one chorionic gonadotrophin carboxy terminal peptide to an amino terminus of the growth hormone and two chorionic gonadotrophin carboxy terminal peptides to a carboxy terminus of the growth hormone, thereby improving the area under the curve (AUC) of a growth hormone.

Thus, in another embodiment, the present invention further provides a method of reducing a dosing frequency of a growth hormone, comprising the step of attaching one chorionic gonadotrophin carboxy terminal peptide to an amino terminus of the growth hormone and two chorionic gonadotrophin carboxy terminal peptides to a carboxy terminus of the growth hormone, thereby reducing a dosing frequency of a growth hormone.

Thus, in another embodiment, the present invention provides a method of increasing compliance in the use of growth hormone therapy in a subject in need thereof, comprising providing to said subject a polypeptide comprising a growth hormone, one chorionic gonadotrophin carboxy terminal peptide (CTP) attached to the amino terminus of said growth hormone, and two chorionic gonadotrophin carboxy terminal peptides attached to the carboxy terminus of said growth hormone, thereby increasing compliance in the use of growth hormone therapy. In one embodiment, said subject is human.

In another embodiment, the present invention provides a method of increasing insulin-like growth factor (IGF-1) levels in a human subject, comprising administering to said subject a therapeutically effective amount of a polypeptide comprising a growth hormone, one chorionic gonadotrophin carboxy terminal peptide (CTP) attached to the amino terminus of said growth hormone, and two chorionic gonadotrophin CTPs attached to the carboxy terminus of said growth hormone, thereby increasing IGF-1 levels in said subject. In another embodiment, methods of increasing IGF-1 levels are provided in Example 6, herein below.

In another embodiment, the present invention provides a method of increasing insulin-like growth factor (IGF-1) levels to a desired therapeutic range in a human subject, comprising administering to the subject a therapeutically effective amount of a polypeptide comprising a growth hormone, one chorionic gonadotrophin carboxy terminal peptide (CTP) attached to the amino terminus of the growth hormone, and two chorionic gonadotrophin CTPs attached to the carboxy terminus of said growth hormone, thereby increasing IGF-1 levels to a desired therapeutic range in the subject. In another embodiment, the human subject is an adult. In another embodiment, the human subject is a GH-deficient adult. In another embodiment, the human subject is a normal adult. In another embodiment, methods of increasing IGF-1 levels to a desired therapeutic level are provided in Example 9, herein below.

In one embodiment, the present invention provides a method of maintaining insulin-like growth factor (IGF-1) levels within a normal therapeutic range in a subject, the method comprising administering to the subject a therapeutically effective amount of a polypeptide comprising a growth hormone, one chorionic gonadotrophin carboxy terminal peptide (CTP) attached to the amino terminus of the growth hormone, and two chorionic gonadotrophin CTPs attached to the carboxy terminus of the growth hormone, thereby maintaining IGF-I levels within a normal therapeutic range in the subject. In another embodiment, methods of maintaining IGF-1 levels within a normal therapeutic level are provided in Example 9, herein below.

In one embodiment, increasing IGF-1 levels in a human subject may be effective in treating, preventing or suppressing type 1 diabetes, type 2 diabetes, amyotrophic lateral sclerosis (ALS aka "Lou Gehrig's Disease"), severe burn injury and myotonic muscular dystrophy (MMD). In another embodiment, maintaining IGF-1 levels in a normal therapeutic range in a human subject may be effective in treating, preventing or suppressing type 1 diabetes, type 2 diabetes, amyotrophic lateral sclerosis (ALS aka "Lou Gehrig's Disease"), severe burn injury and myotonic muscular dystrophy (MMD).

In one embodiment, the desired therapeutic range is defined as between +/−2 standard deviations through −2 standard deviations from the average IGF-1 levels expected in a normal population, stratified by age group and gender, as further provided herein below (see Example 9). In addition, the trial measured IGF-1 levels within a narrower range of +/−1.5 standard deviations for the purpose of observing the variance of the patients within the normal range (see Example 9, herein below).

In another embodiment, a GH modified by CTPs is administered to a subject once a day. In another embodiment, a polypeptide comprising a GH modified by CTPs is administered to a subject once every two days. In another embodiment, a GH modified by CTPs is administered to a subject once every three days. In another embodiment, a GH modified by CTPs is administered to a subject once every four days. In another embodiment, a GH modified by CTPs is administered to a subject once every five days. In another embodiment, a GH modified by CTPs is administered to a subject once every six days. In another embodiment, a GH modified by CTPs is administered to a subject once every week. In another embodiment, a GH modified by CTPs is administered to a subject once every 7-14 days. In another embodiment, a GH modified by CTPs is administered to a subject once every 10-20 days. In another embodiment, a GH modified by CTPs is administered to a subject once every 5-15 days. In another embodiment, a GH modified by CTPs is administered to a subject once every 15-30 days.

In another embodiment, the dosage is in a range of 50-500 mg/day. In another embodiment, the dosage is in a range of 50-150 mg/day. In another embodiment, the dosage is in a range of 100-200 mg/day. In another embodiment, the dosage is in a range of 150-250 mg/day. In another embodiment, the dosage is in a range of 200-300 mg/day. In another embodiment, the dosage is in a range of 250-400 mg/day. In another embodiment, the dosage is in a range of 300-500 mg/day. In another embodiment, the dosage is in a range of 350-500 mg/day.

In one embodiment, the dosage is 20 mg/day. In one embodiment, the dosage is 30 mg/day. In one embodiment, the dosage is 40 mg/day. In one embodiment, the dosage is 50 mg/day. In one embodiment, the dosage is 0.01 mg/day. In another embodiment, the dosage is 0.1 mg/day. In another embodiment, the dosage is 1 mg/day. In another embodiment, the dosage is 0.530 mg/day. In another embodiment, the dosage is 0.05 mg/day. In another embodiment, the dosage is 50 mg/day. In another embodiment, the dosage is 10 mg/day. In another embodiment, the dosage is 20-70 mg/day. In another embodiment, the dosage is 5 mg/day.

In another embodiment, the dosage is 1-90 mg/day. In another embodiment, the dosage is 1-90 mg/2 days. In another embodiment, the dosage is 1-90 mg/3 days. In another embodiment, the dosage is 1-90 mg/4 days. In another embodiment, the dosage is 1-90 mg/5 days. In another embodiment, the dosage is 1-90 mg/6 days. In another embodiment, the dosage is 1-90 mg/week. In another embodiment, the dosage is 1-90 mg/9 days. In another embodiment, the dosage is 1-90 mg/11 days. In another embodiment, the dosage is 1-90 mg/14 days.

In another embodiment, the growth hormone dosage is 10-50 mg/day. In another embodiment, the dosage is 10-50 mg/2 days. In another embodiment, the dosage is 10-50 mg/3 days. In another embodiment, the dosage is 10-50 mg/4 days. In another embodiment, the dosage is 10-50 micrograms mg/5 days. In another embodiment, the dosage is 10-50 mg/6 days. In another embodiment, the dosage is 10-50 mg/week. In another embodiment, the dosage is 10-50 mg/9 days. In another embodiment, the dosage is 10-50 mg/11 days. In another embodiment, the dosage is 10-50 mg/14 days.

Oral administration, in one embodiment, comprises a unit dosage form comprising tablets, capsules, lozenges, chewable tablets, suspensions, emulsions and the like. Such unit dosage forms comprise a safe and effective amount of the desired growth hormone of the invention, each of which is in one embodiment, from about 0.7 or 3.5 mg to about 280 mg/70 kg, or in another embodiment, about 0.5 or 10 mg to about 210 mg/70 kg. The pharmaceutically-acceptable carriers suitable for the preparation of unit dosage forms for peroral administration are well-known in the art. In some embodiments, tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. In one embodiment, glidants such as silicon dioxide can be used to improve flow characteristics of the powder-mixture. In one embodiment, coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. In some embodiments, the selection of carrier components depends on secondary considerations like taste, cost, and shelf stability, which are not critical for the purposes of this invention, and can be readily made by a person skilled in the art.

In one embodiment, the oral dosage form comprises predefined release profile. In one embodiment, the oral dosage form of the present invention comprises an extended release tablets, capsules, lozenges or chewable tablets. In one embodiment, the oral dosage form of the present invention comprises a slow release tablets, capsules, lozenges or chewable tablets. In one embodiment, the oral dosage form of the present invention comprises an immediate release tablets, capsules, lozenges or chewable tablets. In one embodiment, the oral dosage form is formulated according to the desired release profile of the pharmaceutical active ingredient as known to one skilled in the art.

Peroral compositions, in some embodiments, comprise liquid solutions, emulsions, suspensions, and the like. In some embodiments, pharmaceutically-acceptable carriers suitable for preparation of such compositions are well known in the art. In some embodiments, liquid oral compositions comprise from about 0.001% to about 0.933% of the desired compound or compounds, or in another embodiment, from about 0.01% to about 10%.

In some embodiments, compositions for use in the methods of this invention comprise solutions or emulsions, which in some embodiments are aqueous solutions or emulsions comprising a safe and effective amount of the compounds of the present invention and optionally, other compounds, intended for topical intranasal administration. In some embodiments, h compositions comprise from about 0.001% to about 10.0% w/v of a GH modified by CTPs, more preferably from about 00.1% to about 2.0, which is used for systemic delivery of the compounds by the intranasal route.

In another embodiment, the pharmaceutical compositions are administered by intravenous, intra-arterial, or intramuscular injection of a liquid preparation. In some embodiments, liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intra-arterially, and are thus formulated in a form suitable for intra-arterial administration. In another embodiment, the pharmaceutical compositions are administered intramuscularly, and are thus formulated in a form suitable for intramuscular administration.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the compounds of the present invention are combined with an additional appropriate therapeutic agent or agents, prepared and applied as solutions, suspensions, or emulsions in a physiologically acceptable diluent with or without a pharmaceutical carrier.

In one embodiment, pharmaceutical compositions of the present invention are manufactured by processes well known in the art, e.g., by means of conventional mixing, dissolving, granulating, dragee-making, levigating, emulsifying, encapsulating, entrapping or lyophilizing processes.

In one embodiment, pharmaceutical compositions for use in accordance with the present invention is formulated in conventional manner using one or more physiologically acceptable carriers comprising excipients and auxiliaries, which facilitate processing of the active ingredients into preparations which, can be used pharmaceutically. In one embodiment, formulation is dependent upon the route of administration chosen.

In one embodiment, injectables, of the invention are formulated in aqueous solutions. In one embodiment, injectables, of the invention are formulated in physiologically compatible buffers such as Hank's solution, Ringer's solution, or physiological salt buffer. In some embodiments, for transmucosal administration, penetrants appropriate to the barrier to be permeated are used in the formulation. Such penetrants are generally known in the art.

In one embodiment, the preparations described herein are formulated for parenteral administration, e.g., by bolus injection or continuous infusion. In some embodiments, formulations for injection are presented in unit dosage form, e.g., in ampoules or in multidose containers with optionally, an added preservative. In some embodiments, compositions are suspensions, solutions or emulsions in oily or aqueous vehicles, and contain formulatory agents such as suspending, stabilizing and/or dispersing agents.

The compositions also comprise, in some embodiments, preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise, in some embodiments, local anesthetics or other actives. The compositions can be used as sprays, mists, drops, and the like.

In some embodiments, pharmaceutical compositions for parenteral administration include aqueous solutions of the active preparation in water-soluble form. Additionally, suspensions of the active ingredients, in some embodiments, are prepared as appropriate oily or water based injection suspensions. Suitable lipophilic solvents or vehicles include, in some embodiments, fatty oils such as sesame oil, or synthetic fatty acid esters such as ethyl oleate, triglycerides or liposomes. Aqueous injection suspensions contain, in some embodiments, substances, which increase the viscosity of the suspension, such as sodium carboxymethyl cellulose, sorbitol or dextran. In another embodiment, the suspension also contain suitable stabilizers or agents which increase the solubility of the active ingredients to allow for the preparation of highly concentrated solutions.

In another embodiment, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

In another embodiment, the pharmaceutical composition delivered in a controlled release system is formulated for intravenous infusion, implantable osmotic pump, transdermal patch, liposomes, or other modes of administration. In one embodiment, a pump is used (see Langer, supra; Sefton, CRC Crit. Ref. *Biomed. Eng.* 14:201 (1987); Buchwald et al., Surgery 88:507 (1980); Saudek et al., *N. Engl. J. Med.* 321:574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in *Medical Applications of Controlled Release*, supra, vol. 2, pp. 115-138 (1984). Other controlled release systems are discussed in the review by Langer (*Science* 249:1527-1533 (1990).

In some embodiments, the active ingredient is in powder form for constitution with a suitable vehicle, e.g., sterile, pyrogen-free water based solution, before use. Compositions are formulated, in some embodiments, for atomization and inhalation administration. In another embodiment, compositions are contained in a container with attached atomizing means.

In one embodiment, the preparation of the present invention is formulated in rectal compositions such as suppositories or retention enemas, using, e.g., conventional suppository bases such as cocoa butter or other glycerides.

In another embodiment, pharmaceutical compositions suitable for use in context of the present invention include compositions wherein the active ingredients are contained in an amount effective to achieve the intended purpose. In another embodiment, a therapeutically effective amount means an amount of active ingredients effective to prevent, alleviate or ameliorate symptoms of disease or prolong the survival of the subject being treated.

In one embodiment, determination of a therapeutically effective amount is well within the capability of those skilled in the art.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of *theobroma*; polyols such as propylene glycol, glycerine, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically-acceptable carrier to be used in conjunction with the compound is basically determined by the way the compound is to be administered. If the subject compound is to be injected, in one embodiment, the pharmaceutically-acceptable carrier is sterile, physiological saline, with a blood-compatible suspending agent, the pH of which has been adjusted to about 7.4.

In addition, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmellose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), antioxidants (e.g., ascorbic acid, sodium metabisulfite, butylated hydroxyanisole), stabilizers (e.g. hydroxypropyl cellulose, hydroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, cellulose (e.g. Avicel™, RC-591), tragacanth and sodium alginate; typical wetting agents include lecithin and polyethylene oxide sorbitan (e.g. polysorbate 80). Typical preservatives include methyl paraben and sodium benzoate. In another embodiment, peroral liquid compositions also contain one or more components such as sweeteners, flavoring agents and colorants disclosed above.

The compositions also include incorporation of the active material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

In another embodiment, compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. In another embodiment, the modified compounds exhibit substantially longer half-lives in blood following intravenous injection than do the corresponding unmodified compounds. In one embodiment, modifications also increase the compound's solubility in aqueous solution, eliminate aggregation, enhance the physical and chemical stability of the compound, and greatly reduce the immunogenicity and reactivity of the compound. In another embodiment, the desired in vivo biological activity is achieved by the administration of such polymer-compound abducts less frequently or in lower doses than with the unmodified compound.

In another embodiment, preparation of effective amount or dose can be estimated initially from in vitro assays. In one embodiment, a dose can be formulated in animal models and such information can be used to more accurately determine useful doses in humans.

In one embodiment, toxicity and therapeutic efficacy of the active ingredients described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p. 1].

In one embodiment, depending on the severity and responsiveness of the condition to be treated, dosing can be of a single or a plurality of administrations, with course of treatment lasting from several days to several weeks or until cure is effected or diminution of the disease state is achieved.

In one embodiment, the amount of a composition to be administered will, of course, be dependent on the subject being treated, the severity of the affliction, the manner of administration, the judgment of the prescribing physician, etc.

In one embodiment, compositions including the preparation of the present invention formulated in a compatible pharmaceutical carrier are also be prepared, placed in an appropriate container, and labeled for treatment of an indicated condition.

In another embodiment, a GH modified by CTPs is administered via systemic administration. In another embodiment, a growth hormone as described herein is administered by intravenous, intramuscular or subcutaneous injection. In another embodiment, a GH modified by CTPs is lyophilized (i.e., freeze-dried) preparation in combination with complex organic excipients and stabilizers such as nonionic surface active agents (i.e., surfactants), various sugars, organic polyols and/or human serum albumin. In another embodiment, a pharmaceutical composition comprises a lyophilized GH modified by CTPs as described in sterile water for injection. In another embodiment, a pharmaceutical composition comprises a lyophilized growth hormone as described in sterile PBS for injection. In another embodiment, a pharmaceutical composition comprises a lyophilized growth hormone as described in sterile 0.9% NaCl for injection.

In another embodiment, the pharmaceutical composition comprising a GH modified by CTPs as described herein and complex carriers such as human serum albumin, polyols, sugars, and anionic surface active stabilizing agents. See, for example, WO 89/10756 (Hara et al.—containing polyol and p-hydroxybenzoate). In another embodiment, the pharmaceutical composition comprises a growth hormone as described herein and lactobionic acid and an acetate/glycine buffer. In another embodiment, the pharmaceutical composition comprising a GH modified by CTPs as described herein and amino acids, such as arginine or glutamate that increase the solubility of interferon compositions in water.

In another embodiment, the pharmaceutical composition comprises a lyophilized GH modified by CTPs as described herein and glycine or human serum albumin (HSA), a buffer (e.g. acetate) and an isotonic agent (e.g NaCl). In another embodiment, the pharmaceutical composition comprises a lyophilized GH modified by CTPs as described herein and phosphate buffer, glycine and HSA.

In another embodiment, the pharmaceutical composition comprising a GH modified by CTPs as described herein is stabilized when placed in buffered solutions having a pH between about 4 and 7.2. In another embodiment, the pharmaceutical composition comprising a GH modified by CTPs as described herein is stabilized with an amino acid as a stabilizing agent and in some cases a salt (if the amino acid does not contain a charged side chain).

In another embodiment, the pharmaceutical composition comprising a GH modified by CTPs as described herein is a liquid composition comprising a stabilizing agent at between about 0.3% and 5% by weight which is an amino acid.

In another embodiment, the pharmaceutical composition comprising a GH modified by CTPs as described herein provides dosing accuracy and product safety. In another embodiment, the pharmaceutical composition comprising a GH modified by CTPs as described herein provides a biologically active, stable liquid formulation for use in injectable applications. In another embodiment, the pharmaceutical composition comprises a non-lyophilized GH modified by CTPs as described herein.

In another embodiment, the pharmaceutical composition comprising a GH modified by CTPs as described herein provides a liquid formulation permitting storage for a long period of time in a liquid state facilitating storage and shipping prior to administration.

In another embodiment, the pharmaceutical composition comprising a GH modified by CTPs as described herein comprises solid lipids as matrix material. In another embodiment, the injectable pharmaceutical composition comprising a GH modified by CTPs as described herein comprises solid lipids as matrix material. In another embodiment, the production of lipid microparticles by spray congealing was described by Speiser (Speiser and al., Pharm. Res. 8 (1991) 47-54) followed by lipid nanopellets for peroral administration (Speiser EP 0167825 (1990)). In another embodiment, lipids, which are used, are well tolerated by the body (e.g. glycerides composed of fatty acids which are present in the emulsions for parenteral nutrition).

In another embodiment, the pharmaceutical composition comprising a GH modified by CTPs as described herein is in the form of liposomes (J. E. Diederichs and al., Pharm./nd. 56 (1994) 267-275).

In another embodiment, the pharmaceutical composition comprising a GH modified by CTPs as described herein comprises polymeric microparticles. In another embodiment, the injectable pharmaceutical composition comprising a GH modified by CTPs as described herein comprises polymeric microparticles. In another embodiment, the pharmaceutical composition comprising a GH modified by CTPs as described herein comprises nanoparticles. In another embodiment, the pharmaceutical composition comprising a GH modified by CTPs as described herein comprises liposomes. In another embodiment, the pharmaceutical composition comprising a GH modified by CTPs as described herein comprises lipid emulsion In another embodiment, the pharmaceutical composition comprising a GH modified by CTPs as described herein comprises microspheres. In another embodiment, the pharmaceutical composition comprising a GH modified by CTPs as described herein comprises lipid nanoparticles. In another embodiment, the pharmaceutical composition comprising a GH modified by CTPs as described herein comprises lipid nanoparticles comprising amphiphilic lipids. In another embodiment, the pharmaceutical composition comprising a GH modified by CTPs as described herein comprises lipid nanoparticles comprising a drug, a lipid matrix and a surfactant. In another embodiment, the lipid matrix has a monoglyceride content which is at least 50% w/w.

In one embodiment, compositions of the present invention are presented in a pack or dispenser device, such as an FDA approved kit, which contain one or more unit dosage forms containing the active ingredient. In one embodiment, the pack, for example, comprise metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

In one embodiment, it will be appreciated that the GH modified by CTPs of the present invention can be provided to the individual with additional active agents to achieve an improved therapeutic effect as compared to treatment with each agent by itself. In another embodiment, measures (e.g., dosing and selection of the complementary agent) are taken to adverse side effects which are associated with combination therapies.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference. Other general references are provided throughout this document.

Example 1

Generation of hGH Constructs

Materials and Methods

Four hGH clones (variants of 20 kD protein) were synthesized. Xba I-Not I fragments containing hGH sequences from the four variants were ligated into the eukaryotic expression vector pCI-dhfr previously digested with XbaI-NotI. DNA from the 4 clones (401-0, 1, 2, 3 and 4) was prepared. Another partial hGH clone (1-242 bp) from 22 kD protein was also synthesized (0606114). Primers were ordered from Sigma-Genosys. The primer sequences used to generate the hGH modified by CTPs polypeptides of the present invention are summarized in Table 1, hereinbelow.

TABLE 1

| Primer number | SEQ ID NO | sequence | Restriction site (underlined in sequence) |
|---|---|---|---|
| 25 | 18 | 5' <u>CTCTAGA</u>GGACATGGCCAC 3' | XbaI |
| $32^R$ | 19 | 5' ACAGGGAGGTCTGGGGGTTCTGCA 3' | |
| 33 | 20 | 5' TGCAGAACCCCCAGACCTCCCT-GTGC 3' | |
| $4^R$ | 21 | 5' CCAAACTCATCAATGTATCTTA 3' | |
| 25 | 22 | 5' <u>CTCTAGA</u>GGACATGGCCAC 3' | XbaI |
| $35^R$ | 23 | 5' CGAACTCCTGGTAGGTGTCAAAGGC 3' | |
| 34 | 24 | 5' GCCTTTGACACCTACCAGGAGTTCG 3' | |
| $37^R$ | 25 | 5' AC<u>GCGGCCGC</u>ATCCAGACCTTCATCACT GAGGC 3' | NotI |
| $39^R$ | 26 | 5' <u>GCGGCCGC</u>GGACTCATCAGAAGCCGCAG CTGCCC 3' | |

Construction of 402-0-p69-1 (hGH) (SEQ ID NO: 5):

hGH is the wild type recombinant human growth hormone (without CTP) which was prepared for use as control in the below described experiments.

Three PCR reactions were performed. The first reaction was conducted with primer 25 and primer $32^R$ and plasmid DNA of 0606114 (partial clone of hGH 1-242 bp) as a template; as a result of the PCR amplification, a 245 bp product was formed.

The second reaction was conducted with primer 33 and primer $4^R$ and plasmid DNA of 401-0-p57-2 as a template; as a result of the PCR amplification, a 542 bp product was formed.

The last reaction was conducted with primers 25 and $4^R$ and a mixture of the products of the previous two reactions as a template; as a result of the PCR amplification, a 705 bp product was formed and ligated into the TA cloning vector (Invitrogen, catalog K2000-01). The XbaI-NotI fragment containing hGH-0 sequence was ligated into the eukaryotic expression vector pCI-dhfr. The vector was transfected into DG-44 CHO cells. Cells were grown in protein-free medium.

Construction of 402-1-p83-5 (hGH-CTP)—SEQ ID NO: 9 and 402-2-p72-3(hGH-CTPx2)—SEQ ID NO: 10:

hGH-CTP is a recombinant human growth hormone which was fused to 1 copy of the C-terminal peptide of the beta chain of human Chorionic Gonadotropin (CTP). The CTP cassette of hGH-CTP was attached to the C-terminus (one cassette). hGH-CTP-CTP is a recombinant human growth hormone which was fused to 2 copies of the C-terminal peptide of the beta chain of human Chorionic Gonadotropin (CTP). The two CTP cassettes of hGH-CTP-CTP were attached to the C-terminus (two cassettes).

Construction of hGH-CTP and hGH-CTP-CTP was performed in the same way as the construction of hGH-0. pCI-dhfr-401-1-p20-1 (hGH*-ctp) and pCI-dhfr-401-2-p21-2 (hGH*-ctp x2) were used as templates in the second PCR reaction.

hGH-CTP and hGH-CTP-CTP were expressed in DG-44 CHO cells. Cells were grown in protein-free medium. The molecular weight of hGH-CTP is ~30.5 kD since hGH has a MW of 22 kD while each "CTP cassette" contributes 8.5 kD to the overall molecular weight (see FIG. 1). The molecular weight of hGH-CTP-CTP is ~39 kD (see FIG. 1).

Construction of 402-3-p81-4 (CTP-hGH-CTP-CTP)— SEQ ID NO: 11 and 402-4-p82-9(CTP*hGH-CTP-CTP)— SEQ ID NO: 12:

CTP-hGH-CTP-CTP is a recombinant human growth hormone which was fused to 3 copies of the C-terminal peptide of the beta chain of human Chorionic Gonadotropin (CTP). The three CTP cassettes of CTP-hGH-CTP-CTP were attached to both N-terminus (one cassette) and the C-terminus (two cassettes). tCTP-hGH-CTP-CTP is a recombinant human growth hormone which is fused to 1 truncated and 2 complete copies of the C-terminal peptide of the beta chain of human Chorionic Gonadotropin (CTP). The truncated CTP cassette of tCTP-hGH-CTP-CTP was attached to the N-terminus and two CTP cassettes were attached to the C-terminus (two cassettes).

Three PCR reactions were performed. The first reaction was conducted with primer 25 and primer $35^R$ and plasmid DNA of p401-3-p12-5 or 401-4-p22-1 as a template; as a result of the PCR amplification, a 265 or 220 bp product was formed. The second reaction was conducted with primer 34 and primer $37^R$ and plasmid DNA of TA-hGH-2-q65-1 as a template; as a result of the PCR amplification, a 695 bp product was formed. The last reaction was conducted with primers 25 and $37^R$ and a mixture of the products of the previous two reactions as a template; as a result of the PCR amplification, a 938 or 891 bp product was formed and ligated into TA cloning vector (Invitrogen, catalog K2000-

01). Xba I-Not I fragment containing hGH sequence was ligated into our eukaryotic expression vector pCI-dhfr.

CTP-hGH-CTP-CTP and tCTP-hGH-CTP-CTP were expressed in DG-44 CHO cells. Cells were grown in protein-free medium. The molecular weight of CTP-hGH-CTP-CTP is ~47.5 kD (see FIG. 1) and the molecular weight of tCTP-hGH-CTP-CTP is ~43.25 kD (see FIG. 1).

Construction of 402-6-p95a-8 (CTP-hGH-CTP)—SEQ ID NO: 13:

Construction of hGH-6 was performed in the same way as the construction of hGH-3. pCI-dhfr-402-1-p83-5 (hGH-ctp) was used as a template in the second PCR reaction.

Construction of 402-5-p96-4 (CTP-hGH)—SEQ ID NO: 14:

PCR reaction was performed using primer 25 and primer $39^R$ and plasmid DNA of pCI-dhfr-ctp-EPO-ctp (402-6-p95a-8) as a template; as a result of the PCR amplification, a 763 bp product was formed and ligated into TA cloning vector (Invitrogen, catalog K2000-01). Xba I-Not I fragment containing ctp-hGH sequence was ligated into our eukaryotic expression vector pCI-dhfr to yield 402-5-p96-4 clone.

Example 2

In Vivo Bioactivity Tests of hGH-CTP Polypeptides of the Present Invention

The following experiment was performed in order to test the potential long acting biological activity of hGH-CTP polypeptides in comparison with commercial recombinant human GH and hGH.

Materials and Methods

Female hypophysectomized rats (60-100 g) received a weekly S.C. injection of 21.7 µg hGH-CTP polypeptides or a once daily 5 µg S.C. injection of control commercial rhGH.

Weight was measured in all animals before treatment, 24 hours following first injection and then every other day until the end of the study on day 21. Each point represents the group's average weight gain percentage ((Weight day 0-weight last day)/Weight day 0). Average weight gain was normalized against once-daily injection of commercial hGH. The treatment schedule is summarized in Table 2.

TABLE 2

| No. | Drug | N | Route | Treatment Schedule | Equimolar Dose (µg/rat) | Accumulate Dosage (µg/rat) | Dose Vol. (ml) |
|---|---|---|---|---|---|---|---|
| 1 | Vehicle | 7 | s.c. | days 1, 7 and 13; 1/W | NA | NA | 0.25 |
| 2 | Mock | 7 | s.c | days 1, 7 and 13; 1/W | NA | NA | 0.25 |
| 3 | hGH SEQ ID NO: 5 | 7 | s.c | days 1, 7 and 13; 1/W | 21.7 | 65 | 0.25 |
| 4 | hGH-CTP SEQ ID NO: 9 | 7 | s.c. | days 1, 7 and 13; 1/W | 21.7 | 65 | 0.25 |
| 5 | hGH-CTP-CTP SEQ ID NO: 10 | 7 | s.c. | days 1, 7 and 13; 1/W | 21.7 | 65 | 0.25 |
| 6 | CTP-hGH-CTP-CTP SEQ ID NO: 11 | 7 | s.c. | days 1, 7 and 13; 1/W | 21.7 | 65 | 0.25 |
| 7 | tCTP-hGH-CTP-CTP SEQ ID NO: 12 | 7 | s.c. | days 1, 7 and 13; 1/W | 21.7 | 65 | 0.25 |
| 8 | Commercial hGH v.1 | 7 | s.c. | days 1, 7 and 13; 1/W | 21.7 | 65 | 0.25 |
| 9 | Commercial hGH v.1 | 7 | s.c. | days 1-13; d/W | 5 | 65 | 0.25 |

Results

Results are summarized in FIG. 2. These results show that CTP-hGH-CTP-CTP (SEQ ID NO: 11) and tCTP-hGH-CTP-CTP (SEQ ID NO: 12) induced over 120% weight gain compared to commercial rhGH which induced 100% weight gain.

Conclusion 3 weekly doses (Days of injections: 1, 7, and 13) of 21.7 µg of CTP-hGH-CTP-CTP (SEQ ID NO: 11) and tCTP-hGH-CTP-CTP (SEQ ID NO: 12) induced a 30% greater weight increase in hypophysectomised rats compared to commercial rhGH injected at the same accumulated dose which was administered once per day at a dose of 5 µg for 13 days.

Example 3

Pharmacokinetic Studies of CTP-Modified GH

Single-dose pharmacokinetic studies were conducted in Sprague-Dawley rats. All animal experimentation was conducted in accordance with the Animal Welfare Act, the Guide for the Care and Use of Laboratory Animals, and under the supervision and approval of the Institutional Animal Care and Use Committees of Modigene, Biotechnology General Ltd. Rats were housed either individually or two per cage in rooms with a 12-h light/dark cycle. Access to water (municipal supply) and noncertified rodent chow was provided ad libitum.

To compare the pharmacokinetics of CTP-hGH-CTP-CTP and GH in rats, four groups of Sprague-Dawley rats (270-290 g), three to six male rats per group. The rats were randomly assigned to four treatment groups (see Table 3). Rats were administered a single s.c. or i.v. injection of GH (50 µg/kg i.v. or s.c.) or CTP-hGH-CTP-CTP (108 µg/kg i.v.

or s.c.). With the exception of the predose sample, which was collected under isoflurane anesthesia, blood collection was performed in unanesthetized animals. Blood samples (approximately 0.25 ml) were collected in EDTA-coated microtainers for ELISA analyses of CTP-hGH-CTP-CTP plasma concentration at the times outlined in Table 3. After each sampling, the blood volume was replaced with an equal volume of sterile 0.9% saline Samples were stored on ice for up to 1 h prior to centrifugation and plasma harvest. Plasma samples were stored at approximately −20° C. prior to analysis.

TABLE 3

Experimental design of rat pharmacokinetic study

| Trt. Grp. | Test Article | No. of animals/ group/ timepoint | Dose Route | Gender | Dose Level (µg/kg) | Injected Vol. (µl) | Concentration (µg/ml)/ Total vol. (ml) | Time-Points * (hours post-dose) |
|---|---|---|---|---|---|---|---|---|
| 1 | Biotropin | 6# | SC | Male | 50 | 500 | 20/5 | 0 (Pre-dose) 0.5, 2, 4, 8, 24, 48 |
| 2 | CTP-hGH-CTP-CTP | 6# | SC | Male | 108 | 500 | 43.2/5 | 0.5, 2, 4, 8, 24, 48, 72, 96 |
| 3 | Biotropin | 6# | IV | Male | 50 | 300 | 20/3 | 0, 0.12, 2, 4, 8, 24 |
| 4 | CTP-hGH-CTP-CTP | 6# | IV | Male | 108 | 300 | 43.2/3 | 0.12, 2, 4, 8, 24, 48, 72 |
| | | Volume of blood sample/time point - 500 µl | | | | | | Terminal blood samples |

3 rats per time point.

A commercial sandwich ELISA kit specific for detection of human growth hormone (Roche Diagnostics) was used for evaluation of the rat plasma samples. This kit detects human growth hormone in plasma by means of an antibody sandwich ELISA format. This kit was initially used to measure the concentration of CTP-hGH-CTP-CTP in rat plasma. For these plasma samples, a CTP-hGH-CTP-CTP standard curve (1.2-100 ng/ml) was used and the concentrations of CTP-hGH-CTP-CTP in rat plasma were interpolated from this curve.

Standard pharmacokinetic parameters, including clearance (CL or CL/F), volume of distribution (Vd or Vd/F), half-life ($t_{1/2}$), area under the plasma concentration versus time curve (AUC), maximal observed plasma concentration ($C_{max}$) and time to maximal observed plasma concentration ($T_{max}$), were obtained from plasma albutropin or GH concentration/time curves by noncompartmental analysis using the modeling program WinNonlin (Pharsight, version 3.1). Plasma CTP-hGH-CTP-CTP or GH concentration data were uniformly weighted for this analysis. The AUC was calculated using the log-linear trapezoidal analysis for the i.v. data and the linear-up/log-down trapezoidal method for the s.c. data. Plasma concentration profiles for each rat (with the exception of the s.c. albutropin data) or monkey were analyzed individually, and mean±standard error of the mean (S.E.M.) values for the pharmacokinetic parameters are reported in Table 4 and FIG. 4.

CTP-hGH-CTP-CTP is a single chain protein of 275 amino acids and up to twelve O-linked carbohydrates. The structure consists of modified human Growth Hormone (Somatropin) attached to three copies of the C-terminal peptide (CTP) of the beta chain of human Chorionic Gonadotropin (hCG); one copy at the N-terminus and two copies (in tandem) at the C terminus Human Growth Hormone is comprised of 191 amino acids. CTP is comprised of 28 amino acids and four O-linked sugar chains.

Example 4

Pharmacokinetics of CTP-Modified GH in SD Rats

The pharmacokinetics of CTP-hGH-CTP-CTP was evaluated and compared to that of commercial hGH (Biotropin).

TABLE 4

Mean pharmacokinetic parameters following single-dose i.v. and s.c. administration of CTP-hGH-CTP-CTP and GH (Biotropin) in Sprague-Dawley rats.
PK Statistic

| | | SC | | IV | |
|---|---|---|---|---|---|
| Parameters | Units | Biotropin | CTP-hGH-CTP-CTP | Biotropin | CTP-hGH-CTP-CTP |
| Dose | mg/Kg | 50 | 50 | 50 | 50 |
| AUClast | hr * ng/mL | 41 | 680 | 162.7 | 1568.3 |
| Cmax | ng/ml | 13 | 36.8 | 275.8 | 926 |
| Tmax | hr | 0.5 | 8 | 0 | 0 |
| MRT | hr | 2.5 | 12.9 | 0.5 | 9.9 |
| T½ alpha | hr | | 1.58 | | 0.74 |
| T½ beta | hr | 1.73 | 9 | 0.5 | 6.9 |

Data Statistical Analysis

Analysis of serum samples was performed in order to determine specific concentration levels for each sample. Concentration and time-point data were processed using WinNonLin noncompartmental analysis.

Figure 4A:
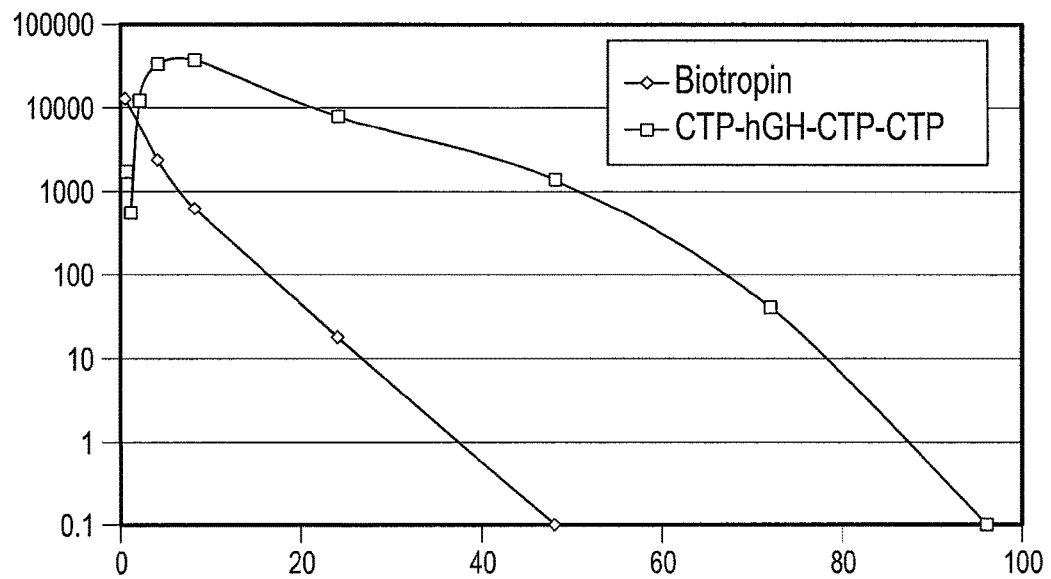
FIG. 4 are graphs showing the mean plasma CTP-hGH-CTP-CTP or GH concentrations (pg/ml) following a single i.v. or s.c. dose of CTP-hGH-CTP-CTP or GH in rats (n=3-6 per dose/route).
Figure 4B:
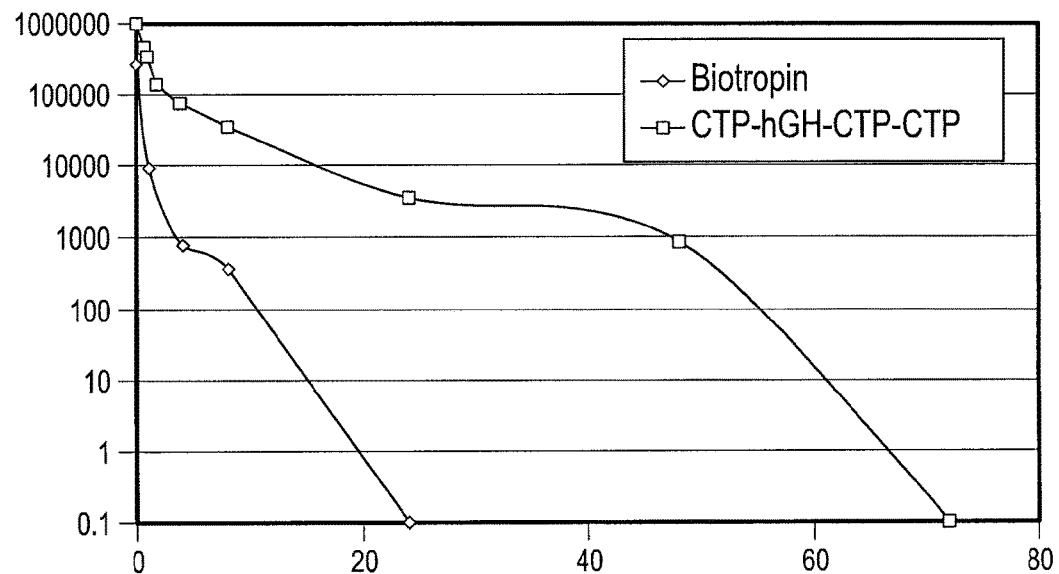

Parameters that were determined included: AUC, MRT, t½, Cmax, and Tmax. FIG. 4 demonstrates the superior pharmacokinetic profile of CTP-hGH-CTP-CTP plasma concentration compared to GH concentrations (pg/ml) following a single i.v. or s.c. dose of CTP-hGH-CTP-CTP or GH in rats (n=3-6 per dose/route).

Following a single S.C. injection of 50 µg/kg, clearance of CTP-hGH-CTP-CTP from SD rat's blood was significantly slower than that of CTP-hGH-CTP and of Biotropin. The corresponding calculated half-life times and AUCs were:

| Biotropin | T½ 1.7 h, AUC 41 hr * ng/mL |
| CTP-hGH-CTP | T½ 8.5 h, AUC 424 hr * ng/mL |
| CTP-hGH-CTP-CTP | T½ 9.0 h, AUC 680 hr * ng/mL |

Conclusion:

CTP-hGH-CTP-CTP was chosen as the final candidate out of 6 other variants. CTP-hGH-CTP-CTP demonstrated superior performance in terms of biological activity and pharmacokinetics.

Example 5

Weight Gain Assay (WGA) for Single Dose/Repeated Dose of CTP-Modified GH

Hypophysectomized (interaural method) male rats, 3-4 weeks of age, were obtained from CRL Laboratories. During a post-surgical acclimation period of 3 weeks, rats were examined and weighed twice weekly to eliminate animals deemed to have incomplete hypophysectomy evidenced by weight gain similar to that of sham-operated rats. Those rats with incomplete hypophysectomized were eliminated from the study. The average body weights of the hypophysectomized were 70-90 grams, at the time of the experiment. This is the standard USP and EP bioassay for hGH. Hypophysectomized rats (rats from which the pituitary gland was removed) lose their ability to gain weight. Injections of hGH (and of CTP-hGH-CTP-CTP) to these rats results in weight gain. Based on the measured weight gain along a defined period of time and the amount of hGH injected, the specific activity of hGH (and CTP-hGH-CTP-CTP) is determined Rats were administered either a single s.c. doses of 0.4, 0.8 and 4 mg/Kg or repeated s.c. doses of 0.6 and 1.8 mg/Kg 4 days apart for 3 weeks. Individual body weights of all animals are determined at randomization, prior to the first dosing, thereafter every two days or in case of decedents at the time of death, and prior to sacrifice.

Single Dose and Repeated Dose Weight Gain Assay

Figure 5:
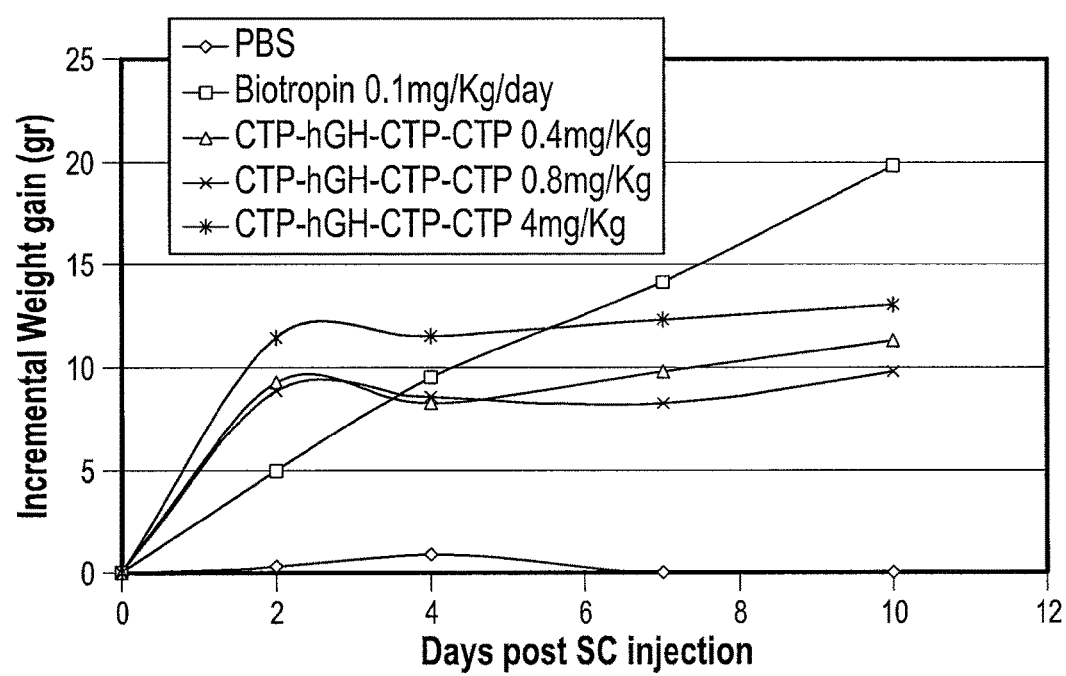
FIG. 5 are graphs showing the mean incremental weight gain following a single s.c. doses of CTP-hGH-CTP-CTP (0.4, 0.8 and 4 mg/Kg) in hypophysectomized rats in comparison to daily GH injections (0.1 mg/Kg/Day) (n=10 per dose).

The results comparing whole body growth response following different dosing patterns of CTP-hGH-CTP-CTP in hypophysectomized rats are demonstrated in FIG. 5. The results demonstrate that a single injection of 0.4 & 0.8 mg/Kg/day doses of hGH-CTP were equivalent to 4 daily injections of 0.1 mg/Kg/day of Biotropin. The peak of the hGH-CTP effect was after 2 days.

Figure 6:
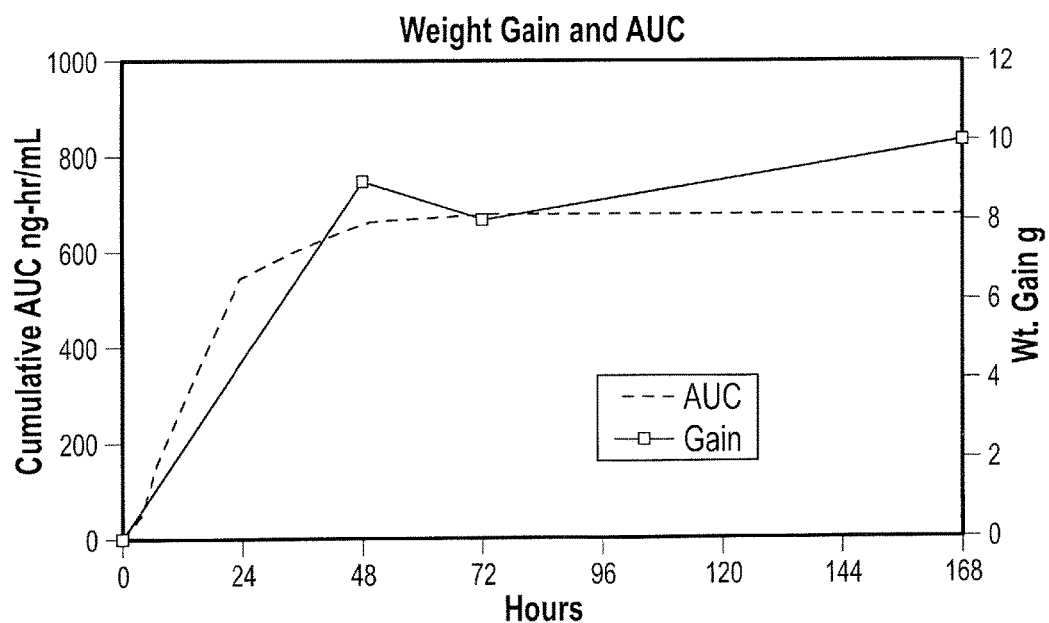
FIG. 6 is a graph showing the area Under the Curve following single injection of CTP-hGH-CTP-CTP correlates with Body Weight gain in Rats.

FIG. 6 further demonstrates that the area under the curve following single injection of CTP-hGH-CTP-CTP correlates with Body Weight gain in Rats. Thus, the collective data demonstrates that body weight gain is closely correlated with cumulative AUC.

Figure 7:
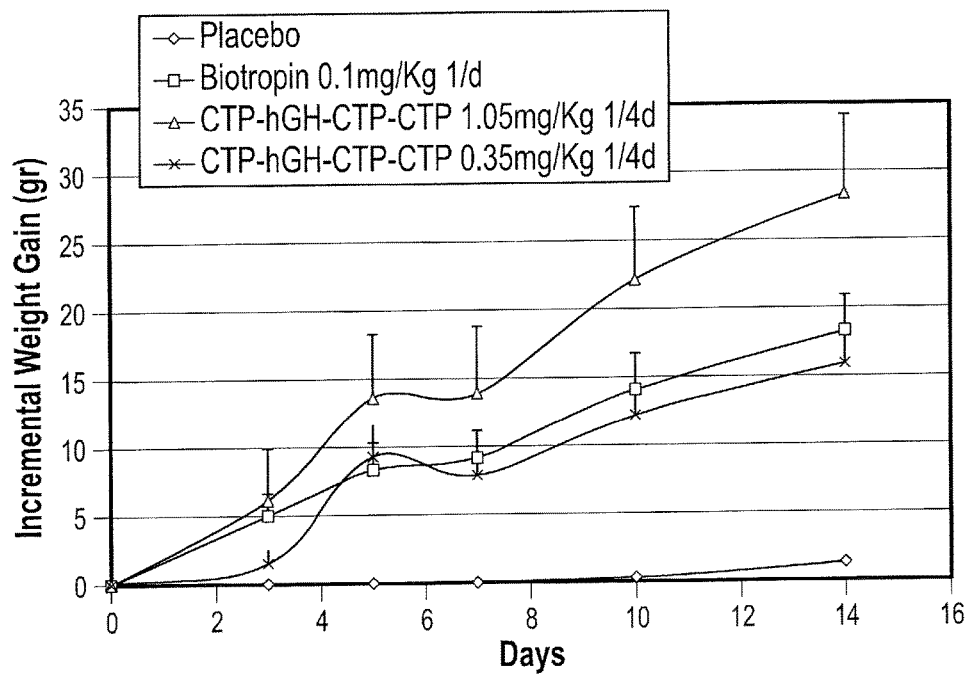
FIG. 7 is a graph showing the incremental weight gain following an s.c. doses of CTP-hGH-CTP-CTP (0.4, 0.8 and 4 mg/Kg) 4 days apart in hypophysectomized rats in comparison to daily GH injections (0.1 mg/Kg/Day) (n=10 per dose).

The hGH-CTP construct administered 4 days apart promotes the same weight gain as daily injections of Biotropin as demonstrated in FIG. 7. Half-life of hGH in humans is expected to be 5× better than in rats—indicating potential peak effect in humans after 10 days for one single injection. These results support administration of hGH-CTP construct, CTP-hGH-CTP-CTP, once weekly or biweekly in humans.

Example 6

Pharmacodynamics/Pharmacokinetics Studies of CTP-Modified GH

Hypophysectomized (interaural method) male rats, 3-4 weeks of age, were obtained from CRL Laboratories. During a post-surgical acclimation period of 3 weeks, rats were examined and weighed twice weekly to eliminate animals deemed to have incomplete hypophysectomy evidenced by weight gain similar to that of sham-operated rats. Those rats with incomplete hypophysectomized were eliminated from the study. The average body weights of the hypophysectomized and sham rats were 70 and 150 g, respectively, at the time of the experiment.

Rats were administered a single s.c. with CTP-hGH-CTP-CTP, vehicle, human growth hormone CTP-hGH-CTP-CTP or human growth hormone (20 µg/rat) was administered s.c. in an injection volume of 0.2 ml/rat. The dose of GH was 0.35 and 1.05 µg/Kg, a dose of growth hormone that was equimolar with the amount of GH in a corresponding 0.6 and 1.8 µg/Kg dose of CTP-hGH-CTP-CTP. The treatment groups are summarized in Table 4. Following injection, plasma samples for IGF-1 analyses were obtained at the times described in Table 5. Samples were analyzed for IGF-1 concentration using a commercial ELISA (R&D systems).

Weekly administration of CTP-modified hGH was successful in maintaining IGF-I within the normal range as standard GH and in addition it also maintains body weight as standard GH.

TABLE 5

Treatment schedule for hypophysectomized rat study

| Trt. Grp. | Test Article | No. of animals/group/timepoint | Dose Route | Eq. Dose (mg/rat) | Eq. Dosage (mg/Kg) | CTP-hGH-CTP-CTP Conc. mg/ml | Dose Vol. (ml) | Time-Points * (hours post-dose) |
|---|---|---|---|---|---|---|---|---|
| M7 | Biotropin | 9 | SC | 0.032 | 0.35 | 0.16 | 0.2 | 0 (Pre-dose) 0.5, 2, 4, 8, 24, 48, 72, 96 |
| M8 | Biotropin | 9 | SC | 0.095 | 1.05 | 0.475 | 0.2 | 0 (Pre-dose) 0.5, 2, 4, 8, 24, 48, 72, 96 |
| M9 | EN648-01-08-005 | 12 | SC | 0.032 (0.055) | 0.35 (0.6) | 0.275 | 0.2 | 1, 2, 4, 8, 24, 48, 72, 96 |
| M10 | EN648-01-08-005 | 12 | SC | 0.095 (0.165) | 1.05 (1.8) | 0.825 | 0.2 | 1, 2, 4, 8, 24, 48, 72, 96 |
| | | Volume of blood sample/time point - 500 µl | | | | | | Terminal blood samples |

Non-compartmental pharmacokinetic analysis was performed on the mean serum concentration versus time curves for each group. CTP-hGH-CTP-CTP Cmax was significantly higher than Biotropin Cmax. The terminal half-live of CTP-hGH-CTP-CTP was 6 times higher than Biotropin.

TABLE 6

Pharmacokinetic Parameter Estimates of CTP-hGH-CTP-CTP and Biotropin Following a Single Subcutaneous Injection in hypophysectomized Rats

| Group | Dose mg/kg | Gender | Cmax ng/mL | Tmax hr | $AUC_{0-\infty}$ ng-hr/mL | $AUC_{0-t}$ ng-hr/mL | CL/F mL/hr/kg | $T_{1/2}$ hr |
|---|---|---|---|---|---|---|---|---|
| CTP-hGH-CTP-CTP | 1.8 | M | 2,150 | 8 | 37,713 | 37,695 | 0.928 | 6.86 |
| hGH | 0.6 | M | 681 | 8 | 11,505 | 11,489 | 3.042 | 6.8 |
|  | 1.05 | M | 1,078 | 0.5 | 3,541 | 3,540 | 9.884 | 1 |
|  | 0.35 | M | 439 | 0.5 | 1,279 | 1,279 | 27.36 | 1 |

Figure 8:
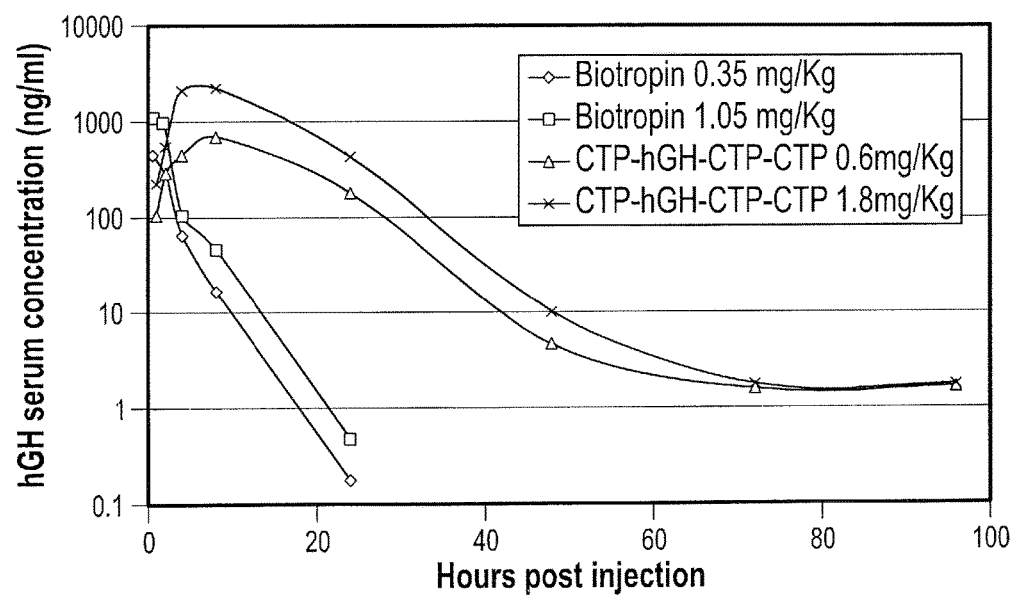
FIG. 8 is a graph showing hGH serum concentration in hypophysectomized rat following SC injection of CTP-hGH-CTP-CTP and commercial hGH. Single dose of CTP-hGH-CTP-CTP 0.6 or 1.8 mg/Kg and Biotropin 0.35 or 1.05 mg/Kg were injected subcutaneously to hypophysectomised rats for determination of PK/PD profile. Serum hGH post injection was measured using specific ELISA kits.

The $AUC_{0-t}$ and the $AUC_{0-\infty}$ were very similar suggesting the duration of sampling was adequate to characterize the pharmacokinetic profiles. AUC of CTP-hGH-CTP-CTP was 10 times higher than of Biotropin. Moreover, Cmax was generally proportional to dose and for CTP-hGH-CTP-CTP and it was twice higher than Cmax of Biotropin. However, as shown in FIG. 8, Tmax of CTP-hGH-CTP-CTP was 8 hr as compare to 0.5 hr of Biotropin, and the terminal half-lives did not appear to vary with dose level. T½ of CTP-hGH-CTP-CTP was 6.8 times longer than of Biotropin.

Figure 9:
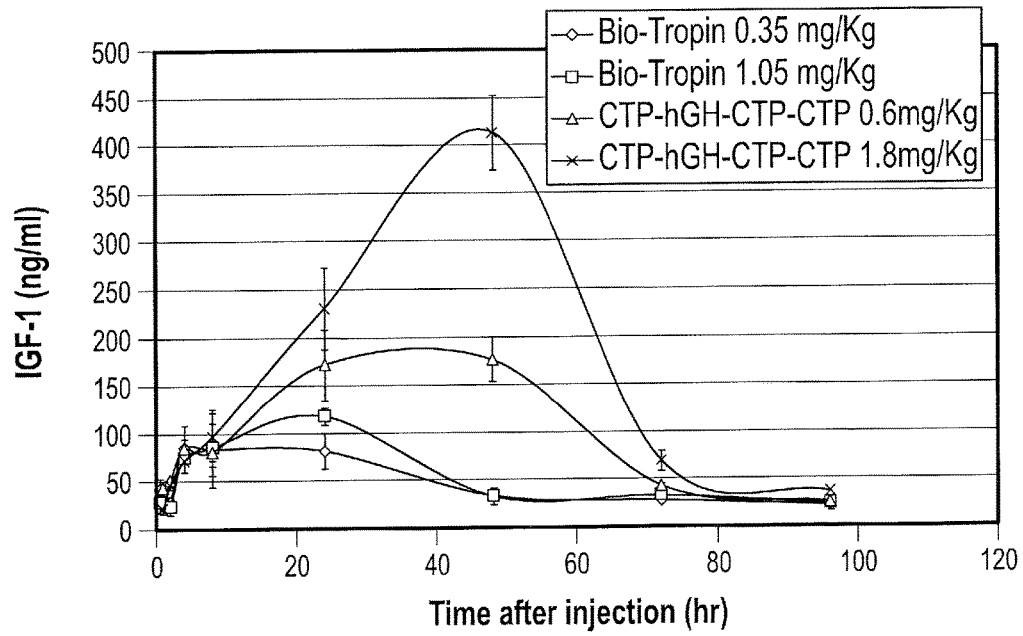
FIG. 9 is a graph showing IGF-1 serum levels in Hypophysectimized Rats Following SC injection of CTP-hGH-CTP-CTP and commercial hGH. Single dose of CTP-hGH-CTP-CTP 0.6 or 1.8 mg/Kg and Biotropin 0.35 or 1.05 mg/Kg were injected subcutaneously to hypophysectomised rats for determination of PK/PD profile. Serum IGF-I post injection was measured using specific ELISA kits (Roche Diagnostics).

Indirect effects of GH are mediated primarily by an insulin-like growth factor-I (IGF-I), a hormone that is secreted from the liver and other tissues in response to growth hormone. A majority of the growth promoting effects of growth hormone is actually due to IGF-I acting on its target cells. Accordingly, the effect of the CTP-hGH construct, CTP-hGH-CTP-CTP, on IGF-1 serum levels in Hypophysectimized Rats was measured. FIG. 9 presents results of IGF-1 serum levels in Hypophysectimized Rats Following SC injection of CTP-hGH-CTP-CTP and commercial hGH.

Single dose of CTP-hGH-CTP-CTP 0.6 or 1.8 mg/Kg and Biotropin 0.35 or 1.05 mg/Kg were injected subcutaneously to hypophysectomised rats for determination of PK/PD profile. Serum IGF-I post injection was measured using specific ELISA kits (Roche Diagnostics).

The cumulative serum levels of IGF-I following injection of CTP-hGH-CTP-CTP was significantly higher than following injection of Biotropin. Cmax was generally proportional to dose and for CTP-hGH-CTP-CTP it was 3-4 times higher than Cmax of Biotropin. Tmax of CTP-hGH-CTP-CTP was 36-48 hr as compare to 20-24 hr of Biotropin. In conclusion, higher hGH levels and longer presence in serum result in significant increase in IGF-1 levels.

Example 7

Carbohydrate Content and Sialic Acid Content of CTP-Modified GH

Analysis of O-glycans is based on a Prozyme kit. O-glycans are chemically and enzymatically cleaved from the protein and separated from peptides using paper chromatography. Sequencing of the O-glycan pool is performed by sequential enzymatic digestions (exo-glycosidases) followed by HPLC analysis compared to standards.

Glycoprofiling with Sequence Analysis

Glycoprofiling was performed by Ludger Ltd. Two samples (EN648 and RS0708) were taken through triplicate releases and each release was also analyzed by HPLC in triplicate. Triplicate 300 µg samples of EN648 and RS0708 and a single 100 µl sample of citrate/sodium chloride buffer, plus a positive control fetuin (250 µg) and a 100 µl water negative control, were ultra-filtrated by centrifugation using a molecular weight cut off membrane of 10,000 Da to replace the buffer with water, then taken through hydrazinolysis under O-mode conditions (6 h at 60° C.). Released glycans were re-N-acetylated and cleaned up by LudgerClean CEX cartridges. An aliquot of the released glycans was then labeled with 2-aminobenzamide (2AB), cleaned up with Ludger Clean S cartridges and analyzed by LudgerSep-N2 HILIC-HPLC.

Monosaccharide Content

Analysis of neutral monosaccharides requires hydrolysis of glycans to their constituent monosaccharide components. The hydrolysis was performed by Ludger Ltd, on intact glycoprotein samples. Specifically, 50 µg of intact glycoprotein was acid hydrolyzed, 2-AB (2-aminobenzamide) labeled and run on a reverse phase HPLC column. This method hydrolyzes all glycans present on the glycoprotein inclusive of N and O linked types.

Sialic Acid Profiling

Two samples (EN648 and RS0708) and a buffer control were analyzed. Sialic acid analysis requires mild acid release of the monosaccharides followed by DMB fluorophore labeling and HPLC analysis on a LudgerSep-R1 column. 50 µg of intact glycoprotein was acid hydrolyzed for each analysis.

Glyco Analysis of CTP-hGH-CTP-CTP

TABLE 7

Glycan analysis. Structural assignments and percentage areas of peaks are based upon HPLC and enzyme array digests.

| Peak ID[a] | GU[b] | Structure[c] | name | Percent from total glycans[e] | | | |
|---|---|---|---|---|---|---|---|
| | | | | Und[d] | NAN1 | ABS | ABS BTG |
| 1[f] | 0.92 | | GalNAc | 0.4 | 0.4 | 0.6 | 53.0 |
| 2[f] | 1.02 | | galactose | 1.9 | 9.7 | 23.8 | 26.5 |
| * | 1.72 | | | 4.3 | 4.6 | 2.3 | |
| 3 | 1.79 | | Galβ1-3GalNAc | 2.3 | 67.7 | 69.4 | 17.1 [h] |
| 4[g] | 2.25 | | NeuNAcα2-3Gal | 19.8 | 13.0 [h] | | |
| * | 2.57 | | | 1.5 | 1.9 | 1.1 | 1.1 |
| 5 | 2.90 | | NeuNAcα2-3Galβ1-3 GalNAc | 70.6 | | | |
| * | 3.58 | | | 0.6 | 0.7 | 0.6 | |
| 6 | 3.22 | | Galβ1-3[NeuNAcα2-6] GalNAc | 0.9 | 2.3 | | |
| 7 | 4.42 | | NeuNAcα2-3Galβ1-3 [NeuNAcα2-6]GalNAc | 1.8 | | | |

The monosaccharide profiles indicate that the CTP-hGH-CTP-CTP glycoprotein samples contain predominantly O-link type glycans. The major O-glycan peak is sialylated core 1 (Neu5Acα2-3Galβ1-3GalNAc). The major sialic acid is Neu5Ac and there are some minor peaks suggesting the presence of 3-4% of di-acetylated sialic acid N-acetyl-9-O- acetylneuraminic acid (Neu5, 9Ac2) and less than 1% N-glycolylneuraminic acid. There are also small amounts of Neu5Acα2-6(Galβ1-3)GalNAc.

Example 8

Pharmacokinetic/Toxicokinetic Analysis of CTP-Modified GH in Rhesus Monkeys

Serum concentrations versus time curves were generated for each animal. Non-compartmental analysis was performed with WinNonlin professional version 5.2.1 (Pharsight Corporation, Mt View Calif.). The estimated pharmacokinetic parameters are shown in Table 8 below:

TABLE 8

Estimates of CTP-hGH-CTP-CTP Pharmacokinetic Parameters (Mean ± SD) from Non-compartmental Analysis Following A Single Subcutaneous Injection in Rhesus Monkeys

| Parameter | 1.8 mg/kg | 90 mg/kg |
| --- | --- | --- |
| Cmax (µg/mL) | 2.073 ± 0.417 | 108.7 ± 46.0 |
| Tmax (hr) | 4 ± 0 | 11 ± 7 |
| $AUC_{0-t}$ (µg-hr/mL) | 38.7 ± 7.4 | 2,444 ± 394 |
| $AUC_{0-\infty}$ (µg-hr/mL) | 39.0 ± 7.3 | 2,472 ± 388 |
| CL/F (mL/hr/kg) | 47.5 ± 9.0 | 37.04 ± 4.78 |
| $T_{1/2}$ (hr) | 10.00 ± 1.47 | 9.85 ± 1.07 |
| Vz/F (mL/kg) | 701 ± 236 | 529 ± 104 |

The $AUC_{0-t}$ and the $AUC_{0-\infty}$ were very similar suggesting the duration of sampling was adequate to characterize the pharmacokinetic profiles. Cmax was proportional to dose. Tmax was later at the higher dose. Tmax was at 4 hours for all animals in the low dose group and was at 8 or 24 hours in the high dose group. Terminal half-lives are similar for the two dose groups.

AUC was approximately proportional to dose with a slightly larger than proportional AUC at the higher dose producing a slightly lower estimate for CL/F and Vz/F compared to the lower dose. It is not possible to say if CL and Vz are lower at the higher dose or if F is lower at the lower dose. There was overlap between the groups so it is questionable that this represents a meaningful difference in CL/F and Vz/F.

Pharmacokinetic parameters estimated by the model were very similar to those from non-compartment analysis. Absorption and elimination half-lives are shown in Table 9 below:

TABLE 9

Estimates of CTP-hGH-CTP-CTP Absorption and Elimination Half-lives (Mean ± SD) Following Subcutaneous Injection Derived From Pharmacokinetic Modeling in Rhesus Monkeys

| Dose | $T_{1/2\ abs}$ (hr) | $T_{1/2\ el}$ (hr) |
| --- | --- | --- |
| 1.8 mg/kg | 1.17 ± 0.40 | 10.41 ± 2.36 |
| 90 mg/kg | 6.49 ± 1.87 | 7.26 ± 1.85 |

The data indicate that the elimination rates are fairly similar between the groups with a slightly longer T½ el in the lower dose group. The absorption, however, is more than 5-fold slower following subcutaneous administration of 90 mg/kg compared to that following 1.8 mg/kg. As in the case of the non-compartmental analysis, modeling indicated a later Tmax at the high dose.

Although GH supplementation is effective in the treatment of GH deficiency in children and adults, the disadvantages of daily injections over extended periods of time limit its use by physicians in certain patient populations as well as increase the risk of dosing error, the number of care givers, the cost of treatment and/noncompliance. Especially important in certain populations, such as children of short stature who may not understand the implications of not following the prescribed GH dosing regimen, is the necessity of compliance to achieve the optimal benefit from GH therapy. The issue of finding a more suitable alternative to daily GH injections and subsequent compliance gains further importance as GH-deficient children transition into adults with a continuing need for GH treatment. The requirement of daily therapy is largely due to recombinant GH's short plasma half-life and has led to the development of a sustained release form of GH (Reiter E O. Attire K M., Mashing T J. Silverman B L. Kemp S F. Neolith R B. Ford K M. and Sanger P. A multimember study of the efficacy and safety of sustained release GH in the treatment of naive pediatric patients with GH deficiency. J. Clin. Endocrinol. Metab. 86 (2001), pp. 4700-4706.).

GH-CTP, a recombinant human growth hormone-CTP fusion protein, as provided herein, has a pharmacokinetic profile in the rat that is longer in duration than that of GH. This unique pharmacokinetic profile allows for intermittent administration of GH-CTP to achieve pharmacodynamic effects in growth-hormone-deficient rat as evidenced by growth and elevations in plasma IGF-1 levels, respectively.

GH-CTP offers a superior pharmacokinetic profile compared with that of GH when administered s.c. in the rat. There are substantial differences in plasma clearance of GH-CTP compared to GH. Specifically, plasma is cleared of GH-CTP at more than 6 times more slowly than GH following s.c. dosing. The terminal half-life and mean residence time of GH-CTP were approximately six times longer than that of GH in rats following s.c. administration. In addition, the Cl/F following s.c. dosing is 10 times lower for GH-CTP than for GH.

In an effort to examine whether the pharmacokinetic advantages in the rat translated to a pharmacodynamic benefit, the possibility that GH-CTP might stimulate growth in GH-deficient hypophysectomized rats with dosing regimens less frequent than daily was tested at equimolar CTP-hGH-CTP-CTP and GH dose levels. Single SC injection of GH-CTP promoted incremental weight gain which was equal to 4 daily consecutive injections of GH. In addition, the every fourth day administration schedule for GH-CTP shows enhanced body weight gain over GH.

Pharmacodynamically, the long circulation time of GH-CTP relative to GH in the hypophysectomized rats resulted in a prolonged IGF-1 response measured in blood plasma following a single s.c. injection. Subcutaneous administration of a single dose of GH-CTP increased circulating IGF-1 concentrations in a dose-dependent manner in the hypophysectomized rats. At the highest albutropin dose, IGF-1 concentrations were elevated above baseline for as long as 75 hours after a single administration. Thus, the enhanced circulation time of a single dose of GH-CTP resulted in substantial pharmacodynamic improvement over a single dose of GH, raising the possibility that GH-CTP could offer similar growth enhancement and decrease in body fat with reduced dosing frequency compared with standard GH treatment regimens.

Single CTPs modified hGH-dose of 90 mg/kg in Rhesus and 180 mg/kg in rats were well tolerated in both species. The allometric factor between rats and primates is approximately ×2 which is based on the anticipated clearance of proteins in these animals. In-line with industry-accepted extrapolation models for therapeutic proteins' half-life increase between species (FDA Guidance). 90 mg/kg in Primates has a PK profile slightly better than 180 mg/kg of CTPs modified hGH in Rat. Thus, allometric extrapolation to humans supports weekly or once/2 w injection.

The present concept utilizing a CTP-GH construct, reduced dosing frequency compared to the commercial GH recombinant product. Nutropin Depot® is a sustained release formulation of GH approved for use in pediatric populations; however, comparisons to historical controls have revealed that 1- and 2-year growth rates are significantly (p<0.001) lower in children given Nutropin Depot® (1-year growth rate 8.2±1.8 cm/year) than in children treated with GH (one-year growth rate 10.1±2.8 cm/year) (Silverman B L. Blethen S L. Reiter E O. Attie K M. Neuwirth R B. and Ford K M. A long-acting human growth hormone (Nutropin Depot®): efficacy and safety following two years of treatment in children with growth hormone deficiency. *J. Pediatr. Endocrinol. Metab.* 15 (2002), pp. 715-722.). The local effects of subcutaneously administered Nutropin Depot® include nodules, erythema, pain at the injection site, headache and vomiting. Preclinical toxicology studies in both rat and monkey have shown that s.c. administration of CTP-hGH-CTP-CTP produces no local reactions compared to vehicle. Given the medical need for a less frequently administered form of GH, the pharmacologic properties of CTP-hGH-CTP-CTP in this study in rats suggest that this product is favorable also in terms of toxicology and patient compliance. The sustained activity of CTP-hGH-CTP-CTP in the rat support its potential utility as an agent that requires only intermittent administration to attain a therapeutic benefit that is currently achieved with daily dosing.

Example 9

Long-Acting CTP-Modified Version of Human Growth Hormone (hGH-CTP) was Highly Effective in Growth Hormone Deficient Adults Phase II Clinical Trial A randomized, open-label, Phase II Clinical Trial was conducted to evaluate the safety, tolerability, pharmacokinetics and pharmacodynamic properties of hGH-CTP injected either weekly or twice-monthly in patients who currently receive daily injections of growth hormone. The trial was conducted at multiple sites in six countries. The three main cohorts in the trial received a single weekly dose of hGH-CTP, containing 30%, 45% or 100% of the equivalent cumulative commercial hGH dose that growth hormone-deficient adult patients receive over the course of seven days in the form of daily injections (referred to as the "30%", "45%" and "100%" cohorts, respectively). The data reflect results from 39 patients, 13 in each cohort. 2 females were included in each cohort.

In addition to the three main cohorts, growth hormone deficient adults were enrolled in an experimental fourth cohort, which is conducted outside of the formal Phase II trial. The patients in the experimental fourth cohort receive a single injection of hGH-CTP once every two weeks that contains 50% of the cumulative commercial dose of that growth hormone-deficient adult patients receive over a two-week period in the form of daily injections.

Efficacy for the three main cohorts receiving a single weekly injection of hGH-CTP is defined by measuring daily insulin-like growth factor 1 (IGF-1) levels within the desired therapeutic range over a period of seven days (during the last week of treatment in the study). The desired therapeutic range is defined as between +2 standard deviations through −2 standard deviations from the average IGF-1 levels expected in a normal population, stratified by age group and gender. In addition, the trial measured IGF-1 levels within a narrower range of +/−1.5 standard deviations for the purpose of observing the variance of the patients within the normal range.

Results:

Table 10 contains the average percent of days within the normal therapeutic range (+/−2 SD), average percent of days within a narrower normal therapeutic range (+/−1.5 SD), and average Cmax (highest concentration level) of IGF-1 for males, measured during the last treatment week, expressed in standard deviations from the normal population mean IGF-1 levels.

TABLE 10

Human Phase II Clinical Trial Results.

| Cohort | % Days Within Narrow Normal Range of IGF-1 (+/−1.5 SD) | % Days Within Normal Range of IGF-1 (+/−2 SD) | Avg. Cmax of IGF-1 (preferred below +2 SD) |
|---|---|---|---|
| 30% | 57% | 100% | −0.9 |
| 45% | 100% | 100% | 0.1 |
| 100% | 86% | 100% | 0.4 |

Two mg per week of hGH-CTP, containing 50% of the cumulative weekly hGH dose that an adult patient would usually be prescribed as the initial treatment dose, has a high likelihood of being defined as the starting dose for males and females in the adult Phase III.

There was no evidence of safety and/or tolerability issues, and no indication that hGH-CTP, when used in high doses, induced excessive levels of IGF-1 in patients or even levels above the normal range.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method of treating growth hormone deficiency in a human adult subject as measured by maintaining insulin-like growth factor (IGF-1) levels within a normal therapeutic range in said growth hormone deficient human subject, the method comprising administering to said human adult subject a therapeutically effective amount of a CTP-modified polypeptide consisting of (i) a human growth hormone, (ii) a single chorionic gonadotropin carboxy terminal peptide (CTP) attached to the amino terminus of said growth hormone, and (iii) two chorionic gonadotropin CTPs attached to the carboxy terminus of said growth hormone, wherein optionally (iv) a signal peptide is attached to the amino terminus of said amino terminal CTP, measuring IGF-1 levels to determine the maintenance of IGF-1 in said human adult subject, wherein said CTP-modified polypeptide consists of the amino acid sequence set forth in amino acids 27-301 of SEQ ID NO: 11 when said signal peptide is not attached, wherein said therapeutically effective amount consists of a single dose of approximately 1.8-2 mg/week of the CTP-modified polypeptide, wherein said administration maintains IGF-1 levels within a normal therapeutic range and treats said growth hormone deficient human subject.

2. The method of claim 1, wherein said CTP-modified polypeptide is administered at a dose of approximately 2 mg/administration.

3. The method of claim 1, wherein said CTP-modified polypeptide is administered subcutaneously to said subject.

4. The method of claim 1, wherein said CTP-modified polypeptide is encoded by the nucleotide sequence set forth in SEQ ID NO: 16.

5. The method of claim 1, wherein at least one CTP is glycosylated.

6. The method of claim 1, wherein said maintaining is for at least one week.

7. The method of claim 1, wherein the amino acid sequence of said signal peptide is set forth in SEQ ID NO: 3.

8. The method of claim 1, wherein said CTP-modified polypeptide is administered at a dose of approximately 1.8 mg/administration.

9. The method of claim 1, wherein said adult subject is male.

* * * * *